(12) United States Patent
Feder et al.

(10) Patent No.: US 7,115,375 B2
(45) Date of Patent: Oct. 3, 2006

(54) METHODS OF DIAGNOSING RENAL TUMORS BY DETERMINING THE EXPRESSION LEVEL OF RNA ENCODING THE HGPRBMY18 POLYPEPTIDE

(75) Inventors: John N. Feder, Belle Mead, NJ (US); Gabriel Mintier, Hightstown, NJ (US); Chandra S. Ramanathan, Wallingford, CT (US)

(73) Assignee: Bristol-Myers Squibb, Princeton, NJ (US)

( * ) Notice: Subject to any disclaimer, the term of this patent is extended or adjusted under 35 U.S.C. 154(b) by 0 days.

(21) Appl. No.: 10/768,878

(22) Filed: Jan. 30, 2004

(65) Prior Publication Data

US 2004/0161823 A1 Aug. 19, 2004

Related U.S. Application Data

(63) Continuation-in-part of application No. 10/262,313, filed on Sep. 30, 2002, now abandoned, which is a continuation-in-part of application No. 09/992,331, filed on Nov. 14, 2001, now abandoned.

(60) Provisional application No. 60/308,540, filed on Jul. 27, 2001, provisional application No. 60/261,782, filed on Jan. 16, 2001, provisional application No. 60/248,483, filed on Nov. 14, 2000.

(51) Int. Cl.
*C12Q 1/68* (2006.01)
*C07H 21/04* (2006.01)

(52) U.S. Cl. .................... 435/6; 536/23.5; 536/24.3
(58) Field of Classification Search .................... 435/6; 536/23.5, 24.3
See application file for complete search history.

(56) References Cited

U.S. PATENT DOCUMENTS 6,395,877 B1 5/2002 Glucksmann et al.
2002/0151705 A1 10/2002 Smith et al.

FOREIGN PATENT DOCUMENTS

| JP | 2001211885 | 8/2001 |
|----|-----------|--------|
| WO | WO0000611 | 1/2000 |
| WO | WO0050596 | 8/2000 |
| WO | WO0142288 | 6/2001 |
| WO | WO0242461 | 5/2002 |
| WO | WO02061087 A2 | 8/2002 |
| WO | WO02067868 | 9/2002 |
| WO | WO02068600 | 9/2002 |
| WO | WO03071272 A1 | 8/2003 |
| WO | WO03087366 A1 | 10/2003 |

OTHER PUBLICATIONS

NCBI Entrez Accession No. gi|17489470.
Alam, et al. (1990) Analytical Biochemistry 188:245-254.
Selbie, et al. (1998) TiPS 19:87-93.
Boss, et al. (1996) JBC 271:10429-10432.
George, et al. (1997) J. Neurochem. 69:1278-1285.
Suto, et al. (1997) J. Biomol. Screening 2:7-9.
Zlokarnik, et al. (1998) Science 279:84-88.
Fiering, et al. (1990) Genes & Develop. 4:1823-1834.
Karttunen et al., (1991) PNAS 88:3972-3976.
Hawes, et al. (1996) JBC 271:12133-12136.
Gilman, A. G., (1987) Ann. Rev. Biochem 56:615-649.
Salcedo, et al, (2000) Blood 96:34-40.
Sica, et al, (2000) Amer. Assoc. of Immunology 164:733-738.
Kypson, et al. (1999) Gene Therapy 6:1298-1304.
Dorn, et al. (1999) PNAS 96:6400-6405.
Wess, J., (1997) Biochemistry 11:346-354.
Whitney, et al. (1998) Nature Biotech. 16:1329-1333.
Chen, et al. (1999) J. Pharmacol. Toxicol. Methods 42:199-206.
Takauwa, et al. (2002) J. Biochem. 131:767-771.
Gustin, et al. (2002) Cancer and Metastasis Rev. 21:323-348.
Drews, J. (2000) Science 287:1960-1964.
Petersen, et al. (1999) Cancer Supplement j86:2540-2550.
Lorimer, et al. (1997) Biochem. and Biophysical Res. Comm. 241:558-564.
Yamada, et al. (1992) Molec. Endocrinology 6:2136-2142.
Sakurai, et al. (1998) Cell 92:573-585.
Habert-Ortoli, et al. (1994) PNAS 91:9780-9783.
Reppert, et al. (1994) Neuron 13:1177-1185.
Rees, et al. (1999) Signal Transduction: A Practical Approach. Oxford: Oxford University Press 171-221.
Swiss-Prot Accession No. O08858, Release 35, Nov. 1997.
Swiss-Prot Accession No. O43614, Release 39, May 2000.
Swiss-Prot Accession No. P30935, Release 26, Jul. 1993.
Swiss-Prot Accession No. P30936, Release 26, Jul. 1993.
Swiss-Prot Accession No. P30938, Release 26, Jul. 1993.
Swiss-Prot Accession No. P32745, Release 27, Oct. 1993.
Swiss-Prot Accession No. P47211, Release 33, Feb. 1996.
Swiss-Prot Accession No. P48040, Release 33, Feb. 1996.
Swiss-Prot Accession No. P56479, Release 36, Jul. 1998.
Swiss-Prot Accession No. P97295, Release 36, Jul. 1998.
Swiss-Prot Accession No. Q62805, Release 35, Nov. 1997.
Altschul, S.F. et al., "Gapped BLAST and PSI-Blast: a new generation of protein database search programs", Nucleic Acids Research, vol. 25, No. 17, pp. 3389-3402 (1997).

(Continued)

*Primary Examiner*—Ruixiang Li
(74) *Attorney, Agent, or Firm*—Stephen C. D'Amico

(57) ABSTRACT

The present invention describes a newly discovered human G-protein coupled receptor and its encoding polynucleotide. Also described are expression vectors, host cells, agonists, antagonists, antisense molecules, and antibodies associated with the polynucleotide and/or polypeptide of the present invention. In addition, methods for treating, diagnosing, preventing, and screening for disorders associated with aberrant cell growth, endocrine conditions, neurological conditions, and diseases or disorders related to the pituitary gland, colon, breast, lungs, kidney, and prostate are illustrated.

2 Claims, 13 Drawing Sheets

OTHER PUBLICATIONS

Bunzow, J.R. et al., "Cloning and expression of rat $D_2$ dopamine receptor cDNA", Nature, vol. 336, pp. 783-787 (1988).

Feng, Y. et al., "HIV-1 Entry Cofactor: Functional cDNA Cloning of a Seven-Transmembrane, G Protein-Coupled Receptor", Science, vol. 272, pp. 872-877 (1996).

Hofmann, K. et al., MF C-35: "A Database of Membrane Spanning Protein Segments", Biol. Chem. Hoppe-Seyler, vol. 374, p. 166 (1993).

Horn, F. et al., "G protein-coupled receptors *in silico*", J. Mol. Med., vol. 76, pp. 464-468 (1998).

Horn, F. et al., "The Interaction of Class B G Protein-Coupled Receptors with their Hormones", Receptors and Channels, vol. 5, pp. 305-314 (1998).

Johnson, G.L. et al., "The G-Protein Family and Their Interaction with Receptors", Endocrine Reviews, vol. 10, No. 3, pp. 317-331 (1989).

Kobilka, B.K. et al., "cDNA for the human $\beta_2$-adrenergic receptor: A protein with multiple membrane-spanning domains and encoded by a gene whose chromosomal location is shared with that of the receptor for platelet-derived growth factor", Proc. Natl. Acad. Sci. USA, vol. 84, pp. 46-50 (1987).

Kobilka, B.K. et al., "Cloning, Sequencing, and Expression of the Gene Coding for the Human Platelet $\alpha_2$-Adrenergic Receptor", Science, vol. 238, pp. 650-656 (1987).

Lefkowitz, R.J., "Variation on a theme", Nature, vol. 351, pp. 353-354 (1991).

Simon, M.I. et al., "Diversity of G Proteins in Signal Transduction", Science, vol. 252, pp. 802-808 (1991).

Hedge, et al., "A Concise Guide to cDNA Microarray Analysis", BioTechniques, vol. 29, pp. 548-562 (2000).

NCBI Entrez Accession No. AAZ49745 (gi:71843934), Chantratita, et al., Aug. 10, 2005.

NCBI Entrez Accession No. NT_030059 (gi:51467897), International Human Genome Sequencing Consortium, Aug. 20, 2004.

NCBI Entrez Accession No. XP_061208 (gi:17489470), NCBI Annotation Project, Aug. 1, 2002.

FIG. 1

```
ATGTCCCCTGAATGCGCGCGGGCAGCGGGCGACGCGCCCTTGCGCAGCCTGGAGCAAGCC
AACCGCACCCGCTTTCCCTTCTTCTCCGACGTCAAGGGCGACCACCGGCTGGTGCTGGCC
GCGGTGGAGACAACCGTGCTGGTGCTCATCTTTGCAGTGTCGCTGCTGGGCAACGTGTGC
GCCCTGGTGCTGGTGGCGCGCCGACGACGCCGCGGCGCGACTGCCTGCCTGGTACTCAAC
CTCTTCTGCGCGGACCTGCTCTTCATCAGCGCTATCCCTCTGGTGCTGGCCGTGCGCTGG
ACTGAGGCCTGGCTGCTGGGCCCCGTTGCCTGCCACCTGCTCTTCTACGTGATGACCCTG
AGCGGCAGCGTCACCATCCTCACGCTGGCCGCGGTCAGCCTGGAGCGCATGGTGTGCATC
GTGCACCTGCAGCGCGGCGTGCGGGGTCCTGGGCGGCGGGCGCGGGCAGTGCTGCTGGCG
CTCATCTGGGGCTATTCGGCGGTCGCCGCTCTGCCTCTCTGCGTCTTCTTCCGAGTCGTC
CCGCAACGGCTCCCCGGCGCCGACCAGGAAATTTCGATTTGCACACTGATTTGGCCCACC
ATTCCTGGAGAGATCTCGTGGGATGTCTCTTTTGTTACTTTGAACTTCTTGGTGCCAGGA
CTGGTCATTGTGATCAGTTACTCCAAAATTTTACAGATCACAAAGGCATCAAGGAAGAGG
CTCACGGTAAGCCTGGCCTACTCGGAGAGCCACCAGATCCGCGTGTCCCAGCAGGACTTC
CGGCTCTTCCGCACCCTCTTCCTCCTCATGGTCTCCTTCTTCATCATGTGGAGCCCCATC
ATCATCACCATCCTCCTCATCCTGATCCAGAACTTCAAGCAAGACCTGGTCATCTGGCCG
TCCCTCTTCTTCTGGGTGGTGGCCTTCACATTTGCTAATTCAGCCCTAAACCCCATCCTC
TACAACATGACACTGTGCAGGAATGAGTGGAAGAAAATTTTTTGCTGCTTCTGGTTCCCA
GAAAAGGGAGCCATTTTAACAGACACATCTGTCAAAAGAAATGACTTGTCGATTATTTCT
GGCTAA
```

FIG. 2

MSPECARAAGDAPLRSLEQANRTRFPFFSDVKGDHRLVLAAVETTVLVLIFAVSLLGNVC
ALVLVARRRRRGATACLVLNLFCADLLFISAIPLVLAVRWTEAWLLGPVACHLLFYVMTL
SGSVTILTLAAVSLERMVCIVHLQRGVRGPGRRARAVLLALIWGYSAVAALPLCVFFRVV
PQRLPGADQEISICTLIWPTIPGEISWDVSFVTLNFLVPGLVIVISYSKILQITKASRKR
LTVSLAYSESHQIRVSQQDFRLFRTLFLLMVSFFIMWSPIIITILLILIQNFKQDLVIWP
SLFFWVVAFTFANSALNPILYNMTLCRNEWKKIFCCFWFPEKGAILTDTSVKRNDLSIIS
G

FIG. 3

```
CCACGCGTCCGCGGACGCGTGGGAAGTAGCTGGGATTACAGGTACCTGCCACCATGCCCA
GCTAATTTTTGTATTTTTAGTAGAGACGGGGTTTCACCACGTTGGCCATGGCTGGTCTGG
AGCTCCCGACCTCAAGTGATCCACCCGCCTTGGCCTCCCAAAGTGCTGAGATTACAAGCA
TGAGCCACTGTGCCCAGTCAGTGCTTAGATTTCTTAAGACCCAACCTTAAGAAAGACAAT
TAGAAGACAGAGTGGGCAACTGGGAGAGGCCTGGTAATATGGCAGAGGGAAGAGGGGGTG
AAGGTGTGGGTGGCAGGAGGGTGGCTGGTTGGGGAAGTGGCCACTGGATCTTAGGCCACA
GGCATACTTTTCCATCTCCAGCTTCCTCATTTACAGAAAACGAGACTGCAGTGGTGTGAT
GGAAATGTGTGGGACGGGGACAGGTGACTGGCTTTCATTACTAACCAGAGGACAGCTTAG
ACAAGTCACTCTGGCTGGGCCTCAGTTTCCTTATCTCTAACGGGACTGGATTGCCCAGTG
CTCCTCAAACTGTGGCACCTGGGGCACATTCATAGCTTGTGTGTGAATCTGCCAGCCTTG
AAATATCTGTCTTCCTTGGATGGCAAGTTTATTAAAAATTTTGGAAGGACTCACTCTTTT
TATAAGAAAGCATTTATGTCATTGTTCAGAATGCAAATGTATATGCATTTTAGTTACAA
TAACTAATATTTGATAACATTTAACGAGTAATTACTGTGTGCCAAGTGTGCAAAACTCTA
GGTGAGCCTCACAATAACCTAATGGGGTATTATTATTCCCATTTTATAGATTAAAAATCT
GGGGTAGAGGGAGTAGATAATCCACCTAAAGACCTGTTATTAAGTAGTGATAAAAGATCT
CCACTCCCTCTCTCCCCCACAAAATATGGACTCATTACAAGTTGTTTTAGGATCTACCTC
CAGACCCATGGAGTTTCTTTAGTAAAGCCTGAACGACACAGGCCAAAATAATCTCCAAAG
GCCAGCTCTGACCCTTTTAAATCAATTTTAGCTAAATCCGTTCACAAAAGGCTTCGCACA
TCCAGTGTCCCTGAAAAATAAAGGAGGTTGGGCAGGCCCTGCGGGGCTCGAGGAATTCG
CTAAGTGAGTTTTCTGGCTTCTGGATACACTTTCAAAGGGCCAGAGGGCACGAGGCTTCC
GCCTTGGCCGCCACCTCCCCGGCCAGCTGCGGTGTTCGCGGCCAGTGTTGCCGGGCACTT
CCTGGTTCCCGCGCGCCCCGGGTGCAGCTCCCTGCACCCAGTGCTGGCGCTCCTCAGAAG
GGAGGGGGCCAGAGGCGAGATGTCGCAACCGCCTCCCTCCCTCTTTCCCCGCCTTGGCAC
TCAGTCGCCTCCCAGATGAGCACTCTCTCAGACCGCTGCGGGCCGCCAGGCGCCGGGA
```

FIG. 4

```
TTTTTCTTTATAGCCGAGTTTCTCACACCTGGCGAGCTGTGGCATGCTTTTAAACAGAGT
TCATTTCCAGTACCCTCCATCAGTGCACCCTGCTTTAAGAAAATGAACCTATGCAAATAG
ACATCCACAGCGTCGGTAAATTAAGGGGTGATCACCAAGTTTCATAATATTTTCCCTTTA
TAAAAGGATTTGTTGGCCAGGTGCAGTGGTTCATGCCTGTAATCCCAGCAGTTTGGGAGG
CTGAGGTGGGTGGATCACCTGAGGTCAGGAGTTCGAGACCAACCTGACCAACATGGTGAG
ACCCCCGTCTCTACTAAAAATAAAAAAAAAAATTAGCTGGGAGTGGTGGTGGGCACCTGT
AATCCTAGCTACTTGGGAGGCTGAACCAGGAGAATCTCTTGAACCTGGGAGGCAGAGGTT
GCAGTGAGCCGAGATCGTGCCATTGCACTCCAACCAGGGCAACAAGAGTGAAACTCCATC
TTAAAAAAAAAAAAAAAAGATTTGTTATGGGTTCCTTTTAAATGTGAACTTTTTTAGTG
TGTTTGTAATATGATCAAATTTAATAAATATTTATTTATGACTGTTAAAAAAAAAAAAA
AAAAAAAAAAAAAAAAAAAAAAAAAAAAA
```

FIG. 5

```
  1  MSPECARAAG DAPLRSLEQA NRTRFPFFSD VKGDHRLVLA AVETTVLVLI
 51  FAVSLLGNVC ALVLVARRRR RGATACLVLN LFCADLLFIS AIPLVLAVRW
101  TEAWLLGPVA CHLLFYVMTL SGSVTILTLA AVSLERMVCI VHLQRGVRGP
151  GRRARAVLLA LIWGYSAVAA LPLCVFFRVV PQRLPGADQE ISICTLIWPT
201  IPGEISWDVS FVTLNFLVPG LVIVISYSKI LQITKASRKR LTVSLAYSES
251  HQIRVSQQDF RLFRTLFLLM VSFFIMWSPI IITILLILIQ NFKQDLVIWP
301  SLFFWVVAFT FANSALNPIL YNMTLCRNEW KKIFCCFWFP EKGAILTDTS
351  VKRNDLSIIS G
```

FIG. 6A

```
ML1A_SHEEP   ~~~~~~~~~~~~~~~~~~~~~~~~~~~~~~MAGRLWGSPGGTPKGNGSS.ALLNVSQAAPGAGD
O46608       ~~~~~~~~~~~~~~~~~~~~~~~~~~~~~~MAGRLWGSPGGTPKGNGSS.ALLNVSQAAPGAGD
GALR_MOUSE   ~~~~~~~~~~~~~~~~~~~~~~~~~~~~~~~~~~MELAM.VNL.SEGNGSDPEPPAPE
GALR_RAT     ~~~~~~~~~~~~~~~~~~~~~~~~~~~~~~~~~~MELAP.VNL.SEGNGSDPEPPA.E
GALR_HUMAN   ~~~~~~~~~~~~~~~~~~~~~~~~~~~~~~~~~~MELAV.CNL.SEGNASCPEPPAPE
SSR5_MOUSE   ~~~~~~~~~~~~~~~~~~~~~~~~~MEPLSLASTPSWNASA.AGS.GSHNWSLVDPVS...
SSR5_RAT     ~~~~~~~~~~~~~~~~~~~~~~~~~MEPLSLASTPSWNASA.AGS.GNHNWSLVGSAS...
SSR3_MOUSE   ~~~~~~~~~~~~MATVTYPSSEPMTLDPGNTSST...WPLD..TTL.G..NTSAGASLT...
SSR3_RAT     ~~~~~~~~~~~MAAVTYPSSVPTTLDPGNASSA...WPLD..TSL.G..NASAGTSLA...
SSR3_HUMAN   ~~~~~~~~~~~~MDMLHPSSVSTTSEPENASSA...WPPD..ATL.G..NVSAGPSPA...
NY2R_MOUSE   MVLKMGPVGAEADENQTVEVKVEPYGP.GHTTPRGELPPDPEPEL.....IDSTKLV...
OX2R_HUMAN   ~~~~~~~~~~~~~~~MSGTKLEDSPPCRNWSSASELNETQEPFL.NPTDYDDEEFLRYL
HGPRBMY18    ~~~~~~~~~~~~~~~~~~~~~~~~~~~~~~~~MSPECARAAGDAPLRSLEQANRTRFPFFS

ML1A_SHEEP   GVRPRPSWLAATLASILIFTI.VVDIVGNLLVVLSVYRNK..KLRNAGNVFVVSLAVADL
O46608       GVRPRPSWLAATLASILIFTI.VVDIVGNLLVVLSVYRNK..KLRNAGNVFVVSLAVADL
GALR_MOUSE   SRPLFGIGVENFITLVVFGLIFAMGVLGNSLVITVLARSKPGKPRSTTNLFILNLSIADL
GALR_RAT     PRPLFGIGVENFITLVVFGLIFAMGVLGNSLVITVLARSKPGKPRSTTNLFILNLSIADL
GALR_HUMAN   PGPLFGIGVENFVTLVVFGLIFALGVLGNSLVITVLARSKPGKPRSTTNLFILNLSIADL
SSR5_MOUSE   .....PMGARAVLVPVLYLLVCTVGLGGNTLVIYVVLRYA..KMKTVTNVYILNLAVADV
SSR5_RAT     .....PMGARAVLVPVLYLLVCTVGLSGNTLVIYVVLRHA..KMKTVTNVYILNLAVADV
SSR3_MOUSE   .....GLAVSGILISLVYLVVCVVGLLGNSLVIYVVLRHT..SSPSVTSVYILNLALADE
SSR3_RAT     .....GLAVSGILISLVYLVVCVVGLLGNSLVIYVVLRHT..SSPSVTSVYILNLALADE
SSR3_HUMAN   .....GLAVSGVLIPLVYLVVCVVGLLGNSLVIYVVLRHT..ASPSVTNVYILNLALADE
NY2R_MOUSE   ........EVQVILILAYCSIILLGVWGNSLVIHVVIKFK..SMRTVTNFFIANLAVADL
OX2R_HUMAN   WREYLHPKEYEWVLIAGYILVFVVALIGNVLVCVAVWKNH..HMRTVTNYFIVNLSLADV
HGPRBMY18    DVKGDHRLVLAAVETTVLVLIFAVSLLGNVCALVLVARRRR...RGATACLVLNLFCADL

ML1A_SHEEP   LVAVYPYP.LALASIVNNGWSLSSLHCQLSGFLMGLSVIGSVFSLTGIAINRYCCICHSL
O46608       LVAVYPYP.LALASIVNNGWSLSSLHCQLSGFLMGLSVIGSVFSLTGIAINRYCCICHSL
GALR_MOUSE   AYLLFCIPFQATVYA.LPTWVLGAFICKFIHYFFTVSMLVSIFTLAAMSVDRYVAIVHSR
GALR_RAT     AYLLFCIPFQATVYA.LPTWVLGAFICKFIHYFFTVSMLVSIFTLAAMSVDRYVAIVHSR
GALR_HUMAN   AYLLFCIPFQATVYA.LPTWVLGAFICKFIHYFFTVSMLVSIFTLAAMSVDRYVAIVHSR
SSR5_MOUSE   LFML.GLPFLATQNA.VSYWPFGSFLCRLVMTLDGINQFTSIFCLMVMSVDRYLAVVHPL
SSR5_RAT     LFML.GLPFLATQNAVVSYWPFGSFLCRLVMTLDGINQFTSIFCLMVMSVDRYLAVVHPL
SSR3_MOUSE   LFML.GLPFLAAQNA.LSYWPFGSLMCRLVMAVDGINQFTSIFCLTVMSVDRYLAVVHPT
SSR3_RAT     LFML.GLPFLAAQNA.LSYWPFGSLMCRLVMAVDGINQFTSIFCLTVMSVDRYLAVVHPT
SSR3_HUMAN   LFML.GLPFLAAQNA.LSYWPFGSLMCRLVMAVDGINQFTSIFCLTVMSVDRYLAVVHPT
NY2R_MOUSE   LVNTLCLPFTLTYT.LMGEWKMGPVLCHLVPYAQGLAVQVSTITLTVIALDRHRCIVYHL
OX2R_HUMAN   LVTITCLPATLVVD.ITETWFFGQSLCKVIPYLQTVSVSVSVLTLSCIALDRWYAICHPL
HGPRBMY18    LF.ISAIPLVLAVR.WTEAWLLGPVACHLLFYVMTLSGSVTILTLAAVSLERMVCIVHLQ

ML1A_SHEEP   RYGKLYSGTNSLCYVFLIWTLTLVAIVPNLCVGTLQYDPRIYS...........CTFTQS
O46608       RYGKLYSGTNSLCYVFLIWTLTLVAIVPNLCVGTLQYDPRIYS...........CTFTQS
GALR_MOUSE   RSSSLRVSRNALLGVGFIWALSIAMASP.VAYHQR.....LFH.RDSNQIF...CWEQWP
GALR_RAT     RSSSLRVSRNALLGVGFIWALSIAMASP.VAYYQR.....LFH.RDSNQIF...CWEHWP
GALR_HUMAN   RSSSLRVSRNALLGVGCIWALSIAMASP.VAYHQG.....LFHPRASNQLF...CWEQWP
SSR5_MOUSE   RSARWRRPRVAKLASAAVWFSLLMSLP.LL.........VFADVQEGWGT...CNLSWP
SSR5_RAT     RSARWRRPRVAKMASAAVWFSLLMSLP.LL.........VFADVQEGWGT...CNLSWP
SSR3_MOUSE   RSARWRTAPVARTVSRAVWVASAVVVLP.VV.........VFSGVPRGMST...CHMQWP
SSR3_RAT     RSARWRTAPVARMVSAAVWVASAVVVLP.VV.........VFSGVPRGMST...CHMQWP
SSR3_HUMAN   RSARWRTAPVARTVSAAVWVASAVVVLP.VV.........VFSGVPRGMST...CHMQWP
NY2R_MOUSE   ESK.I.SKRISFLITGLAWGISALLASP.LAIFREYSLIEIIPDFE.....IVACTEKWP
OX2R_HUMAN   MFKST.AKRARNSIV.ITWIVSCLLMIP.QAIVMECS..TVFPGLANKTTLFTVCDERWG
HGPRBMY18    RGVRGPGRRARAVLLALIWGYSAVAALP.LCVFFRVVPQRL....PGADQEISICTLIWP
```

FIG. 6B

```
ML1A_SHEEP   VS......SAYTIAVVVFHFIVPMLVVVFCYLRIWALV......................L
O46608       VS......SAYTIAVVVFHFIVPMLVVVFCYLRIWALV......................L
GALR_MOUSE   .NK..LHKKAYVVCTFVFGYLLPLLLICFCYAKVLNHL............H...KKLKNM
GALR_RAT     .NQ..LHKKAYVVCTFVFGYLLPLLLICFCYAKVLNHL............H...KKLKNM
GALR_HUMAN   .DP..RHKKAYVVCTFVFGYLLPLLLICFCYAKVLNHL............H...KKLKNM
SSR5_MOUSE   .EPVGLWGAAFITYTSVLGFFGPLLVICLCYLLIVVKV............KAAGMRVGS.
SSR5_RAT     .EPVGLWGAAFITYTSVLGFFGPLLVICLCYLLIVVKV............KAAGMRVGS.
SSR3_MOUSE   .EPAAAWRTAFIIYMAALGFFGPLLVICLCYLLIVVKV............RSTTRRVRAP
SSR3_RAT     .EPAAAWRTAFIIYTAALGFFGPLLVICLCYLLIVVKV............RSTTRRVRAP
SSR3_HUMAN   .EPAAAWRAGFLIYTAALGFFGPLLVICLCYLLIVVKV............RSAGRRV...
NY2R_MOUSE   GBEKSVYGTVYSLSTLLILYVLPLGIISFSYTRIWSKL............R.....NHV
OX2R_HUMAN   GE...LYPKMYHLCFFLVTYMAPLCLMVLAYLQIFRKLWCRQIPGTSSVVQRKWKPLQPV
HGPRBMY18    TIPGEL...SWDVSFVTLNFLVPGLVIVISYSKLLQITKASRKRLTVSLAYSESHQLR..

ML1A_SHEEP   QVRWKVKPDNKPKLKPQDFRNFV.........TMFVVFVLFAICWAPLNFIGLVVASDPA
O46608       QVRWKVKPDNKPKLKPQDFRNFV.........TMFVVFVLFAICWAPLNFIGLVVASDPD
GALR_MOUSE   S........KKSE..........ASKKKTAQTVLVVVVVFGISWLPHHVVHLWAEFGAF
GALR_RAT     S........KKSE..........ASKKKTAQTVLVVVVVFGISWLPHHVIHLWAEFGAF
GALR_HUMAN   S........KKSE..........ASKKKTAQTVLVVVVVFGISWLPHHIIHLWAEFGVF
SSR5_MOUSE   ..........SRRR.........RSERKVTRMVVVVLVFVGCWLPFFIVNIVNLAFTL
SSR5_RAT     ..........SRRR.........RSEPKVTRMVVVVLVFVGCWLPFFIVNIVNLAFTL
SSR3_MOUSE   SCQWVQAPACQRRR.........RSERRVTRMVVAVVALFVLCWMPFYLLNIVNVVCPL
SSR3_RAT     SCQWVQAPACQRRR.........RSERRVTRMVVAVVALFVLCWMPFYLLNIVNVVCPL
SSR3_HUMAN   ...W..APSCQRRR.........RSERRVTRMVVAVVALFVLCWMPFYVLNIVNVVCPL
NY2R_MOUSE   S....PG.........AASDHYHQRRHKMTKMLVCVVVVFAVSWLP...LHAFQLAVDI
OX2R_HUMAN   SQPRGPGQPTKSRMSAVAAEIKQIRARRKTARMLMVVLLVFAICYLPISILNVLKRVFGM
HGPRBMY18    ..................VSQQDFRLFRTLFLLMVSFFIMWSPIILTILLILIQNF

ML1A_SHEEP   SMAPRIPE....WLFVASYYMAYFNSCLNAIIYGLLNQNFRQEYRKIIVS....LCTTKM
O46608       SMAPRIPE....WLFVASYYMAYFNSCLNAIIYGLLNQNFRQEYRKIIVS....LCTTKM
GALR_MOUSE   ...PLTPASF..FFRITAHCLAYSNSSVNPIIYAFLSENFRKAYKQVFKC....HVCDES
GALR_RAT     ...PLTPASF..EFRITAHCLAYSNSSVNPIIYAFLSENFRKAYKQVFKC....RVCNES
GALR_HUMAN   ...PLTPASF..LFRITAHCLAYSNSSVNPIIYAFLSENFRKAYKQVFKC....HIRKDS
SSR5_MOUSE   ...PEEPTSAGLYFFVVV..LSYANSCANPLLYGFLSDNFRQSFRKALCL....RRGYGV
SSR5_RAT     ...PEEPTSAGLYFFVVV..LSYANSCANPLLYGFLSDNFRQSFRKVLCL....RRGYGM
SSR3_MOUSE   ...PEEPAFFGLYFLVVA..LPYANSCANPILYGFLSYRFKQGFRRIL.L....RPSRRI
SSR3_RAT     ...PEEPAFFGLYFLVVA..LPYANSCANPILYGFLSYRFKQGFRRIL.L....RPSRRV
SSR3_HUMAN   ...PEEPAFFGLYFLVVA..LPYANSCANPILYGFLSYRFKQGFRRVL.L....RPSRRV
NY2R_MOUSE   DSHVLDLKEYKLIFTV.FHIIAMCSTFANPLLYGWMNSNYRKAFLSAFRC....EQRLDA
OX2R_HUMAN   FAHTEDRETVYAWFTF.SHWLVYANSAANPIIYNFLSGKFREEFKAAFSC.....CCLGV
HGPRBMY18    KQDLVIWPS..LFFWVAF..TFANSALNPILYNMTL...CRNEWKKIFCCFWFPEKGAIL

ML1A_SHEEP   FFVDSSNHVADRIKRKPSPLIANHNLIKVDSV~~~~~~~~~~~~~~~~~~~~~~~~~~~~
O46608       FFVDSSNHVADRIKRKPSPLIANRNLVKVDSV~~~~~~~~~~~~~~~~~~~~~~~~~~~~
GALR_MOUSE   PRSETKEN.KSRMDTPPSTNCTHV~~~~~~~~~~~~~~~~~~~~~~~~~~~~~~~~~~~~
GALR_RAT     PHGDAKE..KNRIDTPPSTNCTHV~~~~~~~~~~~~~~~~~~~~~~~~~~~~~~~~~~~~
GALR_HUMAN   HLSDTKEN.KSRIDTPPSTNCTHV~~~~~~~~~~~~~~~~~~~~~~~~~~~~~~~~~~~~
SSR5_MOUSE   EDADAIEP.RPDKSGRPQTTLPTRSCEANGLMQTSRL~~~~~~~~~~~~~~~~~~~~~~~
SSR5_RAT     EDADAIEP.RPDKSGRPQATLPTRSCEANGLMQTSRI~~~~~~~~~~~~~~~~~~~~~~~
SSR3_MOUSE   RSQ...EP....GSGPPEKTEEEEDEEEEERREEEEERRMQRGQEMNGRLSQIAQAGTSGQ
SSR3_RAT     RSQ...EP....GSGPPEKTEEEEDEEEEERREEEEERRMQRGQEMNGRLSQIAQPGPSGQ
SSR3_HUMAN   RSQ...EP....TVGPPEKT.EEEDEEEED..GEESREGGKGKEMNGRVSQITQPGTSGQ
NY2R_MOUSE   IHSEVSMT.FKAKKNLEVKKNNGPTDSFSEATNV~~~~~~~~~~~~~~~~~~~~~~~~~~
OX2R_HUMAN   HHRQEDRL.TRGRTSTESRKS..LTTQISNFDNISKLSEQVVLTSISTLPAANGAGPLQN
HGPRBMY18    TDTSVKRNDLSIISG*~~~~~~~~~~~~~~~~~~~~~~~~~~~~~~~~~~~~~~~~~~~~
```

FIG. 6C

```
ML1A_SHEEP   ~~~~~~~~~~~~~~~~~~~~~~~~~~~~~~~~
O46608       ~~~~~~~~~~~~~~~~~~~~~~~~~~~~~~~~
GALR_MOUSE   ~~~~~~~~~~~~~~~~~~~~~~~~~~~~~~~~
GALR_RAT     ~~~~~~~~~~~~~~~~~~~~~~~~~~~~~~~~
GALR_HUMAN   ~~~~~~~~~~~~~~~~~~~~~~~~~~~~~~~~
SSR5_MOUSE   ~~~~~~~~~~~~~~~~~~~~~~~~~~~~~~~~
SSR5_RAT     ~~~~~~~~~~~~~~~~~~~~~~~~~~~~~~~~
SSR3_MOUSE   QPRPCTGTAKEQQLLPQEATAGDKAST..LSHL
SSR3_RAT     QQRPCTGTAKEQQLLPQEATAGDKAST..LSHL
SSR3_HUMAN   ERPPSRVASKEQQLLPQEASTGEKSSTMRISYL
NY2R_MOUSE   ~~~~~~~~~~~~~~~~~~~~~~~~~~~~~~~~
OX2R_HUMAN   W~~~~~~~~~~~~~~~~~~~~~~~~~~~~~~~
HGPRBMY18    ~~~~~~~~~~~~~~~~~~~~~~~~~~~~~~~~
```

МETHODS OF DIAGNOSING RENAL TUMORS BY DETERMINING THE EXPRESSION LEVEL OF RNA ENCODING THE HGPRBMY18 POLYPEPTIDE

This application is a continuation-in-part application of non-provisional application U.S. Ser. No. 10/262,313, filed Sep. 30, 2002 now abandoned; which is a continuation-in-part application of non-provisional application U.S. Ser. No. 09/992,331, filed Nov. 14, 2001 now abandoned, which claims benefit to provisional application U.S. Ser. No. 60/261,782, filed Jan. 16, 2001; to provisional application U.S. Ser. No. 60/308,540, filed Jul. 27, 2001; and to provisional application U.S. Ser. No. 60/248,483, filed Nov. 14, 2000.

FIELD OF THE INVENTION

The present invention relates to the fields of pharmacogenomics, diagnostics and patient therapy. More specifically, the present invention relates to methods of diagnosing and/or treating diseases involving the Human G-Protein Coupled Receptor, HGPRBMY18.

BACKGROUND OF THE INVENTION

It is well established that many medically significant biological processes are mediated by proteins participating in signal transduction pathways that involve G-proteins and/or second messengers, e.g., cAMP (Lefkowitz, *Nature*, 351:353–354(1991)). Herein these proteins are referred to as proteins participating in pathways with G-proteins or PPG proteins. Some examples of these proteins include the GPC receptors, such as those for adrenergic agents and dopamine (Kobilka, B. K., et al., *PNAS*, 84:46–50 (1987); Kobilka, B. K., et al., *Science*, 238:650–656 (1987); Bunzow, J. R., et al., *Nature*, 336:783–787 (1988)), G-proteins themselves, effector proteins, e.g., phospholipase C, adenylate cyclase, and phosphodiesterase, and actuator proteins, e.g., protein kinase A and protein kinase C (Simon, M. I., et al., *Science*, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors, which bind to neuroleptic drugs, used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant, cytomegalovirus receptors, etc.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxyl terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise a hydrophilic socket formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand-binding site. TM3 has been implicated in several G-protein coupled receptors as having a ligand-binding site, such as including the TM3 aspartate residue. Additionally, TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., *Endoc. Rev.*, 10:317–331(1989)). Different G-protein β-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

G-protein coupled receptors (GPCRs) are one of the largest receptor superfamilies known. These receptors are biologically important and malfunction of these receptors results in diseases such as Alzheimer's, Parkinson, diabetes, dwarfism, color blindness, retinal pigmentosa and asthma. GPCRs are also involved in depression, schizophrenia, sleeplessness, hypertension, anxiety, stress, renal failure and in several other cardiovascular, metabolic, neural, oncology and immune disorders (F. Horn and G. Vriend, *J. Mol. Med.*, 76: 464–468 (1998)). They have also been shown to play a role in HIV infection (Y. Feng et al., *Science*, 272: 872–877 (1996)). The structure of GPCRs consists of seven transmembrane helices that are connected by loops. The N-terminus is always extracellular and C-terminus is intracellular. GPCRs are involved in signal transduction. The signal is received at the extracellular N-terminus side. The signal can be an endogenous ligand, a chemical moiety or light. This signal is then transduced through the membrane to the cytosolic side where a heterotrimeric protein G-protein is activated which in turn elicits a response (F. Horn et al.,

*Recept. and Chann.*, 5: 305–314 (1998)). Ligands, agonists and antagonists, for these GPCRs are used for therapeutic purposes.

The present invention provides a newly discovered G-protein coupled receptor protein, which may be involved in cellular growth properties of the pituitary gland, based on its abundance in this tissue. Furthermore, the G-protein coupled receptor protein of the invention may be involved in other tissues, such as, but not limited to colon, breast, lung, and prostate. The present invention also relates to newly identified polynucleotides, polypeptides encoded by such polynucleotides, the use of such polynucleotides and polypeptides, as well as the production of such polynucleotides and polypeptides. More particularly, the polypeptides of the present invention are human 7-transmembrane receptors. The invention also relates to inhibiting the action of such polypeptides.

SUMMARY OF THE INVENTION

The present invention provides a novel human member of the G-protein coupled receptor (GPCR) family (HGPRBMY18). Based on sequence homology, the protein HGPRBMY18 is a candidate GPCR. Based on its protein sequence information, the HGPRBMY18 contains seven transmembrane domains which is a characteristic structural feature of GPCRs. The GPCR of the present invention is closely related to the galanin, somatostatin, orexin, and meletonin receptors based on sequence similarity using the BLAST program. This orphan GPCR is expressed highly in pituitary gland and colon, and moderately in breast, lung, and prostate. Moreover, this orphan GPCR is also differentially expressed in renal tumors relative to matched normal renal tissue.

It is an object of the present invention to provide an isolated HGPRBMY18 polynucleotide as depicted in SEQ ID NO:1.

It is also an object of the present invention to provide the HGPRBMY18 polypeptide, encoded by the polynucleotide of SEQ ID NO:1 (CDS=1 to 1083) and having the amino acid sequence of SEQ ID NO:2, or a functional or biologically active portion thereof.

It is a further object of the present invention to provide compositions comprising the HGPRBMY18 polynucleotide sequence, or a fragment thereof, or the encoded HGPRBMY18 polypeptide (MW=40.5 Kd), or a fragment or portion thereof. Also provided by the present invention are pharmaceutical compositions comprising at least one HGPRBMY18 polypeptide, or a functional portion thereof, wherein the compositions further comprise a pharmaceutically acceptable carrier, excipient, or diluent.

It is an object of the invention to provide a novel isolated and substantially purified polynucleotide that encodes the HGPRBMY18 GPCR homologue. In a particular aspect, the polynucleotide comprises the nucleotide sequence of SEQ ID NO:1. It is also an object of the present invention to provide a polynucleotide sequence comprising the complement of SEQ ID NO:1, or variants thereof. In addition, the present invention features polynucleotide sequences, which hybridize under conditions of moderate stringency or high stringency to the polynucleotide sequence of SEQ ID NO:1.

It is an object of the present invention to further provide a nucleic acid sequence encoding the HGPRBMY18 polypeptide and an antisense of the nucleic acid sequence, as well as oligonucleotides, fragments, or portions of the nucleic acid molecule or antisense molecule. Also provided are expression vectors and host cells comprising polynucleotides that encode the HGPRBMY18 polypeptide.

It is an object of the present invention to provide methods for producing a polypeptide comprising the amino acid sequence depicted in SEQ ID NO:2, or a fragment thereof, comprising the steps of a) cultivating a host cell containing an expression vector containing at least a functional fragment of the polynucleotide sequence encoding the HGPRBMY18 protein according to this invention under conditions suitable for the expression of the encoded polypeptide; and b) recovering the polypeptide from the host cell.

It is also an object of the invention to provide antibodies, and binding fragments thereof, which bind specifically to the HGPRBMY18 polypeptide, or an epitope thereof, for use as therapeutic and diagnostic agents.

It is a further object of the present invention to provide methods for screening for agents which bind to, or modulate HGPRBMY18 polypeptide, e.g., agonists and antagonists, as well as the binding molecules, and/or modulators, e.g., agonists and antagonists, particularly those that are obtained from the screening methods described.

It is an object of the present invention to provide a substantially purified antagonist or inhibitor of the polypeptide of SEQ ID NO:2. In this regard, and by way of example, a purified antibody that binds to a polypeptide comprising the amino acid sequence of SEQ ID NO:2 is provided.

It is also a further object of the present invention to provide substantially purified agonists or activators of the polypeptide of SEQ ID NO:2 are further provided.

It is an object of the present invention to provide HGPRBMY18 nucleic acid sequences, polypeptide, peptides and antibodies for use in the diagnosis and/or screening of disorders or diseases associated with expression of the polynucleotide and its encoded polypeptide as described herein.

It is a further object of the present invention to provide kits for screening and diagnosis of disorders associated with aberrant or uncontrolled cellular development and with the expression of the polynucleotide and its encoded polypeptide as described herein.

It is also an object of the present invention to provide methods for the treatment or prevention of pituitary gland disorders, endocrinal diseases, and growth disorders, in addition to cancers, immune disorders, renal disorders, and neurological disorders involving administering to an individual in need of treatment or prevention an effective amount of a purified antagonist of the HGPRBMY18 polypeptide. Due to its elevated expression in pituitary gland, the novel GPCR protein of the present invention is particularly useful in treating or preventing pituitary gland disorders, conditions, or diseases. Additionally, HGPRBMY18 may be used in treating or preventing several other diseases, conditions, or disorders, such as, but not limited to, kidney, colon, breast, lung and prostate, particularly cancers.

It is an object of the present invention to also provide a method for detecting a polynucleotide that encodes the HGPRBMY18 polypeptide, or homologue thereof, in a biological sample comprising the steps of: a) hybridizing the complement of the polynucleotide sequence encoding SEQ ID NO:2 to a nucleic acid material of a biological sample, thereby forming a hybridization complex; and b) detecting the hybridization complex, wherein the presence of the complex correlates with the presence of a polynucleotide encoding the HGPRBMY18 polypeptide in the biological sample. The nucleic acid material may be further amplified by the polymerase chain reaction prior to hybridization.

One aspect of the instant invention comprises methods and compositions to detect and diagnose alterations in the HGPRBMY18 sequence in tissues and cells as they relate to ligand response.

It is an object of the present invention to further provide compositions for diagnosing pituitary gland-, colon-, breast-, lung-, kidney-, and prostate-related disorders and for diagnosing or monitoring response to HGPRBMY18 therapy in humans. In accordance with the invention, the compositions detect an alteration of the normal or wild type HGPRBMY18 sequence or its expression product in a patient sample of cells or tissue.

It is also an object of the present invention to provide diagnostic probes for diseases and a patient's response to therapy. The probe sequence comprises the HGPRBMY18 locus polymorphism, as described herein. The probes can be constructed of nucleic acids or amino acids.

It is a further object of the present invention to provide antibodies that recognize and bind to the HGPRBMY18 protein and immunoreactive portions thereof. Such antibodies can be either polyclonal or monoclonal. Antibodies that bind to the HGPRBMY18 protein can be utilized in a variety of diagnostic and prognostic formats and therapeutic methods.

It is an object of the invention to also provide diagnostic kits for the determination of the nucleotide sequence of human HGPRBMY18 alleles. The kits are based on amplification-based assays, nucleic acid probe assays, protein nucleic acid probe assays, antibody assays or any combination thereof.

It is an object of the instant invention to also provide methods for detecting genetic predisposition, susceptibility and response to therapy related to the pituitary gland, colon, breast, lung, kidney, and prostate. In accordance with the invention, the method comprises isolating a human sample, for example, blood or tissue from adults, children, embryos or fetuses, and detecting at least one alteration in the wild type HGPRBMY18 sequence, or its expression product, from the sample, wherein the alterations are indicative of genetic predisposition, susceptibility or altered response to therapy related to the pituitary gland, colon, breast, lung, kidney, and prostate.

It is a further object of the present invention to further provide methods for making determinations as to which drug to administer, dosages, duration of treatment and the like.

The invention further relates to a method for preventing, treating, or ameliorating a medical condition with the polypeptide provided as SEQ ID NO:2, in addition to, its encoding nucleic acid, or a modulator thereof, wherein the medical condition is a disorder of the pituitary gland, a disorder of the lower GI, hyperprolactinemia, colorectal cancers of various origins as well as cancers in other tissues where receptors may be expressed albeit at low levels, endocrine diseases and/or disorders, which include, but are not limited to, the following: aberrant growth hormone synthesis and/or secretion, aberrant prolactin synthesis and/or secretion, aberrant luteinizing hormone synthesis and/or secretion, aberrant follicle-stimulating hormone synthesis and/or secretion, aberrant thyroid-stimulating hormone synthesis and/or secretion, aberrant adrenocorticotropin synthesis and/or secretion, aberrant vasopressin secretion, aberrant oxytocin secretion, aberrant growth, aberrant lactation, aberrant sexual characteristic development, aberrant testosterone synthesis and/or secretion, aberrant estrogen synthesis and/or secretion, aberrant water homeostasis, hypogonadism, Addison's disease, hypothyroidism, Cushing's disease, agromegaly, gigantism, lethargy, osteoporosis, aberrant calcium homeostasis, aberrant potassium homeostasis, reproductive disorders, pulmonary disorders, lung metastasis, lung cancer, renal disorders, kidney tumors, and developmental disorders.

The invention further relates to a method of diagnosing a pathological condition or a susceptibility to a pathological condition in a subject comprising the steps of (a) determining the presence or amount of expression of the polypeptide of SEQ ID NO:2 in a biological sample; (b) and diagnosing a pathological condition or a susceptibility to a pathological condition based on the presence or amount of expression of the polypeptide relative to a control, wherein said condition is a member of the group consisting of colon cancer, or related proliferative condition of the colon, lung cancer, or related proliferative condition of the lung, kidney cancer, or related proliferative condition of the kidney, or other disorder discussed herein.

Further objects, features, and advantages of the present invention will be better understood upon a reading of the detailed description of the invention when considered in connection with the accompanying figures/drawings.

BRIEF DESCRIPTION OF THE FIGURES

FIG. 1 shows the full-length nucleotide sequence of cDNA clone HGPRBMY18, a human G-protein coupled receptor (SEQ ID NO:1).

FIG. 2 shows the amino acid sequence (SEQ ID NO:2) from the translation of the full-length HGPRBMY18 cDNA sequence.

FIG. 3 shows the 5' untranslated sequence of the orphan HGPRBMY18 (SEQ ID NO:3).

FIG. 4 shows the 3' untranslated sequence of the orphan HGPRBMY18 (SEQ ID NO:4).

FIG. 5 shows the predicted transmembrane region of the HGPRBMY18 protein where the predicted transmembrane regions, represented by bold-faced and underlined type, correspond to the peaks with scores above 1500.

FIGS. 6A–6C show the multiple sequence alignment of the translated sequence of the orphan G-protein coupled receptor, HGPRBMY18, where the GCG pileup program was used to generate the alignment with galanin, somatostatin, orexin, and melatonin receptor sequences. The blackened areas represent identical amino acids in more than half of the listed sequences and the grey highlighted areas represent similar amino acids. As shown in FIGS. 6A–6B, the sequences are aligned according to their amino acids, where: HGPRBMY18 (SEQ ID NO:2) is encoded by full length HGPRBMY18 cDNA; ML1A_SHEEP (SEQ ID NO:8) represents the sheep form of the melatonin receptor 1A; O46608 (SEQ ID NO:9) is the sheep form of melatonin receptor; GALR_MOUSE (SEQ ID NO:10) is the mouse form of the galanin receptor; GALR_RAT (SEQ ID NO:11) is the rat form of the galanin receptor; GALR_HUMAN (SEQ ID NO:12) represents the human form of the galanin receptor; SSR5_MOUSE (SEQ ID NO:13) is the mouse form of the somatostatin receptor 5; SSR5_RAT (SEQ ID NO:14) is the rat form of the somatostatin receptor 5; SSR3_MOUSE (SEQ ID NO:15) represents the mouse form of the somatostatin receptor 3; and SSR3_RAT (SEQ ID NO:16) is the rat form of the somatostatin receptor 3; SSR3_HUMAN (SEQ ID NO:17) represents the human form of the somatostatin receptor 3; NY2R_MOUSE (SEQ ID NO:18) represents the mouse form of the Neuropeptide Y receptor 2; and OX2R_HUMAN (SEQ ID NO:19) is the human form of the orexin receptor 2.

DETAILED DESCRIPTION OF THE PRESENT INVENTION

Figure 7:
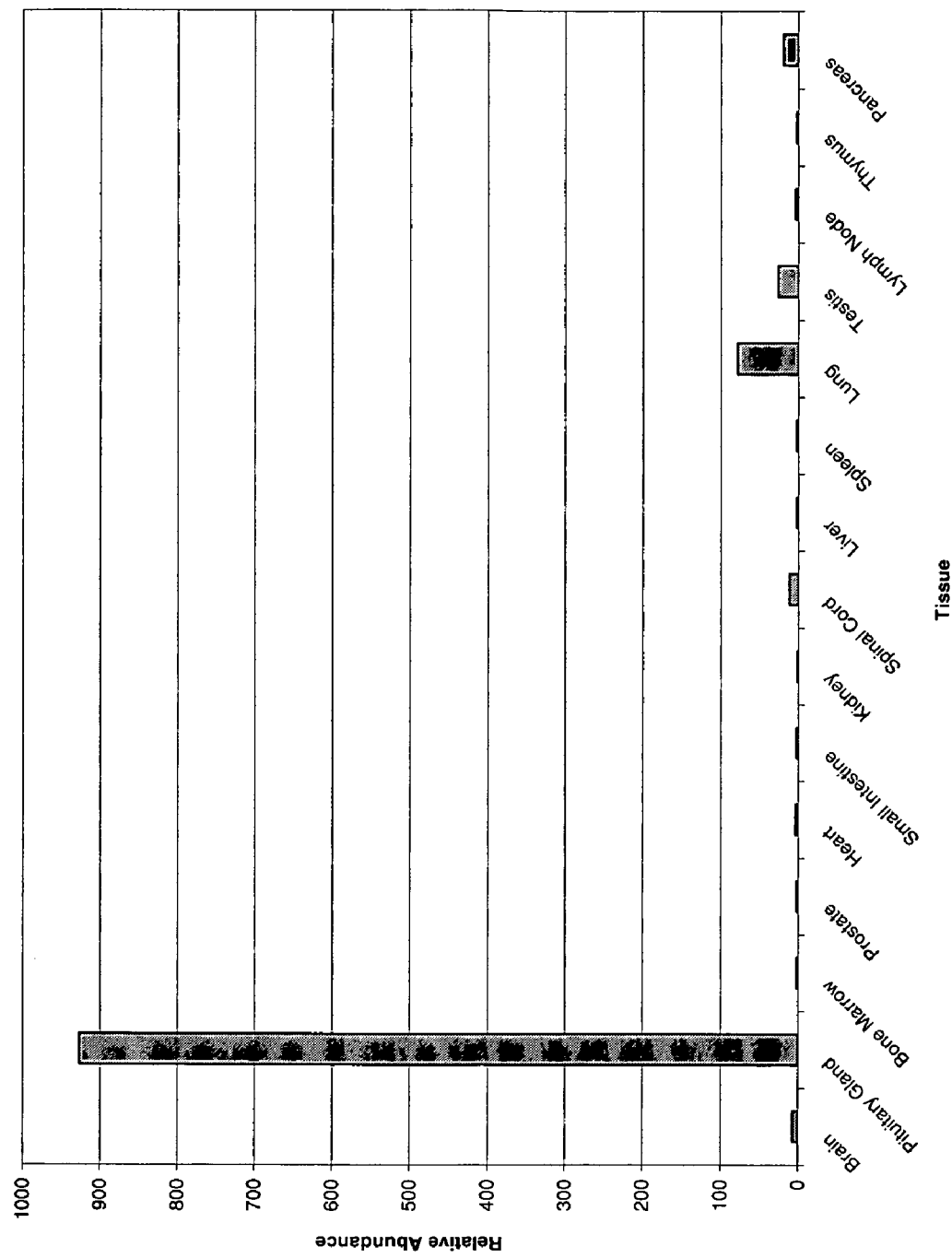
FIG. 7 shows an expression profile of the novel human orphan GPCR, HGPRBMY18, in various tissues as described in Examples 3 and 4. An index listing the tissue of origin of each mRNA referenced on the X-axis is provided in Table 1.

The present invention provides a novel isolated polynucleotide and encoded polypeptide, the expression of which is high in pituitary gland and colon. HGPRBMY18 is also sporadically expressed in breast, lung, and prostate. Moreover, HGPRBMY18 is differentially expressed in renal tumor tissues relative to matched normal renal tissue. This novel polypeptide is termed herein HGPRBMY18, an acronym for "Human G-Protein coupled Receptor BMY18". HGPRBMY18 is also referred to as GPCR38-2.

Definitions

The HGPRBMY18 polypeptide (or protein) refers to the amino acid sequence of substantially purified HGPRBMY18, which may be obtained from any species, preferably mammalian, and more preferably, human, and from a variety of sources, including natural, synthetic, semi-synthetic, or recombinant. Functional fragments of the HGPRBMY18 polypeptide are also embraced by the present invention.

An "agonist" refers to a molecule which, when bound to the HGPRBMY18 polypeptide, or a functional fragment thereof, increases or prolongs the duration of the effect of the HGPRBMY18 polypeptide. Agonists may include proteins, nucleic acids, carbohydrates, or any other molecules that bind to and modulate the effect of HGPRBMY18 polypeptide. An antagonist refers to a molecule which, when bound to the HGPRBMY18 polypeptide, or a functional fragment thereof, decreases the amount or duration of the biological or immunological activity of HGPRBMY18 polypeptide. "Antagonists" may include proteins, nucleic acids, carbohydrates, antibodies, or any other molecules that decrease or reduce the effect of HGPRBMY18 polypeptide.

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or anti-sense strand. By way of non-limiting example, fragments include nucleic acid sequences that are greater than 20–60 nucleotides in length, and preferably include fragments that are at least 70–100 nucleotides, or which are at least 1000 nucleotides or greater in length.

Similarly, "amino acid sequence" as used herein refers to an oligopeptide, peptide, polypeptide, or protein sequence, and fragments or portions thereof, and to naturally occurring or synthetic molecules. Amino acid sequence fragments are typically from about 5 to about 30, preferably from about 5 to about 15 amino acids in length and retain the biological activity or function of the HGPRBMY18 polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. In addition, the terms HGPRBMY18 polypeptide and HGPRBMY18 protein are used interchangeably herein to refer to the encoded product of the HGPRBMY18 nucleic acid sequence of the present invention.

It is another aspect of the present invention to provide modulators of the HGPRBMY18 protein and HGPRBMY18 peptide targets which can affect the function or activity of HGPRBMY18 in a cell in which HGPRBMY18 function or activity is to be modulated or affected. In addition, modulators of HGPRBMY18 can affect downstream systems and molecules that are regulated by, or which interact with, HGPRBMY18 in the cell. Modulators of HGPRBMY18 include compounds, materials, agents, drugs, and the like, that antagonize, inhibit, reduce, block, suppress, diminish, decrease, or eliminate HGPRBMY18 function and/or activity. Such compounds, materials, agents, drugs and the like can be collectively termed "antagonists". Alternatively, modulators of HGPRBMY18 include compounds, materials, agents, drugs, and the like, that agonize, enhance, increase, augment, or amplify HGPRBMY18 function in a cell. Such compounds, materials, agents, drugs and the like can be collectively termed "agonists".

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

A "variant" of the HGPRBMY18 polypeptide refers to an amino acid sequence that is altered by one or more amino acids. The variant may have "conservative" changes, wherein a substituted amino acid has similar structural or chemical properties, e.g., replacement of leucine with isoleucine. More rarely, a variant may have "non-conservative" changes, e.g., replacement of a glycine with a tryptophan. Minor variations may also include amino acid deletions or insertions, or both. Guidance in determining which amino acid residues may be substituted, inserted, or deleted without abolishing functional biological or immunological activity may be found using computer programs well known in the art, for example, DNASTAR software.

An "allele" or "allelic sequence" is an alternative form of the HGPRBMY18 nucleic acid sequence. Alleles may result from at least one mutation in the nucleic acid sequence and may yield altered mRNAs or polypeptides whose structure or function may or may not be altered. Any given gene, whether natural or recombinant, may have none, one, or many allelic forms. Common mutational changes, which give rise to alleles, are generally ascribed to natural deletions, additions, or substitutions of nucleotides. Each of these types of changes may occur alone, or in combination with the others, one or more times in a given sequence.

"Altered" nucleic acid sequences encoding HGPRBMY18 polypeptide include nucleic acid sequences containing deletions, insertions and/or substitutions of different nucleotides resulting in a polynucleotide that encodes the same or a functionally equivalent HGPRBMY18 polypeptide. Altered nucleic acid sequences may further include polymorphisms of the polynucleotide encoding the HGPRBMY18 polypeptide; such polymorphisms may or may not be readily detectable using a particular oligonucleotide probe. The encoded protein may also contain deletions, insertions, or substitutions of amino acid residues, which produce a silent change and result in a functionally equivalent HGPRBMY18 protein. Deliberate amino acid substitutions may be made on the basis of similarity in polarity, charge, solubility, hydrophobicity, hydrophilicity, and/or the amphipathic nature of the residues, as long as the biological activity of HGPRBMY18 protein is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; and phenylalanine and tyrosine.

"Peptide nucleic acid" (PNA) refers to an antisense molecule or anti-gene agent which comprises an oligonucleotide ("oligo") linked via an amide bond, similar to the peptide backbone of amino acid residues. PNAs typically comprise oligos of at least 5 nucleotides linked via amide bonds. PNAs may or may not terminate in positively charged amino acid residues to enhance binding affinities to DNA. Such amino acids include, for example, lysine and arginine, among others. These small molecules stop transcript elongation by binding to their complementary strand of nucleic acid (P. E. Nielsen et al., 1993, *Anticancer Drug Des.*, 8:53–63). PNA may be pegylated to extend their lifespan in the cell where they preferentially bind to complementary single stranded DNA and RNA.

"Oligonucleotides" or "oligomers" refer to a nucleic acid sequence, preferably comprising contiguous nucleotides, of at least about 6 nucleotides to about 60 nucleotides, preferably at least about 8 to 10 nucleotides in length, more preferably at least about 12 nucleotides in length e.g., about 15 to 35 nucleotides, or about 15 to 25 nucleotides, or about 20 to 35 nucleotides, which can be typically used in PCR amplification assays, hybridization assays, or in microarrays. It will be understood that the term oligonucleotide is substantially equivalent to the terms primer, probe, or amplimer, as commonly defined in the art. It will also be appreciated by those skilled in the pertinent art that a longer oligonucleotide probe, or mixtures of probes, e.g., degenerate probes, can be used to detect longer, or more complex, nucleic acid sequences, for example, genomic DNA. In such cases, the probe may comprise at least 20–200 nucleotides, preferably, at least 30–100 nucleotides, more preferably, 50–100 nucleotides.

"Amplification" refers to the production of additional copies of a nucleic acid sequence and is generally carried out using polymerase chain reaction (PCR) technologies, which are well known and practiced in the art (see, D. W. Dieffenbach and G. S. Dveksler, 1995, *PCR Primer, a Laboratory Manual*, Cold Spring Harbor Press, Plainview, N.Y.).

"Microarray" is an array of distinct polynucleotides or oligonucleotides synthesized on a substrate, such as paper, nylon, or other type of membrane; filter; chip; glass slide; or any other type of suitable solid support.

The term "antisense" refers to nucleotide sequences, and compositions containing nucleic acid sequences, which are complementary to a specific DNA or RNA sequence. The term "antisense strand" is used in reference to a nucleic acid strand that is complementary to the "sense" strand. Antisense (i.e., complementary) nucleic acid molecules include PNA and may be produced by any method, including synthesis or transcription. Antisense oligonucleotides may be single or double stranded. Double stranded RNA's may be designed based upon the teachings of Paddison et al., Proc. Nat. Acad. Sci., 99:1443–1448 (2002); and International Publication Nos. WO 01/29058, and WO 99/32619; which are hereby incorporated herein by reference. Once introduced into a cell, the complementary nucleotides combine with natural sequences produced by the cell to form duplexes, which block either transcription or translation. The designation "negative" is sometimes used in reference to the antisense strand, and "positive" is sometimes used in reference to the sense strand.

The term "consensus" refers to the sequence that reflects the most common choice of base or amino acid at each position among a series of related DNA, RNA or protein sequences. Areas of particularly good agreement often represent conserved functional domains.

A "deletion" refers to a change in either nucleotide or amino acid sequence and results in the absence of one or more nucleotides or amino acid residues. By contrast, an insertion (also termed "addition") refers to a change in a nucleotide or amino acid sequence that results in the addition of one or more nucleotides or amino acid residues, as compared with the naturally occurring molecule. A substitution refers to the replacement of one or more nucleotides or amino acids by different nucleotides or amino acids.

A "derivative" nucleic acid molecule refers to the chemical modification of a nucleic acid encoding, or complementary to, the encoded HGPRBMY18 polypeptide. Such modifications include, for example, replacement of hydrogen by an alkyl, acyl, or amino group. A nucleic acid derivative encodes a polypeptide, which retains the essential biological and/or functional characteristics of the natural molecule. A derivative polypeptide is one, which is modified by glycosylation, pegylation, or any similar process that retains the biological and/or functional or immunological activity of the polypeptide from which it is derived.

The term "biologically active", i.e., functional, refers to a protein or polypeptide or fragment thereof having structural, regulatory, or biochemical functions of a naturally occurring molecule. Likewise, "immunologically active" refers to the capability of the natural, recombinant, or synthetic HGPRBMY18, or any oligopeptide thereof, to induce a specific immune response in appropriate animals or cells, for example, to generate antibodies, and to bind with specific antibodies.

The term "hybridization" refers to any process by which a strand of nucleic acid binds with a complementary strand through base pairing.

The term "hybridization complex" refers to a complex formed between two nucleic acid sequences by virtue of the formation of hydrogen bonds between complementary G and C bases and between complementary A and T bases. The hydrogen bonds may be further stabilized by base stacking interactions. The two complementary nucleic acid sequences hydrogen bond in an anti-parallel configuration. A hybridization complex may be formed in solution (e.g., $C_o t$ or $R_o t$ analysis), or between one nucleic acid sequence present in solution and another nucleic acid sequence immobilized on a solid support (e.g., membranes, filters, chips, pins, or glass slides, or any other appropriate substrate to which cells or their nucleic acids have been affixed).

The terms "stringency" or "stringent conditions" refer to the conditions for hybridization as defined by nucleic acid composition, salt and temperature. These conditions are well known in the art and may be altered to identify and/or detect identical or related polynucleotide sequences in a sample. A variety of equivalent conditions comprising either low, moderate, or high stringency depend on factors such as the length and nature of the sequence (DNA, RNA, base composition), reaction milieu (in solution or immobilized on a solid substrate), nature of the target nucleic acid (DNA, RNA, base composition), concentration of salts and the presence or absence of other reaction components (e.g., formamide, dextran sulfate and/or polyethylene glycol) and reaction temperature (within a range of from about 5° C. below the melting temperature of the probe to about 20° C. to 25° C. below the melting temperature). One or more factors may be varied to generate conditions, either low or high stringency, that is different from but equivalent to the aforementioned conditions.

As will be understood by those of skill in the art, the stringency of hybridization may be altered in order to identify or detect identical or related polynucleotide sequences. As will be further appreciated by the skilled practitioner, the melting temperature, $T_m$, can be approximated by the formulas as known in the art, depending on a number of parameters, such as the length of the hybrid or probe in number of nucleotides, or hybridization buffer ingredients and conditions (see, for example, T. Maniatis et al., Molecular Cloning: A Laboratory Manual, Cold Spring Harbor Laboratory, Cold Spring Harbor, N.Y., 1982 and J. Sambrook et al., Molecular Cloning: A Laboratory Manual, Cold Spring Harbor Laboratory, Cold Spring Harbor, N.Y., 1989; Current Protocols in Molecular Biology, Eds. F. M. Ausubel et al., Vol. 1, "Preparation and Analysis of DNA", John Wiley and Sons, Inc., 1994–1995, Suppls. 26, 29, 35 and 42; pp. 2.10.7–2.10.16; G. M. Wahl and S. L. Berger (1987; Methods Enzymol. 152:399–407); and A. R. Kimmel, 1987; Methods of Enzymol. 152:507–511). As a general guide, $T_m$ decreases approximately 1° C.–1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, e.g., high, moderate, or low stringency, typically relates to such washing conditions.

Thus, by way of non-limiting example, "high stringency" refers to conditions that permit hybridization of those nucleic acid sequences that form stable hybrids in 0.018M NaCl at about 65° C. (i.e., if a hybrid is not stable in 0.018M NaCl at about 65° C., it will not be stable under high stringency conditions). High stringency conditions can be provided, for instance, by hybridization in 50% formamide, 5× Denhardt's solution, 5×SSPE (saline sodium phosphate EDTA) (1×SSPE buffer comprises 0.15 M NaCl, 10 mM $Na_2HPO_4$, 1 mM EDTA), (or 1×SSC buffer containing 150 mM NaCl, 15 mM $Na_3$ citrate•$2H_2O$, pH 7.0), 0.2% SDS at about 42° C., followed by washing in 1×SSPE (or saline sodium citrate, SSC) and 0.1% SDS at a temperature of at least about 42° C., preferably about 55° C., more preferably about 65° C.

"Moderate stringency" refers, by non-limiting example, to conditions that permit hybridization in 50% formamide, 5× Denhardt's solution, 5×SSPE (or SSC), 0.2% SDS at 42° C. (to about 50° C.), followed by washing in 0.2×SSPE (or SSC) and 0.2% SDS at a temperature of at least about 42° C., preferably about 55° C., more preferably about 65° C.

"Low stringency" refers, by non-limiting example, to conditions that permit hybridization in 10% formamide, 5× Denhardt's solution, 6×SSPE (or SSC), 0.2% SDS at 42° C., followed by washing in 1×SSPE (or SSC) and 0.2% SDS at a temperature of about 45° C., preferably about 50° C.

For additional stringency conditions, see T. Maniatis et al., Molecular Cloning: A Laboratory Manual, Cold Spring Harbor Laboratory, Cold Spring Harbor, N.Y. (1982). It is to be understood that the low, moderate and high stringency hybridization/washing conditions may be varied using a variety of ingredients, buffers and temperatures well known to and practiced by the skilled artisan.

The terms "complementary" or "complementarity" refer to the natural binding of polynucleotides under permissive salt and temperature conditions by base pairing. For example, the sequence "A-G-T" binds to the complementary sequence "T-C-A". Complementarity between two single-stranded molecules may be "partial", in which only some of the nucleic acids bind, or it may be complete when total complementarity exists between single stranded molecules. The degree of complementarity between nucleic acid strands has significant effects on the efficiency and strength of hybridization between nucleic acid strands. This is of particular importance in amplification reactions, which depend upon binding between nucleic acids strands, as well as in the design and use of PNA molecules.

The term "homology" refers to a degree of complementarity. There may be partial homology or complete homology, wherein complete homology is equivalent to identity. A partially complementary sequence that at least partially inhibits an identical sequence from hybridizing to a target nucleic acid is referred to using the functional term "substantially homologous". The inhibition of hybridization of the completely complementary sequence to the target sequence may be examined using a hybridization assay (e.g., Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Those having skill in the art will know how to determine percent identity between/among sequences using, for example, algorithms such as those based on the CLUSTALW computer program (J. D. Thompson et al., 1994, *Nucleic Acids Research*, 2(22):4673–4680), or FASTDB, (Brutlag et al., 1990, *Comp. App. Biosci.*, 6:237–245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations.

A "composition" comprising a given polynucleotide sequence refers broadly to any composition containing the given polynucleotide sequence. The composition may comprise a dry formulation or an aqueous solution. Compositions comprising polynucleotide sequence (SEQ ID NO:1) encoding HGPRBMY18 polypeptide (SEQ ID NO:2), or fragments thereof, may be employed as hybridization probes. The probes may be stored in freeze-dried form and may be in association with a stabilizing agent such as a carbohydrate. In hybridizations, the probe may be employed in an aqueous solution containing salts (e.g., NaCl), detergents or surfactants (e.g., SDS) and other components (e.g., Denhardt's solution, dry milk, salmon sperm DNA, and the like).

The term "substantially purified" refers to nucleic acid sequences or amino acid sequences that are removed from their natural environment, isolated or separated, and are at least 60% free, preferably 75% to 85% free, and most preferably 90% or greater free from other components with which they are naturally associated.

The term "sample", or "biological sample", is meant to be interpreted in its broadest sense. A biological sample suspected of containing nucleic acid encoding HGPRBMY18 protein, or fragments thereof, or HGPRBMY18 protein itself, may comprise a body fluid, an extract from cells or tissue, chromosomes isolated from a cell (e.g., a spread of metaphase chromosomes), organelle, or membrane isolated from a cell, a cell, nucleic acid such as genomic DNA (in solution or bound to a solid support such as for Southern analysis), RNA (in solution or bound to a solid support such as for Northern analysis), cDNA (in solution or bound to a solid support), a tissue, a tissue print and the like.

"Transformation" refers to a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and partial bombardment. Such "transformed" cells include stably transformed cells in which the inserted DNA is capable of replication either as an autonomously replicating plasmid or as part of the host chromosome. Transformed cells also include those cells, which transiently express the inserted DNA or RNA for limited periods of time.

The term "mimetic" refers to a molecule, the structure of which is developed from knowledge of the structure of HGPRBMY18 protein, or portions thereof, and as such, is able to effect some or all of the actions of HGPRBMY18 protein.

The term "portion" with regard to a protein (as in "a portion of a given protein") refers to fragments or segments of that protein. The fragments may range in size from four or five amino acid residues to the entire amino acid sequence minus one amino acid. Thus, a protein "comprising at least a portion of the amino acid sequence of SEQ ID NO: 2" encompasses the full-length human HGPRBMY18 polypeptide, and fragments thereof.

As will be appreciated by the skilled practitioner, should the amino acid fragment comprise an antigenic epitope, for example, biological function per se need not be maintained. The terms HGPRBMY18 polypeptide and HGPRBMY18 protein are used interchangeably herein to refer to the encoded product of the HGPRBMY18 nucleic acid sequence according to the present invention.

The term "antibody" refers to intact molecules as well as fragments thereof, such as Fab, $F(ab')_2$, Fv, or Fc, which are capable of binding an epitopic or antigenic determinant. Antibodies that bind to HGPRBMY18 polypeptides can be prepared using intact polypeptides or fragments containing small peptides of interest or prepared recombinantly for use as the immunizing antigen. The polypeptide or oligopeptide used to immunize an animal can be derived from the transition of RNA or synthesized chemically, and can be conjugated to a carrier protein, if desired. Commonly used carriers that are chemically coupled to peptides include, but are not limited to, bovine serum albumin (BSA), keyhole limpet hemocyanin (KLH), and thyroglobulin. The coupled peptide is then used to immunize the animal (e.g., a mouse, a rat, or a rabbit).

The term "humanized" antibody refers to antibody molecules in which amino acids have been replaced in the non-antigen binding regions in order to more closely resemble a human antibody, while still retaining the original binding capability, e.g., as described in U.S. Pat. No. 5,585,089 to C. L. Queen et al.

The term "antigenic determinant" refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to an antigenic determinants. An antigenic determinant may compete with the intact antigen (i.e., the immunogen used to elicit the immune response) for binding to an antibody.

The terms "specific binding" or "specifically binding" refer to the interaction between a protein or peptide and a binding molecule, such as an agonist, an antagonist, or an antibody. The interaction is dependent upon the presence of a particular structure (i.e., an antigenic determinant or epitope) of the protein that is recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The term "correlates with expression of a polynucleotide" indicates that the detection of the presence of ribonucleic acid that is similar to SEQ ID NO:1 by Northern analysis is indicative of the presence of mRNA encoding HGPRBMY18 polypeptide (SEQ ID NO:2) in a sample and thereby correlates with expression of the transcript from the polynucleotide encoding the protein.

An alteration in the polynucleotide of SEQ ID NO:1 comprises any alteration in the sequence of the polynucleotides encoding HGPRBMY18 polypeptide, including deletions, insertions, and point mutations that may be detected using hybridization assays. Included within this definition is the detection of alterations to the genomic DNA sequence which encodes HGPRBMY18 polypeptide (e.g., by alterations in the pattern of restriction fragment length polymorphisms capable of hybridizing to SEQ ID NO:1), the inability of a selected fragment of SEQ ID NO:1 to hybridize to a sample of genomic DNA (e.g., using allele-specific oligonucleotide probes), and improper or unexpected hybridization, such as hybridization to a locus other than the normal chromosomal locus for the polynucleotide sequence encoding HGPRBMY18 polypeptide (e.g., using fluorescent in situ hybridization (FISH) to metaphase chromosome spreads).

DESCRIPTION OF THE PRESENT INVENTION

The present invention provides a novel human member of the G-protein coupled receptor (GPCR) family (HGPRBMY18). Based on sequence homology, the protein HGPRBMY18 is a novel human GPCR. This protein sequence has been predicted to contain seven transmembrane domains which is a characteristic structural feature of GPCRs. HGPRBMY18 belongs to the "class A" of GPCR superfamily and is closely related to adrenergic and serotonin receptors based on sequence similarity. Class A is the largest sub-family of the GPCR superfamily. This particular orphan GPCR is expressed highly in pituitary gland and colon, while sporadically expressed in breast, lung and prostate.

HGPRBMY18 polypeptides and polynucleotides are useful for diagnosing diseases related to over- or under-expression of HGPRBMY18 proteins by identifying mutations in the HGPRBMY18 gene using HGPRBMY18 probes, or by determining HGPRBMY18 protein or mRNA expression levels. HGPRBMY18 polypeptides are also useful for screening compounds, which affect activity or function of the protein. The invention encompasses the polynucleotide encoding the HGPRBMY18 polypeptide and the use of the HGPRBMY18 polynucleotide or polypeptide, or composition thereof, in the screening, diagnosis, treatment, or prevention of disorders associated with aberrant or uncontrolled cellular growth and/or function, such as neoplastic diseases (e.g., cancers and tumors), with particular regard to diseases or disorders related to the pituitary gland, e.g. endocrine diseases, colon, breast, lung, and prostate.

Nucleic acids encoding human HGPRBMY18 according to the present invention were first identified in Incyte CloneID: 5029478 through a computer search for amino acid sequence alignments (see Example 1).

In one of its embodiments, the present invention encompasses a polypeptide comprising the amino acid sequence of SEQ ID NO:2 as shown in FIG. 1. The HGPRBMY18 polypeptide is 361 amino acids in length and shares amino acid sequence homology with the rat galanin receptor. The HGPRBMY18 polypeptide (SEQ ID NO:2) shares 33.3% identity and 41.1% similarity with over 360 amino acids of the G-Protein Coupled Receptor RE2, wherein "similar" amino acids are those which have the same/similar physical properties and in many cases, the function is conserved with similar residues. For example, amino acids Lysine and Arginine are similar; while residues such as Proline and Cysteine, which do not share any physical properties, are dissimilar. The polypeptide HGPRMBY18 (SEQ ID NO:2) shares 29.5% identity and 38.35% similarity with the *Ovis aries* melatonin receptor type 1A (ML1A_SHEEP; SWISS-Prot Acc. No.:P48040; SEQ ID NO:8); shares 29.5% identity and 38.35% similarity with the *Ovis aries* melatonin receptor MEL-1A (046608; SWISS-Prot Acc. No.:046608; SEQ ID NO:9); shares 28.53% identity and 36.34% similarity with the *Mus musculus* galanin receptor type 1 (GAL-R_MOUSE; SWISS-Prot Acc. No.:P56479; SEQ ID NO:10); 31.5% identity and 38.84% similarity with the *Rattus norvegicus* galanin receptor type 1 (GALR_RAT; SWISS-Prot Acc. No.:Q62805; SEQ ID NO:11); 30.4% identity and 37.39% similarity with the human galanin receptor type 1 (GALR_HUMAN; SWISS-Prot Acc. No.: P47211; SEQ ID NO:12); 29.1% identity and 36.53% similarity with the *Mus musculus* somatostatin receptor type 5 (SSR5_MOUSE; SWISS-Prot Acc. No.:O08858, SEQ ID NO:13); 29.28% identity and 37.7% similarity with the *Rattus norvegicus* somatostatin receptor type 5 (SSR5_RAT; SWISS-Prot Acc. No.:P30938; SEQ ID NO:14); 26.65% identity and 34.43% similarity with the *Mus musculus* somatostatin receptor type 3 (SSR3_MOUSE; SWISS-Prot Acc. No.:P30935; SEQ ID NO:15); 28.7% identity and 36.56% similarity with the *Rattus norvegicus* somatostatin receptor type 3 (SSR3_RAT; SWISS-Prot Acc. No.:P30936; SEQ ID NO:16); 28.75% identity and 36.7% similarity with the human somatostatin receptor type 3 (SSR3_HUMAN; SWISS-Prot Acc. No.:P32745; SEQ ID NO:17); 27.25% identity and 39.42% with the *Mus musculus* neuropeptide Y receptor type 2 (NY2R_MOUSE; SWISS-Prot Acc. No.: P97295; SEQ ID NO:18); and 30.11% identity and 41.76% similarity with the human orexin receptor type 2 (OX2R_HUMAN; SWISS-Prot Acc. No.:O43614; SEQ ID NO:19).

Variants of the HGPRBMY18 polypeptide are also encompassed by the present invention. A preferred HGPRBMY18 variant has at least 75 to 80%, more preferably at least 85 to 90%, and even more preferably at least 90% amino acid sequence identity to the amino acid sequence claimed herein, and which retains at least one biological, immunological, or other functional characteristic or activity of the HGPRBMY18 polypeptide. Most preferred is a variant having at least 95% amino acid sequence identity to that of SEQ ID NO:2.

In another embodiment, the present invention encompasses polynucleotides, which encode the HGPRBMY18 polypeptide. Accordingly, any nucleic acid sequence, which encodes the amino acid sequence of HGPRBMY18 polypeptide, can be used to produce recombinant molecules that express HGPRBMY18 protein. In a particular embodiment, the present invention encompasses the HGPRBMY18 polynucleotide comprising the nucleic acid sequence of SEQ ID NO:1 as shown in FIG. 1. More particularly, the present invention provides the HGPRBMY18 clone, deposited at the American Type Culture Collection (ATCC), 10801 University Boulevard, Manassas, Va. 20110-2209 on Dec. 8, 2000, and under ATCC Accession No. PTA-2766 according to the terms of the Budapest Treaty.

Expanded analysis of HGPRBMY18 expression levels by TaqMan™ quantitative PCR (see FIG. 9) confirmed that the HGPRBMY18 polypeptide is expressed in pituitary (FIG. 7). HGPRBMY18 mRNA was expressed predominately in the pituitary gland (approximately 2200 fold higher expression as compared to the lowest expressed tissue, which is represented by kidney cortex). HGPRBMY18 polypeptide was also significantly expressed in the rectum, colon and caecum, and to a lesser extent throughout the brain and in the breast.

The striking pattern of HGPRBMY18 expression in the pituitary and portions of the lower GI suggest a particular functional relationship between HGPRBMY18 and these distal sites. Based upon these observations, it is possible that HGPRBMY18 is involved in the control of certain hormone secretions, such as, but not limited to prolactin, oxytocin, growth hormone and vasopressin from the pituitary gland, as well as the specific receptors in the lower GI which enable functional responses to one or more of these hormones. These data suggest that modulators of HGPRBMY18 function may have important utilities in the treatment of various aliments of the pituitary and the lower GI, including hyperprolactinemia, and colorectal cancers of various origins as well as cancers in other tissues where receptors may be expressed albeit at low levels.

Morever, an additional analysis of HGPRBMY18 expression levels by TaqMan™ quantitative PCR (see FIG. 11) in disease cells and tissues indicated that the HGPRBMY18 polypeptide is differentially expressed in renal tumor tissues. In the renal tumor tissue results, an average of 4 samples showed a 4.98-fold induction in HGPRBMY18 steady state RNA over that observed in 4 matched normal renal samples (P=0.036). This differential expression pattern is likely physiologically relevant since the tissue showing the lowest expression level of HGPRBMY18 out of 72 tissues tested was found to be normal kidney tissue (see FIG. 9). The fact that HGPRBMY18 is significantly overexpressed specifically in renal tumor tissues is highly suggestive that HGPRBMY18 is involved in events either directly or indirectly linked to the incidence of renal tumors. Importantly, the differential expression pattern illustrates that HGPRBMY18 is useful as a diagnostic marker for renal tumors. Moreover, this data supports a role of HGPRBMY18 in regulating the initiation and or maintenance of the renal cell metastatic state and that modulators of HGPRBMY18 function may have utility in the treatment of renal cancers.

HGPRBMY18 polynucleotides, polypeptides, fragments, and/or modulators thereof are useful for the treatment, amelioration, detection, and/or prevention of various diseases and disorders, particularly various aliments of the pituitary gland, and the lower GI, including hyperprolactinemia, in addition to colorectal cancers of various origins as well as cancers in other tissues where receptors may be expressed albeit at low levels.

The strong homology to human G-protein coupled receptors, combined with the predominate expression in pituitary gland tissue suggests the HGPRBMY18 polynucleotides and polypeptides may be useful in treating, diagnosing, prognosing, and/or preventing endocrine diseases and/or disorders, which include, but are not limited to, the following: aberrant growth hormone synthesis and/or secretion, aberrant prolactin synthesis and/or secretion, aberrant luteinizing hormone synthesis and/or secretion, aberrant follicle-stimulating hormone synthesis and/or secretion, aberrant thyroid-stimulating hormone synthesis and/or secretion, aberrant adrenocorticotropin synthesis and/or secretion, aberrant vasopressin secretion, aberrant oxytocin secretion, aberrant growth, aberrant lactation, aberrant sexual characteristic development, aberrant testosterone synthesis and/or secretion, aberrant estrogen synthesis and/or secretion, aberrant water homeostasis, hypogonadism, Addison's disease, hypothyroidism, Cushing's disease, agromegaly, gigantism, lethargy, osteoporosis, aberrant calcium homeostasis, aberrant potassium homeostasis, reproductive disorders, and developmental disorders.

Figure 10:
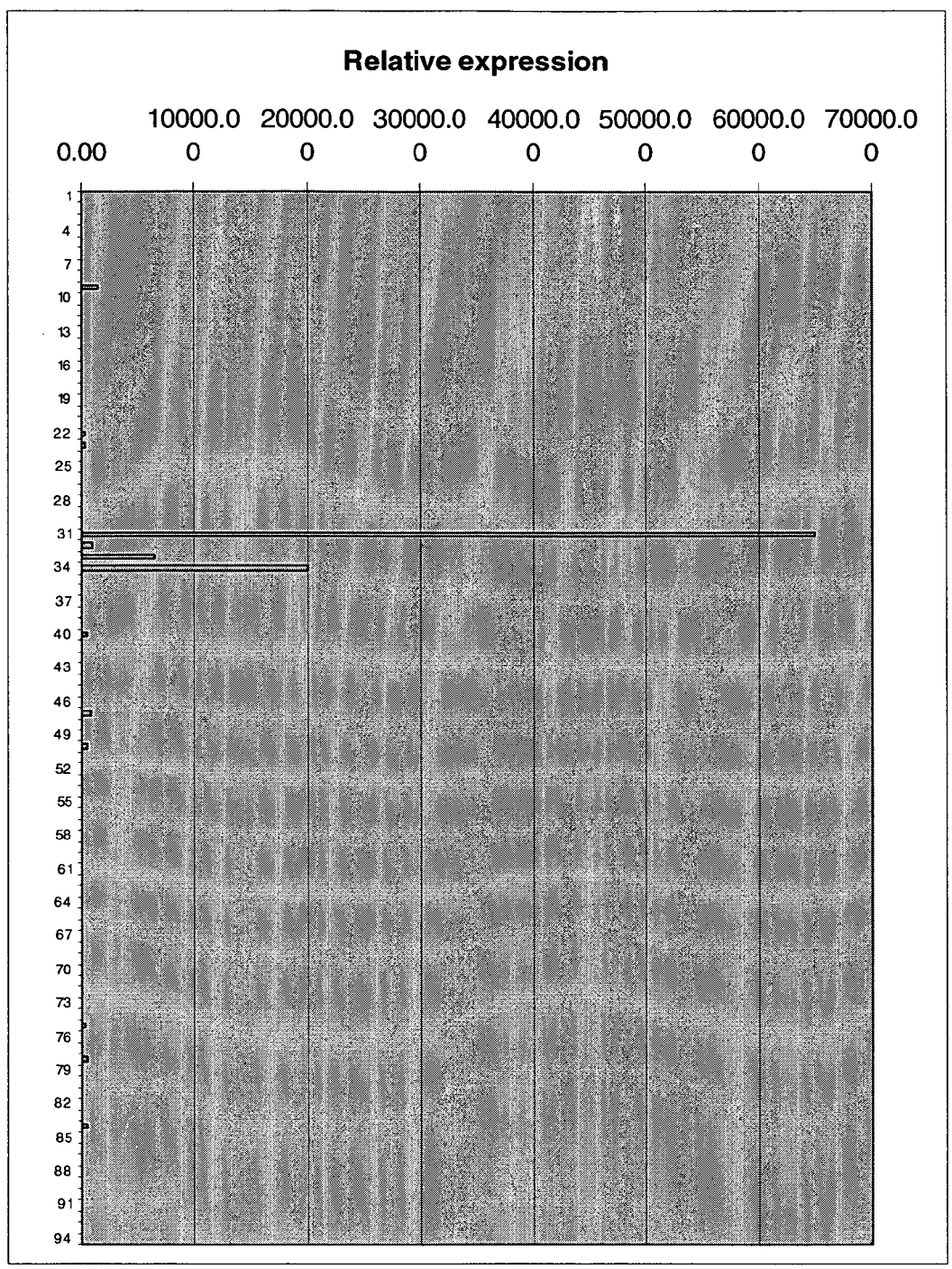
FIG. 10 shows an expanded expression profile of the novel human G-protein coupled receptor, HGPRBMY18, of the present invention. The figure illustrates the relative expression level of HGPRBMY18 amongst mRNA isolated from a number of cancer cell lines. As shown, the HGPRBMY18 polypeptide was expressed in several colon cancer cell lines, and to a lesser extent in other human tumor cell lines as shown. Expression data was obtained by measuring the steady state HGPRBMY18 mRNA levels by quantitative PCR using the PCR primer pair provided as SEQ ID NO:49 and 50 as described in Example 7 herein. An index listing the tissue of origin of each mRNA referenced on the X-axis is provided in Table 2.

Addition expression profiling analysis of HGPRBMY18 expression levels in various cancer cell lines by TaqMan™ quantitative PCR (see FIGS. 8 and 10) determined that HGPRBMY18 is predominately expressed in several colon cancer cell lines, and to a lesser extent in other human tumor cell lines as shown, suggesting HGPRBMY18 may be diagnostic of aggressive transformed phenotypes. The data suggests the HGPRBMY18 polypeptide may play a critical role in the development of a transformed phenotype leading to the development of colon cancers and/or a proliferative conditions, either directly or indirectly. Alternatively, the HGPRBMY18 polypeptide may play a protective role and could be activated in response to a cancerous or proliferative phenotype. Whether HGPRBMY18 plays a role in directing transformation, or plays the role of protecting cells in response to a transformed phenotype, its role in colon tumors is likely to be enhanced relative to normal tissues. Therefore, antagonists or agonists of the HGPRBMY18 polypeptide may be useful in the treatment, amelioration, and/or prevention of a variety of proliferative conditions, including, but not limited to colon, and colon tumors.

As will be appreciated by the skilled practitioner in the art, the degeneracy of the genetic code results in the production of a number of nucleotide sequences encoding HGPRBMY18 polypeptide. Some of the sequences bear minimal homology to the nucleotide sequences of any known and naturally occurring gene. Accordingly, the present invention contemplates each and every possible variation of nucleotide sequence that could be made by selecting combinations based on possible codon choices. These combinations are made in accordance with the standard triplet genetic code as applied to the nucleotide sequence of naturally occurring HGPRBMY18, and all such variations are to be considered as being specifically disclosed.

Although nucleotide sequences which encode HGPRBMY18 polypeptide and its variants are preferably capable of hybridizing to the nucleotide sequence of the naturally occurring HGPRBMY18 polypeptide under appropriately selected conditions of stringency, it may be advantageous to produce nucleotide sequences encoding HGPRBMY18 polypeptide, or its derivatives, which possess a substantially different codon usage. Codons may be selected to increase the rate at which expression of the peptide/polypeptide occurs in a particular prokaryotic or eukaryotic host in accordance with the frequency with which particular codons are utilized by the host. Other reasons for substantially altering the nucleotide sequence encoding HGPRBMY18 polypeptide, and its derivatives, without altering the encoded amino acid sequences include the production of RNA transcripts having more desirable properties, such as a greater half-life, than transcripts produced from the naturally occurring sequence.

The present invention also encompasses production of DNA sequences, or portions thereof, which encode the HGPRBMY18 polypeptide, and its derivatives, entirely by synthetic chemistry. After production, the synthetic sequence may be inserted into any of the many available expression vectors and cell systems using reagents that are well known and practiced by those in the art. Moreover, synthetic chemistry and other known techniques may be used to introduce mutations into a sequence encoding HGPRBMY18 polypeptide, or any fragment thereof.

In preferred embodiments, the present invention encompasses a polynucleotide lacking the initiating start codon, in addition to, the resulting encoded polypeptide of HGPRBMY18. Specifically, the present invention encompasses the polynucleotide corresponding to nucleotides 4 thru 1083 of SEQ ID NO:1, and the polypeptide corresponding to amino acids 2 thru 361 of SEQ ID NO:2. Also encompassed are recombinant vectors comprising said encoding sequence, and host cells comprising said vector.

Also encompassed by the present invention are polynucleotide sequences that are capable of hybridizing to the claimed nucleotide sequence of HGPRBMY18, such as that shown in SEQ ID NO:1, under various conditions of stringency. Hybridization conditions are typically based on the melting temperature ($T_m$) of the nucleic acid binding complex or probe (see, G. M. Wahl and S. L. Berger, 1987; *Methods Enzymol.*, 152:399–407 and A. R. Kimmel, 1987; *Methods of Enzymol.*, 152:507–511), and may be used at a defined stringency. For example, included in the present invention are sequences capable of hybridizing under moderately stringent conditions to the HGPRBMY18 sequence of SEQ ID NO:1 and other sequences which are degenerate to those which encode HGPRBMY18 polypeptide (e.g., as a non-limiting example: prewashing solution of 2×SSC, 0.5% SDS, 1.0 mM EDTA, pH 8.0, and hybridization conditions of 50° C., 5×SSC, overnight.

The nucleic acid sequence encoding the HGPRBMY18 protein may be extended utilizing a partial nucleotide sequence and employing various methods known in the art to detect upstream sequences such as promoters and regulatory elements. For example, one method, which may be employed, is restriction-site PCR, which utilizes universal primers to retrieve unknown sequence adjacent to a known locus (G. Sarkar, 1993, *PCR Methods Applic.*, 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region or sequence (T. Triglia et al., 1988, *Nucleic Acids Res.*, 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome (YAC) DNA (M. Lagerstrom et al., 1991, *PCR Methods Applic.*, 1:111–119). In this method, multiple restriction enzyme digestions and ligations may also be used to place an engineered double-stranded sequence into an unknown portion of the DNA molecule before performing PCR. J. D. Parker et al. (1991; *Nucleic Acids Res.*, 19:3055–3060) provide another method which may be used to retrieve unknown sequences. In addition, PCR, nested primers, and PROMOTERFINDER libraries can be used to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, since they will contain more sequences, which contain the 5' regions of genes. The use of a randomly primed library may be especially preferable for situations in which an oligo d(T) library does not yield a full-length cDNA. Genomic libraries may be useful for extension of sequence into the 5' and 3' non-transcribed regulatory regions.

The embodiments of the present invention can be practiced using methods for DNA sequencing which are well known and generally available in the art. The methods may employ such enzymes as the Klenow fragment of DNA polymerase I, SEQUENASE (U.S. Biochemical Corp. Cleveland, Ohio), Taq polymerase (PE Biosystems), thermostable T7 polymerase (Amersham Pharmacia Biotech, Piscataway, N.J.), or combinations of recombinant polymerases and proofreading exonucleases such as the ELONGASE Amplification System marketed by Life Technologies (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA sequencers (PE Biosystems).

Commercially available capillary electrophoresis systems may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g., GENOTYPER and SEQUENCE NAVIGATOR, PE Biosystems) and the entire process—from loading of samples to computer analysis and electronic data display—may be computer controlled. Capillary electrophoresis is especially preferable for the sequencing of small pieces of DNA, which might be present in limited amounts in a particular sample.

In another embodiment of the present invention, polynucleotide sequences or fragments thereof which encode HGPRBMY18 polypeptide, or peptides thereof, may be used in recombinant DNA molecules to direct the expression of HGPRBMY18 polypeptide product, or fragments or functional equivalents thereof, in appropriate host cells. Because of the inherent degeneracy of the genetic code, other DNA sequences, which encode substantially the same or a functionally equivalent amino acid sequence, may be produced and these sequences may be used to clone and express HGPRBMY18 protein.

As will be appreciated by those having skill in the art, it may be advantageous to produce HGPRBMY18 polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequence of the present invention can be engineered using methods generally known in the art in order to alter HGPRBMY18 polypeptide-encoding sequences for a variety of reasons, including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and the like.

In another embodiment of the present invention, natural, modified, or recombinant nucleic acid sequences encoding HGPRBMY18 polypeptide may be ligated to a heterologous sequence to encode a fusion protein. For example, for screening peptide libraries for inhibitors of HGPRBMY18 activity, it may be useful to encode a chimeric HGPRBMY18 protein that can be recognized by a commercially available antibody. A fusion protein may also be engineered to contain a cleavage site located between the HGPRBMY18 protein-encoding sequence and the heterologous protein sequence, so that HGPRBMY18 protein may be cleaved and purified away from the heterologous moiety.

In another embodiment, sequences encoding HGPRBMY18 polypeptide may be synthesized in whole, or in part, using chemical methods well known in the art (see, for example, M. H. Caruthers et al., 1980, *Nucl. Acids Res. Symp. Ser.*, 215–223 and T. Horn et al., 1980, *Nucl. Acids Res. Svmp. Ser.*, 225–232). Alternatively, the protein itself may be produced using chemical methods to synthesize the amino acid sequence of HGPRBMY18 polypeptide, or a fragment or portion thereof. For example, peptide synthesis can be performed using various solid-phase techniques (J. Y. Roberge et al., 1995, *Science*, 269:202–204) and automated synthesis may be achieved, for example, using the ABI 431A Peptide Synthesizer (PE Biosystems).

The newly synthesized peptide can be substantially purified by preparative high performance liquid chromatography (e.g., T. Creighton, 1983, *Proteins, Structures and Molecular Principles*, W.H. Freeman and Co., New York, N.Y.), by reversed-phase high performance liquid chromatography, or other purification methods as are known in the art. The composition of the synthetic peptides may be confirmed by amino acid analysis or sequencing (e.g., the Edman degradation procedure; Creighton, supra). In addition, the amino acid sequence of HGPRBMY18 polypeptide or any portion thereof, may be altered during direct synthesis and/or combined using chemical methods with sequences from other proteins, or any part thereof, to produce a variant polypeptide.

To express a biologically active HGPRBMY18 polypeptide or peptide, the nucleotide sequences encoding HGPRBMY18 polypeptide, or functional equivalents, may be inserted into an appropriate expression vector, i.e., a vector, which contains the necessary elements for the transcription and translation of the inserted coding sequence.

Methods, which are well known to those skilled in the art, may be used to construct expression vectors containing sequences encoding HGPRBMY18 polypeptide and appropriate transcriptional and translational control elements. These methods include in vitro recombinant DNA techniques, synthetic techniques, and in vivo genetic recombination. Such techniques are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

A variety of expression vector/host systems may be utilized to contain and express sequences encoding HGPRBMY18 polypeptide. Such expression vector/host systems include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) and tobacco mosaic virus (TMV)), or with bacterial expression vectors (e.g., Ti or pBR322 plasmids); or animal cell systems. The host cell employed is not limiting to the present invention.

"Control elements" or "regulatory sequences" are those non-translated regions of the vector, e.g., enhancers, promoters, 5' and 3' untranslated regions, which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (Life Technologies), and the like, may be used. The baculovirus polyhedrin promoter may be used in insect cells. Promoters or enhancers derived from the genomes of plant cells (e.g., heat shock, RUBISCO; and storage protein genes), or from plant viruses (e.g., viral promoters or leader sequences), may be cloned into the vector. In mammalian cell systems, promoters from mammalian genes or from mammalian viruses are preferred. If it is necessary to generate a cell line that contains multiple copies of the sequence encoding HGPRBMY18, vectors based on SV40 or EBV may be used with an appropriate selectable marker.

In bacterial systems, a number of expression vectors may be selected, depending upon the use intended for the expressed HGPRBMY18 product. For example, when large quantities of expressed protein are needed for the induction of antibodies, vectors, which direct high level expression of fusion proteins that are readily purified, may be used. Such vectors include, but are not limited to, the multifunctional *E. coli* cloning and expression vectors such as BLUESCRIPT (Stratagene; La Jolla, Calif.), in which the sequence encoding HGPRBMY18 polypeptide may be ligated into the vector in-frame with sequences for the amino-terminal Met and the subsequent 7 residues of β-galactosidase, so that a hybrid protein is produced; pIN vectors (see, G. Van Heeke and S. M. Schuster, 1989, *J. Biol. Chem.*, 264:5503–5509); and the like. pGEX vectors (Promega, Madison, Wis.) may also be used to express foreign polypeptides, as fusion proteins with glutathione S-transferase (GST). In general, such fusion proteins are soluble and can be easily purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. (For reviews, see F. M. Ausubel et al., supra, and Grant et al., 1987, *Methods Enzymol.*, 153:516–544).

Should plant expression vectors be desired and used, the expression of sequences encoding HGPRBMY18 polypeptide may be driven by any of a number of promoters. For example, viral promoters such as the 35S and 19S promoters of CaMV may be used alone or in combination with the omega leader sequence from TMV (N. Takamatsu, 1987, EMBO J., 6:307–311). Alternatively, plant promoters such as the small subunit of RUBISCO, or heat shock promoters, may be used (G. Coruzzi et al., 1984, *EMBO J.*, 3:1671–1680; R. Broglie et al., 1984, *Science*, 224:838–843; and J. Winter et al., 1991, *Results Probl. Cell Differ.* 17:85–105). These constructs can be introduced into plant cells by direct DNA transformation or pathogen-mediated transfection. Such techniques are described in a number of generally available reviews (see, for example, S. Hobbs or L. E. Murry, In: McGraw Hill *Yearbook of Science and Technology* (1992) McGraw Hill, New York, N.Y.; pp. 191–196).

An insect system may also be used to express HGPRBMY18 polypeptide. For example, in one such system, *Autographa californica* nuclear polyhedrosis virus (AcNPV) is used as a vector to express foreign genes in *Spodoptera frugiperda* cells or in *Trichoplusia* larvae. The sequences encoding HGPRBMY18 polypeptide may be cloned into a non-essential region of the virus such as the polyhedrin gene and placed under control of the polyhedrin promoter. Successful insertion of HGPRBMY18 polypeptide will render the polyhedrin gene inactive and produce recombinant virus lacking coat protein. The recombinant viruses may then be used to infect, for example, *S. frugiperda* cells or *Trichoplusia larvae* in which the HGPRBMY18 polypeptide product may be expressed (E. K. Engelhard et al., 1994, *Proc. Nat. Acad. Sci.*, 91:3224–3227).

In mammalian host cells, a number of viral-based expression systems may be utilized. In cases where an adenovirus is used as an expression vector, sequences encoding HGPRBMY18 polypeptide may be ligated into an adenovirus transcription/translation complex containing the late promoter and tripartite leader sequence. Insertion in a non-essential E1 or E3 region of the viral genome may be used to obtain a viable virus which is capable of expressing HGPRBMY18 polypeptide in infected host cells (J. Logan and T. Shenk, 1984, *Proc. Natl. Acad. Sci.*, 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding HGPRBMY18 polypeptide. Such signals include the ATG initiation codon and adjacent sequences. In cases where sequences encoding HGPRBMY18 polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals, including the ATG initiation codon, should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system that is used, such as those described in the literature (D. Scharf et al., 1994, *Results Probl. Cell Differ.*, 20:125–162).

Moreover, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells having specific cellular machinery and characteristic mechanisms for such post-translational activities (e.g., CHO, HeLa, MDCK, HEK293, and W138) are available from the American Type Culture Collection (ATCC), American Type Culture Collection (ATCC), 10801 University Boulevard, Manassas, Va. 20110-2209, and may be chosen to ensure the correct modification and processing of the foreign protein.

For long-term, high-yield production of recombinant proteins, stable expression is preferred. For example, cell lines which stably express HGPRBMY18 protein may be transformed using expression vectors which may contain viral origins of replication and/or endogenous expression elements and a selectable marker gene on the same, or on a separate, vector. Following the introduction of the vector, cells may be allowed to grow for 1–2 days in an enriched cell culture medium before they are switched to selective medium. The purpose of the selectable marker is to confer resistance to selection, and its presence allows the growth and recovery of cells, which successfully express the introduced sequences. Resistant clones of stably transformed cells may be proliferated using tissue culture techniques appropriate to the cell type.

Any number of selection systems may be used to recover transformed cell lines. These include, but are not limited to, the Herpes Simplex Virus thymidine kinase (HSV TK), (M. Wigler et al., 1977, *Cell*, 11:223–32) and adenine phosphoribosyltransferase (I. Lowy et al., 1980, *Cell*, 22:817–23) genes which can be employed in tk$^-$ or aprt$^-$ cells, respectively. Also, anti-metabolite, antibiotic or herbicide resistance can be used as the basis for selection; for example, dhfr, which confers resistance to methotrexate (M. Wigler et al., 1980, *Proc. Natl. Acad. Sci.*, 77:3567–70); npt, which confers resistance to the aminoglycosides neomycin and G-418 (F. Colbere-Garapin et al., 1981, *J. Mol. Biol.*, 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (S. C. Hartman and R. C. Mulligan, 1988, *Proc. Natl. Acad. Sci.*, 85:8047–51). Recently, the use of visible markers has gained popularity with such markers as the anthocyanins, β-glucuronidase and its substrate GUS, and luciferase and its substrate luciferin, which are widely used not only to identify transformants, but also to quantify the amount of transient or stable protein expression that is attributable to a specific vector system (C. A. Rhodes et al., 1995, *Methods Mol. Biol.*, 55:121–131).

Although the presence or absence of marker gene expression suggests that the gene of interest is also present, the presence and expression of the desired gene of interest may need to be confirmed. For example, if the nucleic acid sequence encoding HGPRBMY18 polypeptide is inserted within a marker gene sequence, recombinant cells containing sequences encoding HGPRBMY18 polypeptide can be identified by the absence of marker gene function. Alternatively, a marker gene can be placed in tandem with a sequence encoding HGPRBMY18 polypeptide under the control of a single promoter. Expression of the marker gene in response to induction or selection usually indicates co-expression of the tandem gene.

Alternatively, host cells, which contain the nucleic acid, sequence encoding HGPRBMY18 polypeptide and which express HGPRBMY18 polypeptide product may be identified by a variety of procedures known to those having skill in the art. These procedures include, but are not limited to, DNA—DNA or DNA-RNA hybridizations and protein bioassay or immunoassay techniques, including membrane, solution, or chip based technologies, for the detection and/or quantification of nucleic acid or protein.

The presence of polynucleotide sequences encoding HGPRBMY18 polypeptide can be detected by DNA—DNA or DNA-RNA hybridization, or by amplification using probes or portions or fragments of polynucleotides encoding HGPRBMY18 polypeptide. Nucleic acid amplification based assays involve the use of oligonucleotides or oligomers, based on the sequences encoding HGPRBMY18 polypeptide, to detect transformants containing DNA or RNA encoding HGPRBMY18 polypeptide.

A wide variety of labels and conjugation techniques are known and employed by those skilled in the art and may be used in various nucleic acid and amino acid assays. Means for producing labeled hybridization or PCR probes for detecting sequences related to polynucleotides encoding HGPRBMY18 polypeptide include oligo-labeling, nick translation, end-labeling, or PCR amplification using a labeled nucleotide. Alternatively, the sequences encoding HGPRBMY18 polypeptide, or any portions or fragments thereof, may be cloned into a vector for the production of an mRNA probe. Such vectors are known in the art, are commercially available, and may be used to synthesize RNA probes in vitro by addition of an appropriate RNA polymerase, such as T7, T3, or SP(6) and labeled nucleotides. These procedures may be conducted using a variety of commercially available kits (e.g., Amersham Pharmacia Biotech, Promega and U.S. Biochemical Corp.). Suitable reporter molecules or labels which may be used include radionuclides, enzymes, fluorescent, chemiluminescent, or chromogenic agents, as well as substrates, cofactors, inhibitors, magnetic particles, and the like.

Furthermore, in yet another embodiment, G-protein coupled receptor-encoding polynucleotide sequences can be used to purify a molecule or compound in a sample, wherein the molecule or compound specifically binds to the polynucleotide, comprising: a) combining the G-protein coupled receptor-encoding polynucleotide, or fragment thereof, under conditions to allow specific binding; b) detecting specific binding between the G-protein coupled receptor-encoding polynucleotide and the molecule or compound; c) recovering the bound polynucleotide; and d) separating the polynucleotide from the molecule or compound, thereby obtaining a purified molecule or compound.

Host cells transformed with nucleotide sequences encoding HGPRBMY18 protein, or fragments thereof, may be cultured under conditions suitable for the expression and recovery of the protein from cell culture. The protein produced by a recombinant cell may be secreted or contained intracellularly depending on the sequence and/or the vector used. As will be understood by those having skill in the art, expression vectors containing polynucleotides which encode HGPRBMY18 protein may be designed to contain signal sequences which direct secretion of the HGPRBMY18 protein through a prokaryotic or eukaryotic cell membrane. Other constructions may be used to join nucleic acid sequences encoding HGPRBMY18 protein to nucleotide sequence encoding a polypeptide domain, which will facilitate purification of soluble proteins. Such purification facilitating domains include, but are not limited to, metal chelating peptides such as histidine-tryptophan modules that allow purification on immobilized metals; protein A domains that allow purification on immobilized immunoglobulin; and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HGPRBMY18 protein may be used to facilitate purification. One such expression vector provides for expression of a fusion protein containing HGPRBMY18 and a nucleic acid encoding 6 histidine residues preceding a thioredoxin or an enterokinase cleavage site. The histidine residues facilitate purification on IMAC (immobilized metal ion affinity chromatography) as described by J. Porath et al., 1992, *Prot. Exp. Purif.*, 3:263–281, while the enterokinase cleavage site provides a means for purifying from the fusion protein. For a discussion of suitable vectors for fusion protein production, see D. J. Kroll et al., 1993; *DNA Cell Biol.*, 12:441–453.

In addition to recombinant production, fragments of HGPRBMY18 polypeptide may be produced by direct peptide synthesis using solid-phase techniques (J. Merrifield, 1963, J. Am. Chem. Soc., 85:2149–2154). Protein synthesis may be performed using manual techniques or by automation. Automated synthesis may be achieved, for example, using ABI 431A Peptide Synthesizer (PE Biosystems). Various fragments of HGPRBMY18 polypeptide can be chemically synthesized separately and then combined using chemical methods to produce the full-length molecule.

Human artificial chromosomes (HACs) may be used to deliver larger fragments of DNA than can be contained and expressed in a plasmid vector. HACs are linear microchromosomes which may contain DNA sequences of 10K to 10M in size, and contain all of the elements that are required for stable mitotic chromosome segregation and maintenance (see, J. J. Harrington et al., 1997, *Nature Genet.*, 15:345–355). HACs of 6 to 10M are constructed and delivered via conventional delivery methods (e.g., liposomes, polycationic amino polymers, or vesicles) for therapeutic purposes.

Diagnostic Assays

A variety of protocols for detecting and measuring the expression of HGPRBMY18 polypeptide using either polyclonal or monoclonal antibodies specific for the protein are known and practiced in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive with two non-interfering epitopes on the HGPRBMY18 polypeptide is preferred, but a competitive binding assay may also be employed. These and other assays are described in the art as represented by the publication of R. Hampton et al., 1990; *Serological Methods, a Laboratory Manual*, APS Press, St Paul, Minn. and D. E. Maddox et al., 1983; *J. Exp. Med.*, 158:1211–1216).

This invention also relates to the use of HGPRBMY18 polynucleotides as diagnostic reagents. Detection of a mutated form of the HGPRBMY18 gene associated with a dysfunction provides a diagnostic tool that can add to or define a diagnosis of a disease or susceptibility to a disease which results from under-expression, over-expression, or altered expression of HGPRBMY18. Individuals carrying mutations in the HGPRBMY18 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Hybridizing amplified DNA to labeled HGPRBMY18 polynucleotide sequences can identify point mutations. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc. Natl. Acad. Sci., USA* (1985) 85:43297–4401. In another embodiment, an array of oligonucleotides probes comprising HGPRBMY18 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., *Science*, 274:610–613, 1996).

The diagnostic assays offer a process for diagnosing or determining, for example, a susceptibility to infections such as bacterial, fungal, protozoan and viral infections, particularly infections caused by HIV-1 or HIV-2 through detection of a mutation in the HGPRBMY18 gene by the methods described. The invention also provides diagnostic assays for determining or monitoring susceptibility to the following conditions, diseases, or disorders: pituitary gland disorders; endocrinal diseases; breast neoplasms, breast cysts, breast dysplasia, fibrocystic mastopathy, growth disorders; benign prostatic hypertrophy; Crohn's disease, diverticular, colonic inertia, Hirschsprung's disease, colonic carcinoma, colonic tumors, chronic inflammatory colonic diseases, intestinal Behcet's disease, acute coliform mastitis, inflammatory bowel disease, Chagas' disease; bronchopulmonary dysplasia, cystic adenomatoid malformation of lung, post-inflammatory pseudotumor, pseudoneoplastic pneumonitis, lung abscess, Pancoast's syndrome; neuropathic pain; obesity; HIV infections; cancers; anorexia; bulimia, asthma; Parkinson's disease; acute heart failure; hypotension; hypertension; urinary retention; osteoporosis; angina pectoris; myocardial infarction; ulcers; asthma; allergies; benign prostatic hypertrophy; immune; metabolic; cardiovascular; and psychotic and neurological disorders, including anxiety, schizophrenia, manic depression, delirium, dementia, severe mental retardation and dyskinesias, such as Huntington's disease or Gilles dela Tourett's syndrome.

In addition, infections such as bacterial, protozoan and viral infections, particularly infections caused by HIV-1 or HIV-2; as well as, conditions or disorders such as pituitary gland disorders; endocrinal diseases; breast and prostate diseases; colon diseases; lung diseases; growth disorders, neuropathic pain; obesity; HIV infections; cancers; anorexia; bulimia, asthma; Parkinson's disease; acute heart failure; hypotension; hypertension; urinary retention; osteoporosis; angina pectoris; myocardial infarction; ulcers; asthma; allergies; benign prostatic hypertrophy; immune; metabolic; cardiovascular; and psychotic and neurological disorders, including anxiety, schizophrenia, manic depression, delirium, dementia, severe mental retardation and dyskinesias, such as Huntington's disease or Gilles dela Tourett's syndrome can be diagnosed by methods comprising determining from a sample derived from a subject having an abnormally decreased or increased level of HGPRBMY18 polypeptide or HGPRBMY18 mRNA. Decreased or increased expression can be measured at the RNA level using any of the methods well known in the art for the quantification of polynucleotides, such as, for example, PCR, RT-PCR, RNase protection, Northern blotting and other hybridization methods. Assay techniques that can be used to determine levels of a protein, such as an HGPRBMY18, in a sample derived from a host are well known to those of skill in the art. Such assay methods include radioimmunoassays, competitive-binding assays, Western Blot analysis and ELISA assays.

In another of its aspects, the present invention relates to a diagnostic kit for a disease, disorder, condition, or susceptibility to infections such as bacterial, fungal, protozoan and viral infections, particularly infections caused by HIV-1 or HIV-2 through detection of a mutation in the HGPRBMY18 gene by the methods described.

The invention also provides diagnostic assays for determining or monitoring susceptibility to the following conditions, diseases, or disorders: pituitary gland disorders; endocrinal diseases; breast diseases; prostate cancer and diseases; colon diseases; lung diseases; growth disorders, neuropathic pain; obesity; HIV infections; cancers; anorexia; bulimia, asthma; Parkinson's disease; acute heart failure; hypotension; hypertension; urinary retention; osteoporosis; angina pectoris; myocardial infarction; ulcers; asthma; allergies; benign prostatic hypertrophy; immune; metabolic; cardiovascular; and psychotic and neurological disorders, including anxiety, schizophrenia, manic depression, delirium, dementia, severe mental retardation and dyskinesias, such as Huntington's disease or Gilles dela Tourett's syndrome, which comprises:

(a) an HGPRBMY18 polynucleotide, preferably the nucleotide sequence of SEQ ID NO:1, or a fragment thereof; or (b) a nucleotide sequence complementary to that of (a); or (c) an HGPRBMY18 polypeptide, preferably the polypeptide of SEQ ID NO: 2, or a fragment thereof; or (d) an antibody to an HGPRBMY18 polypeptide, preferably to the polypeptide of SEQ ID NO: 2, or combinations thereof. It will be appreciated that in any such kit, (a), (b), (c) or (d) may comprise a substantial component and instructions are frequently included.

The GPCR polynucleotides, which may be used in the diagnostic assays according to the present invention, include oligonucleotide sequences, complementary RNA and DNA molecules, and PNAs. The polynucleotides may be used to detect and quantify HGPRBMY18-encoding nucleic acid expression in biopsied tissues in which expression (or underor overexpression) of the HGPRBMY18 polynucleotide may be correlated with disease. The diagnostic assays may be used to distinguish between the absence, presence, and excess expression of HGPRBMY18, and to monitor regulation of HGPRBMY18 polynucleotide levels during therapeutic treatment or intervention.

In a related aspect, hybridization with PCR probes which are capable of detecting polynucleotide sequences, including genomic sequences, encoding HGPRBMY18 polypeptide, or closely related molecules, may be used to identify nucleic acid sequences which encode HGPRBMY18 polypeptide. The specificity of the probe, whether it is made from a highly specific region, e.g., about 8 to 10 contiguous nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HGPRBMY18 polypeptide, alleles thereof, or related sequences.

Probes may also be used for the detection of related sequences, and should preferably contain at least 50% of the nucleotides, most optimally 15–35 nucleotides, encoding the HGPRBMY18 polypeptide. The hybridization probes of this invention may be DNA or RNA and may be derived from the nucleotide sequence of SEQ ID NO:1, or from genomic sequence including promoter, enhancer elements, and introns of the naturally occurring HGPRBMY18 protein.

Methods for producing specific hybridization probes for DNA encoding the HGPRBMY18 polypeptide include the cloning of a nucleic acid sequence that encodes the HGPRBMY18 polypeptide, or HGPRBMY18 derivatives, into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of detector/reporter groups, e.g., radionuclides such as $^{32}P$ or $^{35}S$, or enzymatic labels, such as alkaline phosphatase coupled to the probe via avidin/biotin coupling systems, and the like.

The polynucleotide sequence encoding the HGPRBMY18 polypeptide, or fragments thereof, may be used for the diagnosis of disorders associated with expression of HGPRBMY18. Examples of such disorders or conditions are described for "Therapeutics". The polynucleotide sequence encoding the HGPRBMY18 polypeptide may be used in Southern or Northern analysis, dot blot, or other membrane-based technologies; in PCR technologies; or in dip stick, pin, ELISA or chip assays utilizing fluids or tissues from patient biopsies to detect the status of, e.g., levels or overexpression of HGPRBMY18, or to detect altered HGPRBMY18 expression. Such qualitative or quantitative methods are well known in the art.

In a particular aspect, the nucleotide sequence encoding the HGPRBMY18 polypeptide may be useful in assays that detect activation or induction of various neoplasms or cancers, particularly those mentioned supra, such as colon cancers and renal tumors. The nucleotide sequence encoding the HGPRBMY18 polypeptide may be labeled by standard methods, and added to a fluid or tissue sample from a patient, under conditions suitable for the formation of hybridization complexes. After a suitable incubation period, the sample is washed and the signal is quantified and compared with a standard value. If the amount of signal in the biopsied or extracted sample is significantly altered from that of a comparable control sample, the nucleotide sequence has hybridized with nucleotide sequence present in the sample, and the presence of altered levels of nucleotide sequence encoding the HGPRBMY18 polypeptide in the sample indicates the presence of the associated disease. Such assays may also be used to evaluate the efficacy of a particular therapeutic treatment regimen in animal studies, in clinical trials, or in monitoring the treatment of an individual patient.

To provide a basis for the diagnosis of disease associated with expression of HGPRBMY18, a normal or standard profile for expression is established. This may be accomplished by combining body fluids or cell extracts taken from normal subjects, either animal or human, with a sequence, or a fragment thereof, which encodes the HGPRBMY18 polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject (patient) values is used to establish the presence of disease.

Once disease is established and a treatment protocol is initiated, hybridization assays may be repeated on a regular basis to evaluate whether the level of expression in the patient begins to approximate that which is observed in a normal individual. The results obtained from successive assays may be used to show the efficacy of treatment over a period ranging from several days to months.

With respect to cancer, the presence of an abnormal amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier, thereby preventing the development or further progression of the cancer.

Additional diagnostic uses for oligonucleotides designed from the nucleic acid sequence encoding the HGPRBMY18 polypeptide may involve the use of PCR. Such oligomers may be chemically synthesized, generated enzymatically, or produced from a recombinant source. Oligomers will preferably comprise two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers may be employed under less stringent conditions for detection and/or quantification of closely related DNA or RNA sequences.

Methods suitable for quantifying the expression of HGPRBMY18 include radiolabeling or biotinylating nucleotides, co-amplification of a control nucleic acid, and standard curves onto which the experimental results are interpolated (P. C. Melby et al., 1993, *J. Immunol. Methods*, 159:235–244; and C. Duplaa et al., 1993, *Anal. Biochem.*, 229–236). The speed of quantifying multiple samples may be accelerated by running the assay in an ELISA format where the oligomer of interest is presented in various dilutions and a spectrophotometric or colorimetric response gives rapid quantification.

Therapeutics

The HGPRBMY18 polypeptide (SEQ ID NO:2) shares homology with galanin, somatostatin, orexin, and melatonin receptors. The HGPRBMY18 protein may play a role in pituitary gland-, colon-, breast-, lung-, kidney-, and prostate-related disorders and/or in cell signaling. The HGPRBMY18 protein may further be involved in neoplastic, cardiovascular, immunological, and renal disorders.

In one embodiment of the present invention, the HGPRBMY18 protein may play a role in neoplastic disorders. An antagonist or inhibitor, or alternatively an agonist or activator, of the HGPRBMY18 polypeptide may be administered to an individual to prevent or treat a neoplastic disorder. Such disorders may include, but are not limited to, adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In a related aspect, an antibody which specifically binds to HGPRBMY18 may be used directly as an antagonist or indirectly as a targeting or delivery mechanism for bringing a pharmaceutical agent to cells or tissue which express the HGPRBMY18 polypeptide.

In another embodiment of the present invention, an antagonist or inhibitory agent, or alternatively an agonist or activating agent, of the HGPRBMY18 polypeptide may be administered to an individual to prevent or treat an immunological disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma.

In another embodiment of the present invention, an antagonist or inhibitory agent, or alternatively an agonist or activating agent, of the HGPRBMY18 polypeptide may be administered to an individual to prevent or treat a neurological disorder. Such disorders may include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, Parkinson's disease, paranoid psychoses, schizophrenia, and Tourette's disorder.

In a preferred embodiment of the present invention, an antagonist or inhibitory agent, or alternatively an agonist or activating agent, of the HGPRBMY18 polypeptide may be administered to an individual to prevent or treat a pituitary gland, colon, breast, lung, kideny, and prostate disorder. Such disorders or diseases may include, but are not limited to, Empty Sella Syndrome, hyperpituitarism, hypopituitarism, inappropriate ADH syndrome, pituitary apoplexy, pituitary neoplasms; colon carcinoma, Crohn's disease, diverticular, Hirschsprung's disease, inflammatory bowel disease, Chagas' disease; breast neoplasms, breast fibrocystic diseases; bronchopulmonary dysplasia, postinflamatory pseudotumor, pseudoneoplastic pneumonititis, Pancoast's syndrome; and prostate disease.

In another embodiment of the present invention, an antagonist or inhibitory agent, or alternatively an agonist or activating agent, of the HGPRBMY18 polypeptide may be administered to an individual to prevent or treat a renal disorder. Such disorders may include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kideny stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome, for example.

In another embodiment of the present invention, an expression vector containing the complement of the polynucleotide encoding HGPRBMY18 polypeptide may be administered to an individual to treat or prevent a neoplastic disorder, including, but not limited to, the types of cancers and tumors described above.

In another embodiment of the present invention, an expression vector containing the complement of the polynucleotide encoding HGPRBMY18 polypeptide may be administered to an individual to treat or prevent an immune disorder, including, but not limited to, the types of immune disorders described above.

In yet another embodiment of the present invention, an expression vector containing the complement of the polynucleotide encoding HGPRBMY18 polypeptide may be administered to an individual to treat or prevent a neurological disorder, including, but not limited to, the types of disorders described above.

In a preferred embodiment of the present invention, an expression vector containing the complement of the polynucleotide encoding HGPRBMY18 polypeptide may be administered to an individual to treat or prevent a pituitary gland-, colon-, breast-, kidney-, lung-, and prostate-related disorder, including, but not limited to, the types of disorders described above.

In another embodiment, the proteins, antagonists, antibodies, agonists, complementary sequences, or vectors of the present invention can be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of the HGPRBMY18 polypeptide of the present invention may be produced using methods which are generally known in the art. In particular, purified HGPRBMY18 protein, or fragments thereof, can be used to produce antibodies, or to screen libraries of pharmaceutical agents, to identify those which specifically bind HGPRBMY18.

Antibodies specific for HGPRBMY18 polypeptide, or immunogenic peptide fragments thereof, can be generated using methods that have long been known and conventionally practiced in the art. Such antibodies may include, but are not limited to, polyclonal, monoclonal, chimeric, single chain, Fab fragments, and fragments produced by an Fab expression library. Neutralizing antibodies, (i.e., those which inhibit dimer formation) are especially preferred for therapeutic use.

The following serve as non-limiting examples of peptides or fragments that may be used to generate antibodies:

MSPECARAAGDAPLRSLEQANRTRFPFFSDVKGDHRLVLAAVET,  (SEQ ID NO:20)

ARRRRRG,  (SEQ ID NO:21)

-continued

| | |
|---|---|
| RWTEAWLLGPVACH, | (SEQ ID NO:22) |
| ERMVCIVHLQRGVRGPGRRAR, | (SEQ ID NO:23) |
| RVVPQRLPGADQEISICTLIWPTIPGEISWD, | (SEQ ID NO:24) |
| KILQITKASRKRLTVSLAYSESHQIRVSQQDFRLFRT, | (SEQ ID NO:25) |
| QNFKQD,<br>and/or | (SEQ ID NO:26) |
| NPILYNMTLCRNEWKKIFCCFWFPEKGAILTDTSVKRNDLSIISG. | (SEQ ID NO:27) |

In preferred embodiments, and/or the following N-terminal HGPRBMY18 TM1-2 intertransmembrane domain deletion polypeptides are encompassed by the present invention: A1-G7 of SEQ ID NO:21. Polynucleotide sequences encoding these polypeptides are also provided. The present invention also encompasses the use of these N-terminal HGPRBMY18 TM1-2 intertransmembrane domain deletion polypeptides as immunogenic and/or antigenic epitopes as described elsewhere herein.

In preferred embodiments, and/or the following C-terminal HGPRBMY18 TM1-2 intertransmembrane domain deletion polypeptides are encompassed by the present invention: A1-G7 of SEQ ID NO:21. Polynucleotide sequences encoding these polypeptides are also provided. The present invention also encompasses the use of these C-terminal HGPRBMY18 TM1-2 intertransmembrane domain deletion polypeptides as immunogenic and/or antigenic epitopes as described elsewhere herein.

In preferred embodiments, the following N-terminal HGPRBMY18 TM2-3 intertransmembrane domain deletion polypeptides are encompassed by the present invention: R1-H14, W2-H14, T3-H14, E4-H14, A5-H14, W6-H14, L7-H14, and/or L8-H14 of SEQ ID NO:22. Polynucleotide sequences encoding these polypeptides are also provided. The present invention also encompasses the use of these N-terminal HGPRBMY18 TM2-3 intertransmembrane domain deletion polypeptides as immunogenic and/or antigenic epitopes as described elsewhere herein.

In preferred embodiments, the following C-terminal HGPRBMY18 TM2-3 intertransmembrane domain deletion polypeptides are encompassed by the present invention: R1-H14, R1-C13, R1-A12, R1-V11, R1-P10, R1-G9, R1-L8, and/or R1-L7 of SEQ ID NO:22. Polynucleotide sequences encoding these polypeptides are also provided. The present invention also encompasses the use of these C-terminal HGPRBMY18 TM2-3 intertransmembrane domain deletion polypeptides as immunogenic and/or antigenic epitopes as described elsewhere herein.

In preferred embodiments, the following N-terminal HGPRBMY18 TM3-4 intertransmembrane domain deletion polypeptides are encompassed by the present invention: E1-R21, R2-R21, M3-R21, V4-R21, C5-R21, I6-R21, V7-R21, H8-R21, L9-R21, Q10-R21, R11-R21, G12-R21, V13-R21, R14-R21, and/or G15-R21 of SEQ ID NO:23. Polynucleotide sequences encoding these polypeptides are also provided. The present invention also encompasses the use of these N-terminal HGPRBMY18 TM3-4 intertransmembrane domain deletion polypeptides as immunogenic and/or antigenic epitopes as described elsewhere herein.

In preferred embodiments, the following C-terminal HGPRBMY18 TM3-4 intertransmembrane domain deletion polypeptides are encompassed by the present invention: E1-R21, E1-A20, E1-R19, E1-R18, E1-G17, E1-P16, E1-G15, E1-R14, E1-V13, E1-G12, E1-R11, E1-Q10, E1-L9, E1-H8, and/or E1-V7 of SEQ ID NO:23. Polynucleotide sequences encoding these polypeptides are also provided. The present invention also encompasses the use of these C-terminal HGPRBMY18 TM3-4 intertransmembrane domain deletion polypeptides as immunogenic and/or antigenic epitopes as described elsewhere herein.

In preferred embodiments, the following N-terminal HGPRBMY18 TM4-5 intertransmembrane domain deletion polypeptides are encompassed by the present invention: R1-D31, V2-D31, V3-D31, P4-D31, Q5-D31, R6-D31, L7-D31, P8-D31, G9-D31, A10-D31, D11-D31, Q12-D31, E13-D31, I14-D31, S15-D31, I16-D31, C17-D31, T18-D31, L19-D31, I20-D31, W21-D31, P22-D31, T23-D31, I24-D31, and/or P25-D31 of SEQ ID NO:24. Polynucleotide sequences encoding these polypeptides are also provided. The present invention also encompasses the use of these N-terminal HGPRBMY18 TM4-5 intertransmembrane domain deletion polypeptides as immunogenic and/or antigenic epitopes as described elsewhere herein.

In preferred embodiments, the following C-terminal HGPRBMY18 TM4-5 intertransmembrane domain deletion polypeptides are encompassed by the present invention: R1-D31, R1-W30, R1-S29, R1-I28, R1-E27, R1-G26, R1-P25, R1-I24, R1-T23, R1-P22, R1-W21, R1-I20, R1-L19, R1-T18, R1-C17, R1-I16, R1-S15, R1-I14, R1-E13, R1-Q12, R1-D11, R1-A10, R1-G9, R1-P8, and/or R1-L7 of SEQ ID NO:24. Polynucleotide sequences encoding these polypeptides are also provided. The present invention also encompasses the use of these C-terminal HGPRBMY18 TM4-5 intertransmembrane domain deletion polypeptides as immunogenic and/or antigenic epitopes as described elsewhere herein.

In preferred embodiments, the following N-terminal HGPRBMY18 TM5-6 intertransmembrane domain deletion polypeptides are encompassed by the present invention: K1-T37, I2-T37, L3-T37, Q4-T37, I5-T37, T6-T37, K7-T37, A8-T37, S9-T37, R10-T37, K11-T37, R12-T37, L13-T37, T14-T37, V15-T37, S16-T37, L17-T37, A18-T37, Y19-T37, S20-T37, E21-T37, S22-T37, H23-T37, Q24-T37, I25-T37, R26-T37, V27-T37, S28-T37, Q29-T37, Q30-T37, and/or D31-T37 of SEQ ID NO:25. Polynucleotide sequences encoding these polypeptides are also provided. The present invention also encompasses the use of these N-terminal HGPRBMY18 TM5-6 intertransmembrane domain deletion polypeptides as immunogenic and/or antigenic epitopes as described elsewhere herein.

In preferred embodiments, the following C-terminal HGPRBMY18 TM5-6 intertransmembrane domain deletion polypeptides are encompassed by the present invention: K1-T37, K1-R36, K1-F35, K1-L34, K1-R33, K1-F32, K1-D31, K1-Q30, K1-Q29, K1-S28, K1-V27, K1-R26, K1-I25, K1-Q24, K1-H23, K1-S22, K1-E21, K1-S20, K1-Y19, K1-A18, K1-L17, K1-S16, K1-V15, K1-T14, K1-L13, K1-R12, K1-K11, K1-R10, K1-S9, K1-A8, and/or K1-K7 of SEQ ID NO:25. Polynucleotide sequences encoding these polypeptides are also provided. The present invention also encompasses the use of these C-terminal HGPRBMY18 TM5-6 intertransmembrane domain deletion polypeptides as immunogenic and/or antigenic epitopes as described elsewhere herein.

The HGPRBMY18 polypeptides of the present invention were determined to comprise several phosphorylation sites based upon the Motif algorithm (Genetics Computer Group, Inc.). The phosphorylation of such sites may regulate some biological activity of the HGPRBMY18 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the HGPRBMY18 polypeptide to associate with other polypeptides, particularly cognate ligand for HGPRBMY18, or its ability to modulate certain cellular signal pathways.

The HGPRBMY18 polypeptide was predicted to comprise two PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptides are encompassed by the present invention: QITKASRKRLTVS (SEQ ID NO:28), and/or ILTDTSVKRNDLS (SEQ ID NO:29). Polynucleotides encoding these polypeptides are also provided. The present invention also encompasses the use of the HGPRBMY18 PKC phosphorylation site polypeptides as immunogenic and/or antigenic epitopes as described elsewhere herein.

The HGPRBMY18 polypeptide was predicted to comprise one casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to aminoacyl-transfer RNA synthetases class-II domains may be found in reference to the following publication: Pinna L. A., Biochim. Biophys. Acta 1054:267–284(1990); which is hereby incorporated herein in its entirety.

In preferred embodiments, the following casein kinase II phosphorylation site polypeptide is encompassed by the present invention: HQIRVSQQDFRLFR (SEQ ID NO:30). Polynucleotides encoding this polypeptide are also provided. The present invention also encompasses the use of this casein kinase II phosphorylation site polypeptide as an immunogenic and/or antigenic epitope as described elsewhere herein.

The HGPRBMY18 polypeptide was predicted to comprise one cAMP- and cGMP-dependent protein kinase phosphorylation site using the Motif algorithm (Genetics Computer Group, Inc.). There has been a number of studies relative to the specificity of cAMP- and cGMP-dependent protein kinases. Both types of kinases appear to share a preference for the phosphorylation of serine or threonine residues found close to at least two consecutive N-terminal basic residues.

A consensus pattern for cAMP- and cGMP-dependent protein kinase phosphorylation sites is as follows: [RK](2)-x-[ST], wherein "x" represents any amino acid, and S or T is the phosphorylation site.

Additional information specific to cAMP- and cGMP-dependent protein kinase phosphorylation sites may be found in reference to the following publication: Fremisco J. R., Glass D. B., Krebs E. G, J. Biol. Chem. 255:4240–4245 (1980); Glass D. B., Smith S. B., J. Biol. Chem. 258: 14797–14803(1983); and Glass D. B., El-Maghrabi M. R., Pilkis S. J., J. Biol. Chem. 261:2987–2993(1986); which is hereby incorporated herein in its entirety.

In preferred embodiments, the following cAMP- and cGMP-dependent protein kinase phosphorylation site polypeptide is encompassed by the present invention: TKASRKRLTVSLAY (SEQ ID NO:31). Polynucleotides encoding this polypeptide are also provided. The present invention also encompasses the use of this cAMP- and cGMP-dependent protein kinase phosphorylation site polypeptide as an immunogenic and/or antigenic epitope as described elsewhere herein.

The HGPRBMY18 polypeptide has been shown to comprise two glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673–702(1972); Pless D. D., Lennarz W. J., Proc. Natl. Acad. Sci. U.S.A. 74:134–138(1977); Bause E., Biochem. J. 209:331–336(1983); Gavel Y., von Heijne G., Protein Eng.

3:433–442(1990); and Miletich J. P., Broze G. J. Jr., J. Biol. Chem. 265:11397–11404(1990).

In preferred embodiments, the following asparagine glycosylation site polypeptides are encompassed by the present invention: SLEQANRTRFPFFS (SEQ ID NO:32), and/or NPILYNMTLCRNEW (SEQ ID NO:33). Polynucleotides encoding these polypeptides are also provided. The present invention also encompasses the use of these HGPRBMY18 asparagine glycosylation site polypeptide as immunogenic and/or antigenic epitopes as described elsewhere herein.

The HGPRBMY18 polypeptide was predicted to comprise three N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69–99(1988); and Grand R. J. A., Biochem. J. 258:625–638(1989); which is hereby incorporated herein in its entirety.

In preferred embodiments, the following N-myristoylation site polypeptides are encompassed by the present invention: AVSLLGNVCALVLVAR (SEQ ID NO:34), RRRRRGATACLVLNLF (SEQ ID NO:35), and/or WFPEKGAILTDTSVKR (SEQ ID NO:36). The present invention also encompasses the use of these N-myristoylation site polypeptides as immunogenic and/or antigenic epitopes as described elsewhere herein.

G-protein coupled receptors (also called R7G) are an extensive group of hormones, neurotransmitters, odorants and light receptors which transduce extracellular signals by interaction with guanine nucleotide-binding (G) proteins. Some examples of receptors that belong to this family are provided as follows: 5hydroxytryptamine (serotonin) 1A to 1F, 2A to 2C, 4, 5A, 5B, 6 and 7, Acetylcholine, muscarinic-type, M1 to M5, Adenosine A1, A2A, A2B and A3, Adrenergic alpha-1A to –1C; alpha-2A to –2D; beta-1 to –3, Angiotensin II types I and II, Bombesin subtypes 3 and 4, Bradykinin B1 and B2, c3a and C5a anaphylatoxin, Cannabinoid CB1 and CB2, Chemokines C-C CC-CKR-1 to CC-CKR-8, Chemokines C-X-C CXC-CKR-1 to CXC-CKR-4, Cholecystokinin-A and cholecystokinin-B/gastrin, Dopamine D1 to D5, Endothelin ET-a and ET-b, fMet-Leu-Phe (FMLP) (N-formyl peptide), Follicle stimulating hormone (FSH-R), Galanin, Gastrin-releasing peptide (GRP-R), Gonadotropin-releasing hormone (GNRH-R), Histamine H1 and H2 (gastric receptor 1), Lutropin-choriogonadotropic hormone (LSH-R), Melanocortin MC1R to MC5R, Melatonin, Neuromedin B (NMB-R), Neuromedin K (NK-3R), Neuropeptide Y types 1 to 6, Neurotensin (NT-R), Octopamine (tyramine) from insects, Odorants, Opioids delta-, kappa- and mu-types, Oxytocin (OT-R), Platelet activating factor (PAF-R), Prostacyclin, Prostaglandin D2, Prostaglandin E2, EP1 to EP4 subtypes, Prostaglandin F2, Purinoreceptors (ATP), Somatostatin types 1 to 5, Substance-K (NK-2R), Substance-P (NK-1R), Thrombin, Thromboxane A2, Thyrotropin (TSH-R), Thyrotropin releasing factor (TRH-R), Vasopressin V1a, V1b and V2, Visual pigments (opsins and rhodopsin), Proto-oncogene mas, *Caenorhabditis elegans* putative receptors C06G4.5, C38C10.1, C43C3.2, T27D1.3 and ZC84.4, Three putative receptors encoded in the genome of cytomegalovirus: US27, US28, and UL33., ECRF3, a putative receptor encoded in the genome of herpesvirus saimiri.

The structure of all GPCRs are thought to be identical. They have seven hydrophobic regions, each of which most probably spans the membrane. The N-terminus is located on the extracellular side of the membrane and is often glycosylated, while the C-terminus is cytoplasmic and generally phosphorylated. Three extracellular loops alternate with three intracellular loops to link the seven transmembrane regions. Most, but not all of these receptors, lack a signal peptide. The most conserved parts of these proteins are the transmembrane regions and the first two cytoplasmic loops. A conserved acidic-Arg-aromatic triplet is present in the N-terminal extremity of the second cytoplasmic loop and could be implicated in the interaction with G proteins.

Additional information relating to G-protein coupled receptors may be found in reference to the following publications: Strosberg A. D., Eur. J. Biochem. 196:1–10(1991); Kerlavage A. R., Curr. Opin. Struct. Biol. 1:394–401(1991); Probst W. C., Snyder L. A., Schuster D. I., Brosius J., Sealfon S. C., DNA Cell Biol. 11:1–20(1992); Savarese T. M., Fraser C. M., Biochem. J. 283:1–9(1992); Branchek T., Curr. Biol. 3:315–317(1993); Stiles G. L., J. Biol. Chem. 267:6451–6454(1992); Friell T., Kobilka B. K., Lefkowitz R. J., Caron M. G., Trends Neurosci. 11:321–324(1988); Stevens C. F., Curr. Biol. 1:20–22(1991); Sakurai T., Yanagisawa M., Masaki T., Trends Pharmacol. Sci. 13:103–107 (1992); Salesse R., Remy J. J., Levin J. M., Jallal B., Garnier J., Biochimie 73:109–120(1991); Lancet D., Ben-Arie N., Curr. Biol. 3:668–674(1993); Uhl G. R., Childers S., Pasternak G., Trends Neurosci. 17:89–93(1994); Barnard E. A., Burnstock G., Webb T. E., Trends Pharmacol. Sci. 15:67–70 (1994); Applebury M. L., Hargrave P. A., Vision Res. 26:1881–1895(1986); Attwood T. K., Eliopoulos E. E., Findlay J. B. C., and Gene 98:153–159(1991).

For the production of antibodies, various hosts including goats, rabbits, sheep, rats, mice, humans, and others, can be immunized by injection with HGPRBMY18 polypeptide, or any fragment or oligopeptide thereof, which has immunogenic properties. Depending on the host species, various adjuvants may be used to increase the immunological response. Non-limiting examples of suitable adjuvants include Freund's (complete and incomplete), mineral gels such as aluminum hydroxide or silica, and surface-active substances such as lysolecithin, pluronic polyols, polyanions, peptides, oil emulsions, KLH, and dinitrophenol. Adjuvants typically used in humans include BCG (bacilli Calmette Guérin) and *Corynebacterium parvum*.

Preferably, the peptides, fragments, or oligopeptides used to induce antibodies to HGPRBMY18 polypeptide (i.e., immunogens) have an amino acid sequence having at least five amino acids, and more preferably, at least 7–10 amino acids. It is also preferable that the immunogens are identical to a portion of the amino acid sequence of the natural protein; they may also contain the entire amino acid sequence of a small, naturally occurring molecule. The peptides, fragments or oligopeptides may comprise a single epitope or antigenic determinant or multiple epitopes. Short stretches of HGPRBMY18 amino acids may be fused with those of another protein, such as KLH, and antibodies are produced against the chimeric molecule.

Monoclonal antibodies to HGPRBMY18 polypeptide, or immunogenic fragments thereof, may be prepared using any technique which provides for the production of antibody molecules by continuous cell lines in culture. These include, but are not limited to, the hybridoma technique, the human B-cell hybridoma technique, and the EBV-hybridoma technique (G. Kohler et al., 1975, Nature, 256:495–497; D. Kozbor et al., 1985, J. Immunol. Methods, 81:31–42; R. J. Cote et al., 1983, Proc. Natl. Acad. Sci. USA, 80:2026–2030; and S. P. Cole et al., 1984, Mol. Cell Biol., 62:109–120). The production of monoclonal antibodies is well known and routinely used in the art.

In addition, techniques developed for the production of "chimeric antibodies," the splicing of mouse antibody genes to human antibody genes to obtain a molecule with appropriate antigen specificity and biological activity can be used (S. L. Morrison et al., 1984, Proc. Natl. Acad. Sci. USA, 81:6851–6855; M. S. Neuberger et al., 1984, Nature, 312: 604–608; and S. Takeda et al., 1985, Nature, 314:452–454). Alternatively, techniques described for the production of single chain antibodies may be adapted, using methods known in the art, to produce HGPRBMY18 polypeptide-specific single chain antibodies. Antibodies with related specificity, but of distinct idiotypic composition, may be generated by chain shuffling from random combinatorial immunoglobulin libraries (D. R. Burton, 1991, Proc. Natl. Acad. Sci. USA, 88:11120–3). Antibodies may also be produced by inducing in vivo production in the lymphocyte population or by screening recombinant immunoglobulin libraries or panels of highly specific binding reagents as disclosed in the literature (R. Orlandi et al., 1989, Proc. Natl. Acad. Sci. USA, 86:3833–3837 and G. Winter et al., 1991, Nature, 349:293–299).

Antibody fragments, which contain specific binding sites for HGPRBMY18 polypeptide, may also be generated. For example, such fragments include, but are not limited to, F(ab')$_2$ fragments which can be produced by pepsin digestion of the antibody molecule and Fab fragments which can be generated by reducing the disulfide bridges of the F(ab')$_2$ fragments. Alternatively, Fab expression libraries may be constructed to allow rapid and easy identification of monoclonal Fab fragments with the desired specificity (W. D. Huse et al., 1989, Science, 254.1275–1281).

Various immunoassays can be used for screening to identify antibodies having the desired specificity. Numerous protocols for competitive binding or immunoradiometric assays using either polyclonal or monoclonal antibodies with established specificities are well known in the art. Such immunoassays typically involve measuring the formation of complexes between HGPRBMY18 polypeptide and its specific antibody. A two-site, monoclonal-based immunoassay utilizing monoclonal antibodies reactive with two non-interfering HGPRBMY18 polypeptide epitopes is preferred, but a competitive binding assay may also be employed (Maddox, supra).

Another aspect of the invention relates to a method for inducing an immunological response in a mammal which comprises inoculating the mammal with HGPRBMY18 polypeptide, or a fragment thereof, adequate to produce antibody and/or T cell immune response to protect said animal from infections such as bacterial, fungal, protozoan and viral infections, particularly infections caused by HIV-1 or HIV-2. Yet another aspect of the invention relates to a method of inducing immunological response in a mammal which comprises, delivering HGPRBMY18 polypeptide via a vector directing expression of HGPRBMY18 polynucleotide in vivo in order to induce such an immunological response to produce antibody to protect said animal from diseases.

A further aspect of the invention relates to an immunological/vaccine formulation (composition) which, when introduced into a mammalian host, induces an immunological response in that mammal to an HGPRBMY18 polypeptide wherein the composition comprises an HGPRBMY18 polypeptide or HGPRBMY18 gene. The vaccine formulation may further comprise a suitable carrier. Since the HGPRBMY18 polypeptide may be broken down in the stomach, it is preferably administered parenterally (including subcutaneous, intramuscular, intravenous, intradermal, etc., injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials, and may be stored in a freeze-dried condition requiring only the addition of the sterile liquid carrier immediately prior to use. The vaccine formulation may also include adjuvant systems for enhancing the immunogenicity of the formulation, such as oil-in-water systems and other systems known in the art. The dosage will depend on the specific activity of the vaccine and can be readily determined by routine experimentation.

In an embodiment of the present invention, the polynucleotide encoding the HGPRBMY18 polypeptide, or any fragment or complement thereof, may be used for therapeutic purposes. In one aspect, antisense, to the polynucleotide encoding the HGPRBMY18 polypeptide, may be used in situations in which it would be desirable to block the transcription of the mRNA. In particular, cells may be transformed with sequences complementary to polynucleotides encoding HGPRBMY18 polypeptide. Thus, complementary molecules may be used to modulate HGPRBMY18 polynucleotide and polypeptide activity, or to achieve regulation of gene function. Such technology is now well known in the art, and sense or antisense oligomers or oligonucleotides, or larger fragments, can be designed from various locations along the coding or control regions of polynucleotide sequences encoding HGPRBMY18 polypeptide.

Expression vectors derived from retroviruses, adenovirus, herpes or vaccinia viruses, or from various bacterial plasmids may be used for delivery of nucleotide sequences to the targeted organ, tissue or cell population. Methods, which are well known to those skilled in the art, can be used to construct recombinant vectors which will express a nucleic acid sequence that is complementary to the nucleic acid sequence encoding the HGPRBMY18 polypeptide. These techniques are described both in J. Sambrook et al., supra and in F. M. Ausubel et al., supra.

Polypeptides used in treatment can also be generated endogenously in the subject, in treatment modalities often referred to as "gene therapy". Thus for example, cells from a subject may be engineered with a polynucleotide, such as DNA or RNA, to encode a polypeptide ex vivo, and for example, by the use of a retroviral plasmid vector. The cells can then be introduced into the subject.

The genes encoding the HGPRBMY18 polypeptide can be turned off by transforming a cell or tissue with an expression vector that expresses high levels of an HGPRBMY18 polypeptide-encoding polynucleotide, or a fragment thereof. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and even longer if appropriate replication elements are designed to be part of the vector system.

Modifications of gene expression can be obtained by designing antisense molecules or complementary nucleic acid sequences (DNA, RNA, or PNA), to the control, 5', or regulatory regions of the gene encoding the HGPRBMY18 polypeptide, (e.g., signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described (see, for example, J. E. Gee et al., 1994, In: B. E. Huber and B. I. Carr, Molecular and Immunologic Approaches, Futura Publishing Co., Mt. Kisco, N.Y.). The antisense molecule or complementary sequence may also be designed to block translation of mRNA by preventing the transcript from binding to ribosomes.

Ribozymes, i.e., enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Suitable examples include engineered hammerhead motif ribozyme molecules that can specifically and efficiently catalyze endonucleolytic cleavage of sequences encoding HGPRBMY18 polypeptide.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes according to the invention may be prepared by any method known in the art for the synthesis of nucleic acid molecules. Such methods include techniques for chemically synthesizing oligonucleotides, for example, solid phase phosphoramidite chemical synthesis. Alternatively, RNA molecules may be generated by in vitro and in vivo transcription of DNA sequences encoding HGPRBMY18. Such DNA sequences may be incorporated into a wide variety of vectors with suitable RNA polymerase promoters such as T7 or SP. Alternatively, the cDNA constructs that constitutively or inducibly synthesize complementary RNA can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl, rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytosine, guanine, thymine, and uridine which are not as easily recognized by endogenous endonucleases.

Many methods for introducing vectors into cells or tissues are available and are equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods, which are well known in the art.

Any of the therapeutic methods described above may be applied to any individual in need of such therapy, including, for example, mammals such as dogs, cats, cows, horses, rabbits, monkeys, and most preferably, humans.

A further embodiment of the present invention embraces the administration of a pharmaceutical composition, in conjunction with a pharmaceutically acceptable carrier, diluent, or excipient, for any of the above-described therapeutic uses and effects. Such pharmaceutical compositions may comprise HGPRBMY18 nucleic acid, polypeptide, or peptides, antibodies to HGPRBMY18 polypeptide, mimetics, agonists, antagonists, or inhibitors of HGPRBMY18 polypeptide or polynucleotide. The compositions may be administered alone, or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients (i.e., the HGPRBMY18 nucleic acid or polypeptide, or functional fragments thereof), the pharmaceutical compositions may contain suitable pharmaceutically acceptable carriers or excipients comprising auxiliaries which facilitate processing of the active compounds into preparations which can be used pharmaceutically. Further details on techniques for formulation and administration are provided in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained by the combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyl-methylcellulose, or sodium carboxymethylcellulose; gums, including arabic and tragacanth, and proteins such as gelatin and collagen. If desired, disintegrating or solubilizing agents may be added, such as cross-linked polyvinyl pyrrolidone, agar, alginic acid, or a physiologically acceptable salt thereof, such as sodium alginate.

Dragee cores may be used in conjunction with physiologically suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification, or to characterize the quantity of active compound, i.e., dosage.

Pharmaceutical preparations, which can be used orally, include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances, which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

For topical or nasal administration, penetrants or permeation agents that are appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, combined with a buffer prior to use. After the pharmaceutical compositions have been prepared, they can be placed in an appropriate container and labeled for treatment of an indicated condition. For administration of HGPRBMY18 product, such labeling would include amount, frequency, and method of administration.

Pharmaceutical compositions suitable for use in the present invention include compositions wherein the active ingredients are contained in an effective amount to achieve the intended purpose. The determination of an effective dose or amount is well within the capability of those skilled in the art. For any compound, the therapeutically effective dose can be estimated initially either in cell culture assays, e.g., using neoplastic cells, or in animal models, usually mice, rabbits, dogs, or pigs. The animal model may also be used to determine the appropriate concentration range and route of administration. Such information can then be used and extrapolated to determine useful doses and routes for administration in humans.

A therapeutically effective dose refers to that amount of active ingredient, for example, HGPRBMY18 polypeptide, or fragments thereof, antibodies to HGPRBMY18 polypeptide, agonists, antagonists or inhibitors of HGPRBMY18 polypeptide, which ameliorates, reduces, or eliminates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $LD_{50}/ED_{50}$. Pharmaceutical compositions which exhibit large therapeutic indices are preferred. The data obtained from cell culture assays and animal studies are used in determining a range of dosages for human use. Preferred dosage contained in a pharmaceutical composition is within a range of circulating concentrations that include the $ED_{50}$ with little or no toxicity. The dosage varies within this range depending upon the dosage form employed, sensitivity of the patient, and the route of administration.

The practitioner, who will consider the factors related to the individual requiring treatment, will determine the exact dosage. Dosage and administration are adjusted to provide sufficient levels of the active moiety or to maintain the desired effect. Factors, which may be taken into account, include the severity of the individual's disease state, general health of the patient, age, weight, and gender of the patient, diet, time and frequency of administration, drug combination(s), reaction sensitivities, and tolerance/response to therapy. As a general guide, long-acting pharmaceutical compositions may be administered every 3 to 4 days, every week, or once every two weeks, depending on half-life and clearance rate of the particular formulation. Variations in these dosage levels can be adjusted using standard empirical routines for optimization, as is well understood in the art.

Normal dosage amounts may vary from 0.1 to 100,000 micrograms (μg), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors. Similarly, delivery of polynucleotides or polypeptides will be specific to particular cells, conditions, locations, and the like.

In another embodiment of the present invention, antibodies which specifically bind to the HGPRBMY18 polypeptide may be used for the diagnosis of conditions or diseases characterized by expression (or overexpression) of the HGPRBMY18 polynucleotide or polypeptide, or in assays to monitor patients being treated with the HGPRBMY18 polypeptide, or its agonists, antagonists, or inhibitors. The antibodies useful for diagnostic purposes may be prepared in the same manner as those described above for use in therapeutic methods. Diagnostic assays for the HGPRBMY18 polypeptide, homologue or antibody-reactive fragment thereof, include methods, which utilize the antibody and a label to detect the protein in human body fluids or extracts of cells or tissues. The antibodies may be used with or without modification, and may be labeled by joining them, either covalently or non-covalently, with a reporter molecule. A wide variety of reporter molecules, which are known in the art, may be used, several of which are described above. In particular, a method of detecting a G-protein coupled receptor, homologue, or an antibody-reactive fragment thereof, in a sample, comprising: a) contacting the sample with an antibody specific for the polypeptide, or an antigenic fragment thereof, under conditions in which an antigen-antibody complex can form between the antibody and the polypeptide or antigenic fragment thereof in the sample; and b) detecting an antigen-antibody complex formed in step (a), wherein detection of the complex indicates the presence of an antigenic fragment thereof, in the sample.

Several assay protocols including ELISA, RIA, and FACS for measuring HGPRBMY18 polypeptide are known in the art and provide a basis for diagnosing altered or abnormal levels of HGPRBMY18 polypeptide expression. Normal or standard values for HGPRBMY18 polypeptide expression are established by combining body fluids or cell extracts taken from normal mammalian subjects, preferably human, with antibody to the HGPRBMY18 polypeptide under conditions suitable for complex formation. The amount of standard complex formation may be quantified by various methods; photometric means are preferred. Quantities of HGPRBMY18 polypeptide expressed in subject sample, control sample, and disease samples from biopsied tissues are compared with the standard values. Deviation between standard and subject values establishes the parameters for diagnosing disease.

Microarrays and Screening Assays

In another embodiment of the present invention, oligonucleotides, or longer fragments derived from the HGPRBMY18 polynucleotide sequence described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of a disease, to diagnose disease, and to develop and monitor the activities of therapeutic agents. In a particular aspect, the microarray is prepared and used according to the methods described in WO 95/11995 (Chee et al.); D. J. Lockhart et al., 1996, *Nature Biotechnology*, 14:1675–1680; and M. Schena et al., 1996, *Proc. Natl. Acad. Sci. USA*, 93:10614–10619). Microarrays are further described in U.S. Pat. No. 6,015,702 to P. Lal et al.

In another embodiment of this invention, the nucleic acid sequence, which encodes the HGPRBMY18 polypeptide, may also be used to generate hybridization probes, which are useful for mapping the naturally occurring genomic sequence. The sequences may be mapped to a particular chromosome, to a specific region of a chromosome, or to artificial chromosome constructions (HACs), yeast artificial chromosomes (YACs), bacterial artificial chromosomes (BACs), bacterial PI constructions, or single chromosome cDNA libraries, as reviewed by C. M. Price, 1993, *Blood Rev.*, 7:127–134 and by B. J. Trask, 1991, *Trends Genet.*, 7:149–154.

Fluorescent In Situ Hybridization (FISH), (as described in I. Verma et al., 1988, *Human Chromosomes: A Manual of Basic Techniques* Pergamon Press, New York, N.Y.) may be correlated with other physical chromosome mapping techniques and genetic map data. Examples of genetic map data can be found in numerous scientific journals, or at Online Mendelian Inheritance in Man (OMIM). Correlation between the location of the gene encoding the HGPRBMY18 polypeptide on a physical chromosomal map and a specific disease, or predisposition to a specific disease, may help delimit the region of DNA associated with that genetic disease. The nucleotide sequences, particularly that of SEQ ID NO:1, or fragments thereof, according to this invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers, even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (R. A. Gatti et al., 1988, *Nature*, 336: 577–580), any sequences mapping to that area may represent associated or regulatory genes for further investigation. The nucleotide sequence of the present invention may also be used to detect differences in the chromosomal location due to translocation, inversion, and the like, among normal, carrier, or affected individuals.

In another embodiment of the present invention, the HGPRBMY18 polypeptide, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HGPRBMY18 polypeptide, or portion thereof, and the agent being tested, may be measured utilizing techniques commonly practiced in the art. In particular, a method of screening a library of molecules or compounds with an HGPRBMY18 polynucleotide, or fragment thereof, to identify at least one molecule or compound therein which specifically binds to the G-protein coupled receptor polynucleotide sequence, preferably the HGPRBMY18 polynucleotide sequence, or fragment thereof, comprising: a) combining the G-protein coupled receptor polynucleotide, or fragment thereof, with a library of molecules or compounds under conditions to allow specific binding; and b) detecting specific binding, thereby identifying a molecule or compound, which specifically binds to a G-protein coupled receptor-encoding polynucleotide sequence. In a further embodiment, the screening method is a high throughput screening method. Preferably, the library is selected from the group consisting of DNA molecules, RNA molecules, artificial chromosome constructions, PNAs, peptides and proteins. In another preferred embodiment, the candidate small molecules or compounds are a drug or therapeutic.

In yet another embodiment, a method of screening for candidate compounds capable of modulating activity of a G-protein coupled receptor-encoding polypeptide, comprising: a) contacting a test compound with a cell or tissue expressing the G-protein coupled receptor polypeptide, homologue, or fragment thereof; and b) selecting as candidate modulating compounds those test compounds that modulate activity of the G-protein coupled receptor polypeptide. Preferably, the candidate compounds are agonists or antagonists of G-protein coupled receptor activity. More preferably, the polypeptide activity is associated with the pituitary gland.

Another technique for drug screening, which may be used, provides for high throughput screening of compounds having suitable binding affinity to the protein of interest as described in WO 84/03564 (Venton, et al.). In this method, as applied to the HGPRBMY18 protein, large numbers of different small test compounds are synthesized on a solid substrate, such as plastic pins or some other surface. The test compounds are reacted with the HGPRBMY18 polypeptide, or fragments thereof, and washed. Bound HGPRBMY18 polypeptide is then detected by methods well known in the art. Purified HGPRBMY18 polypeptide can also be coated directly onto plates for use in the aforementioned drug screening techniques. Alternatively, non-neutralizing antibodies can be used to capture the peptide and immobilize it on a solid support.

In a further embodiment of this invention, competitive drug screening assays can be used in which neutralizing antibodies, capable of binding the HGPRBMY18 polypeptide, specifically compete with a test compound for binding to the HGPRBMY18 polypeptide. In this manner, the antibodies can be used to detect the presence of any peptide, which shares one or more antigenic determinants with the HGPRBMY18 polypeptide.

Other screening and small molecule (e.g., drug) detection assays which involve the detection or identification of small molecules or compounds that can bind to a given protein, i.e., the HGPRBMY18 polypeptide, are encompassed by the present invention. Particularly preferred are assays suitable for high throughput screening methodologies. In such binding-based screening or detection assays, a functional assay is not typically required. All that is needed is a target protein, preferably substantially purified, and a library or panel of compounds (e.g., ligands, drugs, small molecules) to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, HGPRBMY18 polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

EXAMPLES

The Examples herein are meant to exemplify the various aspects of carrying out the invention and are not intended to limit the scope of the invention in any way. The Examples do not include detailed descriptions for conventional methods employed, such as in the construction of vectors, the insertion of cDNA into such vectors, or the introduction of the resulting vectors into the appropriate host. Such methods are well known to those skilled in the art and are described in numerous publications, for example, Sambrook, Fritsch, and Maniatis, *Molecular Cloning: a Laboratory Manual*, 2$^{nd}$ Edition, Cold Spring Harbor Laboratory Press, USA, (1989).

Example 1

Bioinformatics Analysis

G-protein coupled receptor sequences were used as a probe to search the Incyte and public domain EST databases. The search program used was gapped BLAST (S. F. Altschul, et al., *Nuc. Acids Res.*, 25:3389–4302 (1997)). The top EST hits from the BLAST results were searched back against the non-redundant protein and patent sequence databases. From this analysis, ESTs encoding potential novel GPCRs were identified based on sequence homology. The Incyte EST (CloneID:5029478) was selected as a potential novel GPCR candidate, called HGPRBMY18, for subsequent analysis. This EST was sequenced and the full-length clone of this GPCR was obtained using the EST sequence information and conventional methods. The complete protein sequence of HGPRBMY18 was analyzed for potential transmembrane domains. The TMPRED program (K. Hofmann and W. Stoffel, Biol. Chem., 347:166 (1993)) was used for transmembrane prediction. The program predicted seven transmembrane domains and the predicted domains match with the predicated transmembrane domains of related GPCRs at the sequence level. Based on sequence, structure and known GPCR signature sequences, the orphan protein, HGPRBMY18, of the present invention, is a novel human GPCR.

Example 2

Cloning of the Novel Human GPCR HGPRBMY18

Using the EST sequence, an antisense 80 base pair oligonucleotide with biotin on the 5' end was designed that was complementary to the putative coding region of HGPRBMY18 as follows: 5'-b-AGC AGG TGG TCG CCC TTG ACG TCG GAG AAG AAG GGA AAG CGG GTG CGG TTG GCT TGC TCC AAG GTG AAG AAG GGC GCG TA-3' (SEQ ID NO:5). This biotinylated oligo was incubated with a mixture of single-stranded covalently closed circular cDNA libraries, which contained DNA corresponding to the sense strand. Hybrids between the biotinylated oligo and the circular cDNA were captured on streptavidin magnetic beads. Upon thermal release of the cDNA from the biotinylated oligo, the single stranded cDNA was converted into double strands using a primer homologous to a sequence on the cDNA cloning vector. The double stranded cDNA was introduced into *E. coli* by electroporation and the resulting colonies were screened by PCR, using a primer pair designed from the EST sequence to identify the properly oriented cDNA.

Oligos used to identify the cDNA by PCR were as follows:

```
HGPRBMY18s (SEQ ID NO:6)
5'-GACTGCCTGCCTGGTACTCAA-3'; and

HGPRBMY18a (SEQ ID NO:7)
5'-GCCAAGCGTGAGGATGGT-3'
```

The inserts of cDNA clones that were positive by PCR were sized, and two of the largest clones (both approximately 3.0 Kb) were sequenced using conventional sequencing methods. Both clones had identical sequence.

Example 3

Expression Profiling of Novel Human GPCR, HGPRBMY18

The same PCR primer pair used to identify HGPRBMY18 cDNA clones (HGPRBMY18s- SEQ ID NO:6 and HGPRBMY18a- SEQ ID NO:7) was used to measure the steady state levels of mRNA by quantitative PCR. Briefly, first strand cDNA was made from commercially available mRNA (Clontech; Palo Alto, Calif.). The relative amount of cDNA used in each assay (2.5 ng of cDNA per assay) was determined by performing a parallel experiment using a primer pair for the cyclophilin gene, which is expressed in equal amounts in all tissues. The cyclophilin primer pair detected small variations in the amount of cDNA in each sample, and these data were used for normalization of the data obtained with the primer pair for HGPRBMY18. The PCR data were converted into a relative assessment of the difference in transcript abundance among the tissues tested and the data are presented in FIG. 7. Transcripts corresponding to the orphan GPCR, HGPRBMY18, were found to be highly expressed in pituitary gland.

Example 4

Quantitative PCR Expression Profiling of HGPRBMY18

The same PCR primer pair that was used to identify HGPRBMY18 (also referred to GPCR38) cDNA clones was used to measure the steady state levels of mRNA by quantitative PCR.

```
GPCR38-2s 5'-TCTGCCTCTCTGCGTCTTC-3'  (SEQ ID NO:37)

GPCR38-2a 5'-AGTCCTGGCACCAAGAAGTT-3' (SEQ ID NO:38)
```

Briefly, first strand cDNA was made from commercially available mRNA (Clontech) and subjected to real time quantitative PCR using a PE 5700 instrument (Applied Biosystems; Foster City, Calif.) which detects the amount of DNA amplified during each cycle by the fluorescent output of SYBR green, a DNA binding dye specific for double strands. The specificity of the primer pair for its target is verified by performing a thermal denaturation profile at the end of the run which gives an indication of the number of different DNA sequences present by determining melting temperature, Tm. In the case of the HGPRBMY18 primer pair, only one DNA fragment was detected having a homogeneous melting point. Contributions of contaminating genomic DNA to the assessment of tissue abundance is controlled for by performing the PCR with first strand made with and without reverse transcriptase. In all cases, the contribution of material amplified in the no reverse transcriptase controls was negligible.

Small variations in the amount of cDNA used in each tube was determined by performing a parallel experiment using a primer pair for a gene expressed in equal amounts in all tissues, cyclophilin. These data were used to normalize the data obtained with the HGPRBMY18 primer pair. The PCR data was converted into a relative assessment of the difference in transcript abundance amongst the tissues tested and the data are presented in bar graph form. Transcripts corresponding to HGPRBMY18 are expressed approximately 925 times greater in the pituitary gland than in most of the other tissues tested (brain, bone marrow, prostate, heart, small intestine, kidney, liver spleen, lymph node and thymus. Low level expression was detected in the lung, testis, pancreas and spinal cord (see FIG. 7).

Example 5

G-Protein Coupled Receptor PCR Expression Profiling in OCLP-1

RNA quantification was performed using the Taqman® real-time-PCR fluorogenic assay. The Taqman® assay is one of the most precise methods for assaying the concentration of nucleic acid templates.

All cell lines were grown using standard conditions: RPMI 1640 supplemented with 10% fetal bovine serum, 100 IU/ml penicillin, 100 mg/ml streptomycin, and 2 mM L-glutamine, 10 mM Hepes (all from GibcoBRL; Rockville, Md.). Eighty percent confluent cells were washed twice with phosphate-buffered saline (GibcoBRL) and harvested using 0.25% trypsin (GibcoBRL). RNA was prepared using the RNeasy Maxi Kit from Qiagen (Valencia, Calif.).

cDNA template for real-time PCR was generated using the Superscript™ First Strand Synthesis system for RT-PCR.

SYBR Green real-time PCR reactions were prepared as follows: The reaction mix consisted of 20 ng first strand cDNA; 50 nM Forward Primer; 50 nM Reverse Primer; 0.75×SYBR Green I (Sigma); 1×SYBR Green PCR Buffer (50 mMTris-HCl pH8.3, 75 mM KCl); 10% DMSO; 3 mM $MgCl_2$; 300 µM each dATP, dGTP, dTTP, dCTP; 1 U Platinum®8 Taq DNA Polymerase High Fidelity (Cat# 11304-029; Life Technologies; Rockville, Md.); 1:50 dilution; ROX (Life Technologies). Real-time PCR was performed using an Applied Biosystems 5700 Sequence Detection System. Conditions were 95° C. for 10 min (denaturation and activation of Platinum® Taq DNA Polymerase), 40 cycles of PCR (95° C. for 15 sec, 60° C. for 1 min). PCR products are analyzed for uniform melting using an analysis algorithm built into the 5700 Sequence Detection System.

Forward primer: GPCR749-F: 5'-TCTGCCTCTCT-GCGTCTTC-3' (SEQ ID NO:37); and

Reverse primer: GPCR750-R: 5'-AGTCCTGGCAC-CAAGAAGTT-3' (SEQ ID NO:38).

cDNA quantification used in the normalization of template quantity was performed using Taqman® technology. Taqman® reactions are prepared as follows: The reaction mix consisted of 20 ng first strand cDNA; 25 nM GAPDH-F3, Forward Primer; 250 nM GAPDH-R1 Reverse Primer; 200 nM GAPDH-PVIC Taqman® Probe (fluorescent dye labeled oligonucleotide primer); 1× Buffer A (Applied Biosystems); 5.5 mM $MgCl_2$; 300 µM dATP, dGTP, dTTP, dCTP; 1 U Amplitaq Gold (Applied Biosystems). GAPDH, D-glyceraldehyde-3-phosphate dehydrogenase, was used as control to normalize mRNA levels.

Real-time PCR was performed using an Applied Biosystems 7700 Sequence Detection System. Conditions were 95° C. for 10 min. (denaturation and activation of Amplitaq Gold), 40 cycles of PCR (95° C. for 15 sec, 60° C. for 1 min).

The sequences for the GAPDH oligonucleotides used in the Taqman® reactions are as follows:

GAPDH-F3-5'-AGCCGAGCCACATCGCT-3' (SEQ ID NO:39)

GAPDH-R1-5'-GTGACCAGGCGCCCAATAC-3' (SEQ ID NO:40)

GAPDH-PVIC Taqman ® Probe-VIC-5'-CAAATCCGTTGACTCCGACCTTCACCTT-3' TAMRA. (SEQ ID NO:41)

The Sequence Detection System generates a Ct (threshold cycle) value that is used to calculate a concentration for each input cDNA template. cDNA levels for each gene of interest are normalized to GAPDH cDNA levels to compensate for variations in total cDNA quantity in the input sample. This is done by generating GAPDH Ct values for each cell line. Ct values for the gene of interest and GAPDH are inserted into a modified version of the δδCt equation (Applied Biosystems Prism® 7700 Sequence Detection System User Bulletin #2), which is used to calculate a GAPDH normalized relative cDNA level for each specific cDNA. The δδCt equation is as follows: relative quantity of nucleic acid template=$2^{\delta\delta Ct}=2^{(\delta Cta-\delta Ctb)}$, where δCa=Ct target–Ct GAPDH, and δCtb=Ct reference–Ct GAPDH. (No reference cell line was used for the calculation of relative quantity; δCtb was defined as 21).

Figure 8:
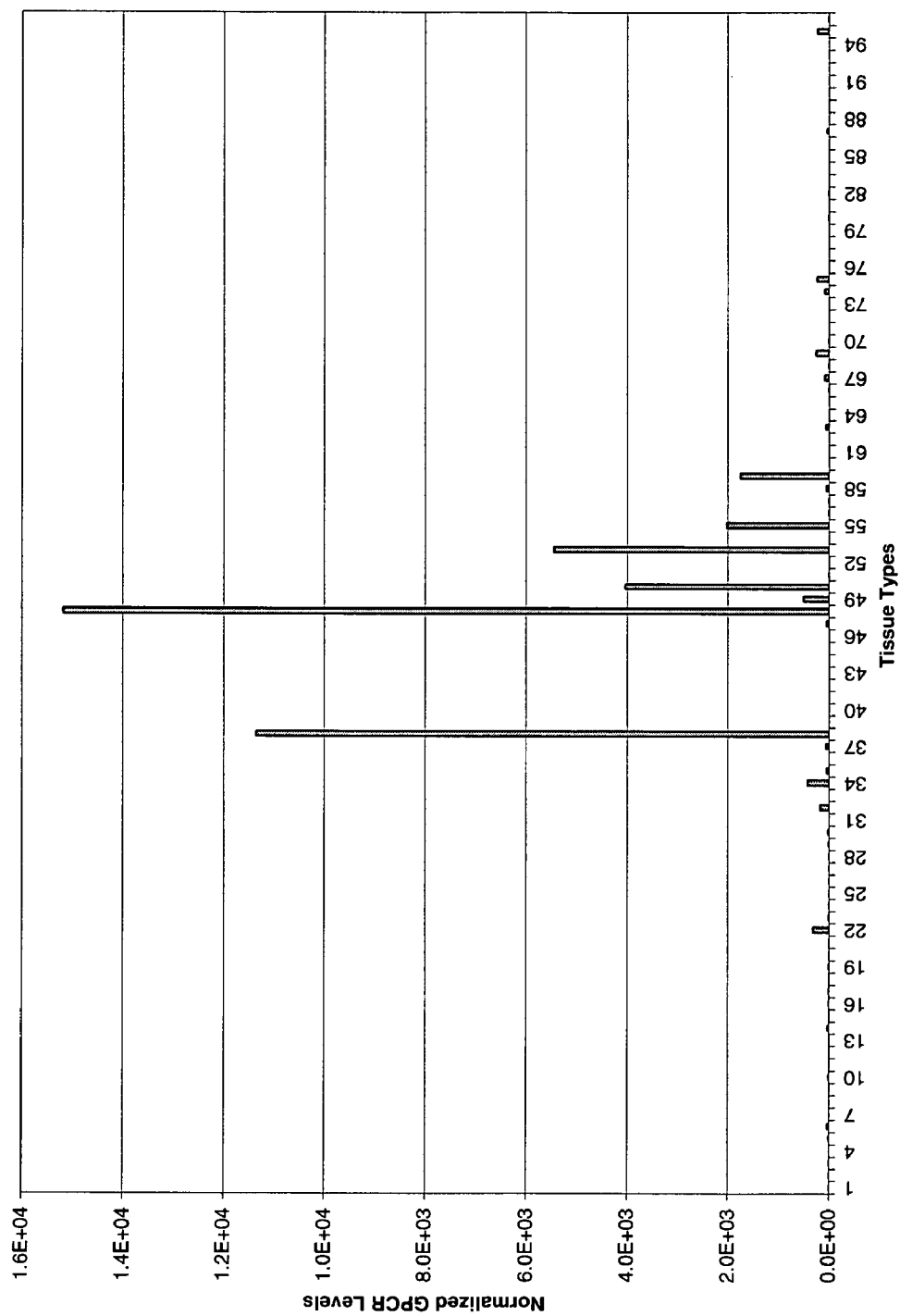
FIG. 8 shows an expression profile of the novel human orphan GPCR, HGPRBMY18, amongst a number of cancer cell lines, as described in Example 5 and Table 1.

The Graph # of Table 1 corresponds to the tissue type position number of FIG. 8. Interestingly, HGPRBMY18 (also known as GPCR38-2) was found to be expressed 20 to 600 fold greater in colon carcinoma cell lines in comparison to other cancer cell lines in the OCLP-1 (oncology cell line panel). HGPRBMY18 is also expressed at moderate levels in prostate and lung cancer cell lines.

TABLE 1

| Graph # | Name | Tissue | Ct GAPDH | Ct GPCR38-2 | dCt | ddCt | Quant. |
|---|---|---|---|---|---|---|---|
| 1 | AIN 4 | breast | 17.49 | 37.03 | 19.54 | −1.46 | 2.8E+00 |
| 2 | AIN 4T | breast | 17.15 | 36.34 | 19.19 | −1.81 | 3.5E+00 |
| 3 | AIN4/myc | breast | 17.81 | 36.33 | 18.52 | −2.48 | 5.6E+00 |
| 4 | BT-20 | breast | 17.9 | 40 | 22.1 | 1.1 | 0.0E+00 |
| 5 | BT-474 | breast | 17.65 | 35.33 | 17.68 | −3.32 | 1.0E+01 |
| 6 | BT-483 | breast | 17.45 | 33.25 | 15.8 | −5.2 | 3.7E+01 |
| 7 | BT-549 | breast | 17.55 | 39.71 | 22.16 | 1.16 | 4.5E−01 |
| 8 | DU4475 | breast | 18.1 | 38.02 | 19.92 | −1.08 | 2.1E+00 |
| 9 | H3396 | breast | 18.04 | 40 | 21.96 | 0.96 | 0.0E+00 |
| 10 | HBL100 | breast | 17.02 | 34.69 | 17.67 | −3.33 | 1.0E+01 |
| 11 | Her2 MCF-7 | breast | 19.26 | 40 | 20.74 | −0.26 | 0.0E+00 |
| 12 | HS 578T | breast | 17.83 | 40 | 22.17 | 1.17 | 0.0E+00 |
| 13 | MCF7 | breast | 17.83 | 40 | 22.17 | 1.17 | 0.0E+00 |
| 14 | MCF-7/AdrR | breast | 17.23 | 33.11 | 15.88 | −5.12 | 3.5E+01 |
| 15 | MDAH 2774 | breast | 16.87 | 38.32 | 21.45 | 0.45 | 7.3E−01 |
| 16 | MDA-MB-175-VII | breast | 15.72 | 33.67 | 17.95 | −3.05 | 8.3E+00 |
| 17 | MDA-MB-231 | breast | 17.62 | 35.5 | 17.88 | −3.12 | 8.7E+00 |
| 18 | MDA-MB-453 | breast | 17.9 | 40 | 22.1 | 1.1 | 0.0E+00 |
| 19 | MDA-MB-468 | breast | 17.49 | 35.21 | 17.72 | −3.28 | 9.7E+00 |
| 20 | Pat-21 R60 | breast | 35.59 | 40 | 4.41 | −16.59 | 0.0E+00 |
| 21 | SKBR3 | breast | 17.12 | 40 | 22.88 | 1.88 | 0.0E+00 |
| 22 | T47D | breast | 18.86 | 31.55 | 12.69 | −8.31 | 3.2E+02 |
| 23 | UACC-812 | breast | 17.06 | 35.03 | 17.97 | −3.03 | 8.2E+00 |
| 24 | ZR-75-1 | breast | 15.95 | 35.34 | 19.39 | −1.61 | 3.1E+00 |
| 25 | C-33A | cervical | 17.49 | 40 | 22.51 | 1.51 | 0.0E+00 |
| 26 | Ca Ski | cervical | 17.38 | 40 | 22.62 | 1.62 | 0.0E+00 |
| 27 | HeLa | cervical | 17.59 | 38.68 | 21.09 | 0.09 | 9.4E−01 |
| 28 | HT-3 | cervical | 17.42 | 36.9 | 19.48 | −1.52 | 2.9E+00 |
| 29 | ME-180 | cervical | 16.86 | 34.68 | 17.82 | −3.18 | 9.1E+00 |
| 30 | SiHa | cervical | 18.07 | 34.64 | 16.57 | −4.43 | 2.2E+01 |
| 31 | SW756 | cervical | 15.59 | 36.67 | 21.08 | 0.08 | 9.5E−01 |
| 32 | CACO-2 | colon | 17.56 | 31.15 | 13.59 | −7.41 | 1.7E+02 |
| 33 | CCD-112Co | colon | 18.03 | 40 | 21.97 | 0.97 | 0.0E+00 |
| 34 | CCD-33Co | colon | 17.07 | 29.35 | 12.28 | −8.72 | 4.2E+02 |
| 35 | Colo 205 | colon | 18.02 | 33.28 | 15.26 | −5.74 | 5.3E+01 |
| 36 | Colo 320DM | colon | 17.01 | 40 | 22.99 | 1.99 | 0.0E+00 |
| 37 | Colo201 | colon | 17.89 | 32.9 | 15.01 | −5.99 | 6.4E+01 |
| 38 | Cx-1 | colon | 18.79 | 26.32 | 7.53 | −13.47 | 1.1E+04 |
| 39 | ddH2O | colon | 40 | 40 | 0 | −21 | 0.0E+00 |
| 40 | HCT116 | colon | 17.59 | 40 | 22.41 | 1.41 | 3.8E−01 |
| 41 | HCT116/epo5 | colon | 17.71 | 40 | 22.29 | 1.29 | 0.0E+00 |
| 42 | HCT116/ras | colon | 17.18 | 40 | 22.82 | 1.82 | 0.0E+00 |
| 43 | HCT116/TX15CR | colon | 17.36 | 40 | 22.64 | 1.64 | 0.0E+00 |
| 44 | HCT116/vivo | colon | 17.7 | 40 | 22.3 | 1.3 | 0.0E+00 |
| 45 | HCT116/VM46 | colon | 17.87 | 40 | 22.13 | 1.13 | 0.0E+00 |
| 46 | HCT116/VP35 | colon | 17.3 | 40 | 22.7 | 1.7 | 0.0E+00 |
| 47 | HCT-8 | colon | 17.44 | 32.66 | 15.22 | −5.78 | 5.5E+01 |
| 48 | HT-29 | colon | 17.9 | 25.01 | 7.11 | −13.89 | 1.5E+04 |
| 49 | LoVo | colon | 17.64 | 29.65 | 12.01 | −8.99 | 5.1E+02 |
| 50 | LS 174T | colon | 17.93 | 26.95 | 9.02 | −11.98 | 4.0E+03 |
| 51 | LS123 | colon | 17.65 | 36.48 | 18.83 | −2.17 | 4.5E+00 |
| 52 | MIP | colon | 16.92 | 40 | 23.08 | 2.08 | 0.0E+00 |

TABLE 1-continued

| Graph # | Name | Tissue | Ct GAPDH | Ct GPCR38-2 | dCt | ddCt | Quant. |
|---|---|---|---|---|---|---|---|
| 53 | SK-CO-1 | colon | 17.75 | 26.34 | 8.59 | −12.41 | 5.4E+03 |
| 54 | SW1417 | colon | 17.22 | 40 | 22.78 | 1.78 | 0.0E+00 |
| 55 | SW403 | colon | 18.39 | 28.41 | 10.02 | −10.98 | 2.0E+03 |
| 56 | SW480 | colon | 17 | 35.76 | 18.76 | −2.24 | 4.7E+00 |
| 57 | SW620 | colon | 17.16 | 36.5 | 19.34 | −1.66 | 3.2E+00 |
| 58 | SW837 | colon | 18.35 | 33.5 | 15.15 | −5.85 | 5.8E+01 |
| 59 | T84 | colon | 16.44 | 26.67 | 10.23 | −10.77 | 1.7E+03 |
| 60 | CCD-18Co | colon, fibroblast | 17.19 | 40 | 22.81 | 1.81 | 0.0E+00 |
| 61 | HT-1080 | fibrosarcoma | 17.16 | 40 | 22.84 | 1.84 | 0.0E+00 |
| 62 | CCRF-CEM | leukemia | 17.07 | 40 | 22.93 | 1.93 | 0.0E+00 |
| 63 | HL-60 | leukemia | 17.54 | 32.57 | 15.03 | −5.97 | 6.3E+01 |
| 64 | K562 | leukemia | 18.42 | 40 | 21.58 | 0.58 | 0.0E+00 |
| 65 | A-427 | lung | 18 | 40 | 22 | 1 | 0.0E+00 |
| 66 | A549 | lung | 17.63 | 36.26 | 18.63 | −2.37 | 5.2E+00 |
| 67 | Calu-3 | lung | 18.09 | 32.52 | 14.43 | −6.57 | 9.5E+01 |
| 68 | Calu-6 | lung | 16.62 | 36.01 | 19.39 | −1.61 | 3.1E+00 |
| 69 | ChaGo-K-1 | lung | 17.79 | 30.75 | 12.96 | −8.04 | 2.6E+02 |
| 70 | DMS 114 | lung | 18.14 | 36.44 | 18.3 | −2.7 | 6.5E+00 |
| 71 | LX-1 | lung | 18.17 | 40 | 21.83 | 0.83 | 0.0E+00 |
| 72 | MRC-5 | lung | 17.3 | 40 | 22.7 | 1.7 | 0.0E+00 |
| 73 | MSTO-211H | lung | 16.81 | 40 | 23.19 | 2.19 | 0.0E+00 |
| 74 | NCI-H596 | lung | 17.73 | 32.25 | 14.52 | −6.48 | 8.9E+01 |
| 75 | SHP-77 | lung | 18.66 | 31.81 | 13.15 | −7.85 | 2.3E+02 |
| 76 | Sk-LU-1 | lung | 15.81 | 40 | 24.19 | 3.19 | 0.0E+00 |
| 77 | SK-MES-1 | lung | 17.1 | 38.33 | 21.23 | 0.23 | 8.5E−01 |
| 78 | SW1271 | lung | 16.45 | 40 | 23.55 | 2.55 | 0.0E+00 |
| 79 | SW1573 | lung | 17.14 | 40 | 22.86 | 1.86 | 0.0E+00 |
| 80 | SW900 | lung | 18.17 | 36.73 | 18.56 | −2.44 | 5.4E+00 |
| 81 | Hs 294T | melanoma | 17.73 | 38.35 | 20.62 | −0.38 | 1.3E+00 |
| 82 | A2780/DDP-R | ovarian | 21.51 | 40 | 18.49 | −2.51 | 0.0E+00 |
| 83 | A2780/DDP-S | ovarian | 17.89 | 39.81 | 21.92 | 0.92 | 5.3E−01 |
| 84 | A2780/epo5 | ovarian | 17.54 | 40 | 22.46 | 1.46 | 0.0E+00 |
| 85 | A2780/TAX-R | ovarian | 18.4 | 38.61 | 20.21 | −0.79 | 1.7E+00 |
| 86 | A2780/TAX-S | ovarian | 17.83 | 40 | 22.17 | 1.17 | 0.0E+00 |
| 87 | Caov-3 | ovarian | 15.5 | 31.17 | 15.67 | −5.33 | 4.0E+01 |
| 88 | ES-2 | ovarian | 17.22 | 40 | 22.78 | 1.78 | 0.0E+00 |
| 89 | HOC-76 | ovarian | 34.3 | 40 | 5.7 | −15.3 | 0.0E+00 |
| 90 | OVCAR-3 | ovarian | 17.09 | 37.02 | 19.93 | −1.07 | 2.1E+00 |
| 91 | PA-1 | ovarian | 17.33 | 39.44 | 22.11 | 1.11 | 4.6E−01 |
| 92 | SW 626 | ovarian | 16.94 | 39.63 | 22.69 | 1.69 | 3.1E−01 |
| 93 | UPN251 | ovarian | 17.69 | 40 | 22.31 | 1.31 | 0.0E+00 |
| 94 | LNCAP | prostate | 18.17 | 40 | 21.83 | 0.83 | 0.0E+00 |
| 95 | PC-3 | prostate | 17.25 | 30.42 | 13.17 | −7.83 | 2.3E+02 |
| 96 | A431 | squamous | 19.85 | 37.26 | 17.41 | −3.59 | 1.2E+01 |

Example 6

Method of Assessing the Expression Profile of the Novel HGPRBMY18 Polypeptides of the Present Invention Using Expanded mRNA Tissue and Cell Sources Total RNA from tissues was isolated using the TriZol protocol (Invitrogen) and quantified by determining its absorbance at 260 nM. An assessment of the 18 s and 28 s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For HGPRBMY18, the primer probe sequences were as follows:

```
Forward Primer 5'-TCACAAAGGCATCAAGGAAGAG-3'         (SEQ ID NO:46)

Reverse Primer 5'-TGGGACACGCGGATCTG-3'             (SEQ ID NO:47)

TaqMan Probe   5'-CTCTCCGAGTAGGCCAGGCTTACCGT-3'    (SEQ ID NO:48)
```

I. DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TaqMan assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+RNA. If not the RNA was not used in actual experiments.

II. Reverse Transcription Reaction and Sequence Detection 100 ng of Dnase-treated total RNA was annealed to 2.5 µM of the respective gene-specific reverse primer in the presence of 5.5 mM Magnesium Chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 2.0 µM of the TaqMan probe, 500 µM of each dNTP, buffer and 5U AmpliTaq Gold™. The PCR reaction was then held at 94° C. for 12 min, followed by 40 cycles of 94° C. for 15 sec and 60° C. for 30 sec.

III. Data Handling

Figure 9:
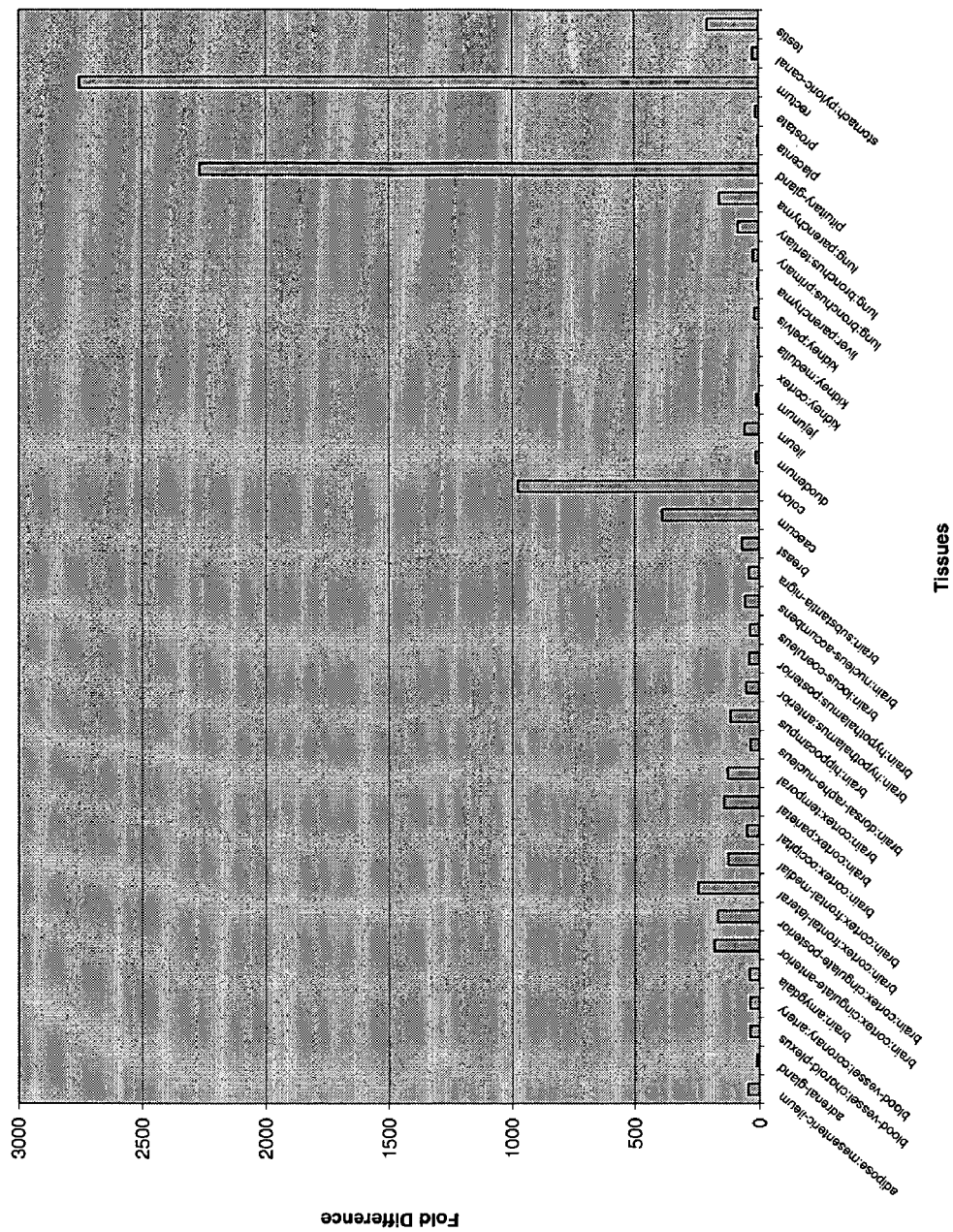
FIG. 9 shows an expanded expression profile of the novel human orphan GPCR, HGPRBMY18. The figure illustrates the relative expression level of HGPRBMY18 amongst various mRNA tissue sources. As shown, the HGPRBMY18 polypeptide was expressed predominately in the pituitary gland. HGPRBMY18 polypeptide was also significantly expressed in the rectum, colon and caecum, and to a lesser extent throughout the brain and in the breast. Expression data was obtained by measuring the steady state HGPRBMY18 mRNA levels by quantitative PCR using the PCR primer pair provided as SEQ ID NO:46 and 47, and Taqman probe (SEQ ID NO:48) as described in Example 6 herein.
Figure 11:
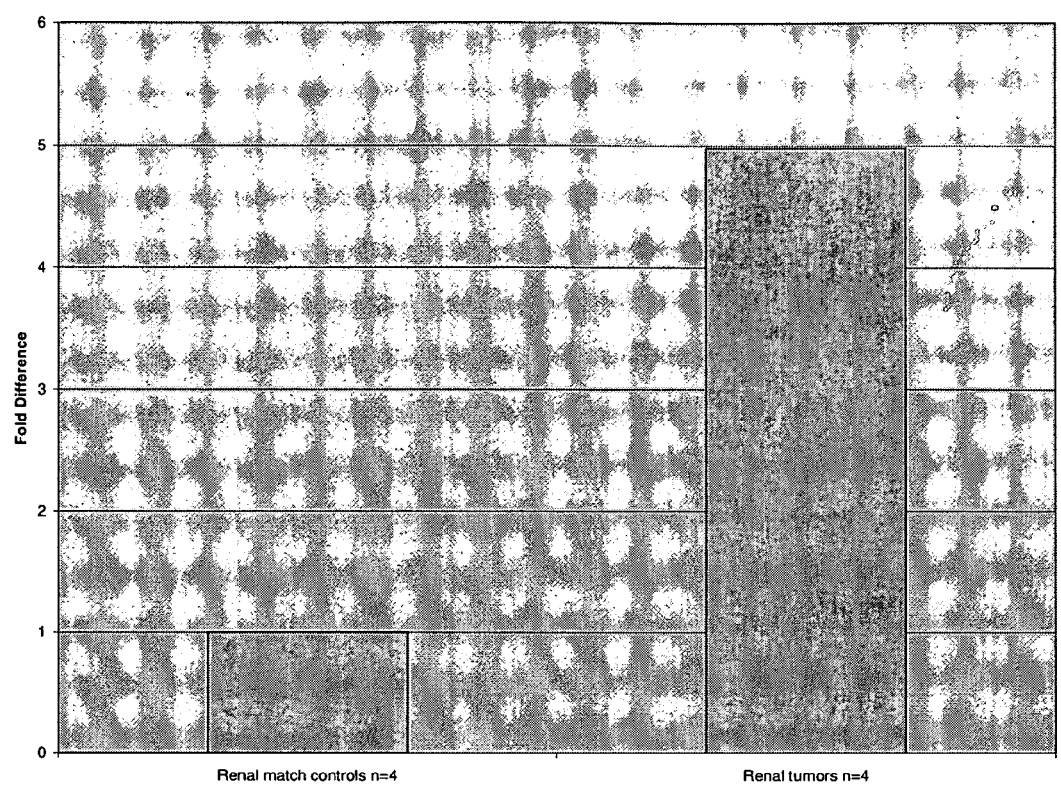
FIG. 11 shows an expanded expression profile of the novel human G-protein coupled receptor, HGPRBMY18, of the present invention. The figure illustrates the relative expression level of HGPRBMY18 amongst various mRNA tissue sources isolated from normal and tumor tissues. As shown, the HGPRBMY18 polypeptide was differentially expressed in renal tumor tissue compared to normal renal tissue. Expression data was obtained by measuring the steady state HGPRBMY18 mRNA levels by quantitative PCR using the PCR primer pair provided as SEQ ID NO:46 and 47, and Taqman probe (SEQ ID NO:48) as described in Example 6 herein.

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta ct)}$ The expanded expression profile of the HGPRBMY18 polypeptide is provided in FIGS. 9 and 11 and described elsewhere herein.

Example 7

G-Protein Coupled Receptor PCR Expression Profiling in OCLP-3

RNA quantification may be performed using the Taqman® real-time-PCR fluorogenic assay. The Taqman® assay is one of the most precise methods for assaying the concentration of nucleic acid templates. PCR primer pairs were designed to the specific gene and used to measure the steady state levels of mRNA by quantitative PCR across a panel of RNA's isolated from proliferative cell lines.

All cell lines were grown using standard conditions: RPMI 1640 supplemented with 10% fetal bovine serum, 100 IU/ml penicillin, 100 mg/ml streptomycin, and 2 mM L-glutamine, 10 mM Hepes (all from GibcoBRL; Rockville, Md.). Eighty percent confluent cells were washed twice with phosphate-buffered saline (GibcoBRL) and harvested using 0.25% trypsin (GibcoBRL). RNA was prepared using the RNeasy Maxi Kit from Qiagen (Valencia, Calif.).

Briefly, first strand cdna was made from several cell line RNA's and subjected to real time quantitative PCR using a PE7900HT instrument (Applied Biosystems, Foster City, Calif.) which detects the amount of DNA amplified during each cycle by the fluorescent output of SYBR green, a DNA binding dye specific for double stranded DNA. The specificity of the primer pairs for their targets is verified by performing a thermal denaturation profile at the end of the run which gives an indication of the number of different DNA sequences present by determining melting temperature of double stranded amplicon(s). In the experiment, only one DNA fragment of the correct TM was detected, having a homogeneous melting point.

Small variations in the amount of cDNA used in each tube was determined by performing parallel experiments using a primer pair for a gene expressed in equal amounts in all tissues, cyclophilin. these data were used to normalize the data obtained with the gene specific primer pairs. The PCR data was converted into a relative assessment of the difference in transcript abundance amongst the tissues tested and the data are presented in bar graph form for each transcript.

The formula for calculating the relative abundance is:

Relative abundance=$1^{-\Delta\Delta ct}$

Where ΔΔCt=(The Ct of the sample−the Ct for cyclophilin)−the Ct for a calibrator sample The calibrator sample is arbitrarily chosen as the tissue with the lowest abundance.

For each PCR reaction 10 µl of 2×SYBRgreen master mix (PE Biosystems) was combined with 4.9 µl water, 0.05 µl of each PCR primer (at 100 µm concentration) and 5 µl of template DNA. The PCR reactions used the following conditions:

95° C. for 10 minutes, then 40 cycles of
95° C. for 30 seconds followed by 60° C. for 1 minute
then the thermal denaturation protocol was begun at 60° C. and the fluorescence measured as the temperature increased slowly to 95° C.

The sequence of the PCR primers were as follows:

```
Forward Primer
5'-TCTGCCTCTCTGCGTCTTC-3'      (SEQ ID NO:49)

Reverse Primer
5'-AGTCCTGGCACCAAGAAGTT-3'     (SEQ ID NO:50)
```

TABLE 2

| Graph # | Name | Tissue | Fold Difference |
|---|---|---|---|
| 1 | AIN4 | breast | 6.38 |
| 2 | AIN4/myc | breast | 17.67 |
| 3 | AIN4T | breast | 6.19 |
| 4 | BT-20 | breast | 2.93 |
| 5 | BT-474 | breast | 9.73 |
| 6 | BT-549 | breast | 2.45 |
| 7 | DU4475 | breast | 5.10 |
| 8 | H3396 | breast | 3.54 |
| 9 | HBL100 | breast | 1451.06 |
| 10 | MCF7 | breast | 8.53 |
| 11 | MCF-7/AdrR | breast | 193.92 |
| 12 | MCF7/Her2 | breast | 8.68 |
| 13 | MDA-MB-175-VII | breast | 157.39 |
| 14 | MDA-MB-231 | breast | 84.22 |
| 15 | C-33A | cervical | 2.09 |
| 16 | Ca Ski | cervical | 28.05 |
| 17 | HeLa | cervical | 31.15 |
| 18 | HT-3 | cervical | 3.20 |
| 19 | ME-180 | cervical | 56.86 |
| 20 | SiHa | cervical | 5.97 |
| 21 | SW756 | cervical | 3.30 |
| 22 | CACO-2 | colon | 321.34 |
| 23 | Colo201 | colon | 252.94 |
| 24 | HCT116 | colon | 1.73 |
| 25 | HCT116/epo5 | colon | 2.23 |

TABLE 2-continued

| Graph # | Name | Tissue | Fold Difference |
|---|---|---|---|
| 26 | HCT116/ras | colon | 6.32 |
| 27 | HCT116/TX15CR | colon | 3.76 |
| 28 | HCT116/vivo | colon | 2.20 |
| 29 | HCT116/VM46 | colon | 2.78 |
| 30 | HCT116/VP35 | colon | 3.46 |
| 31 | HT-29 | colon | 64991.44 |
| 32 | LoVo | colon | 1024.05 |
| 33 | LS 174T | colon | 6502.30 |
| 34 | SK-CO-1 | colon | 19985.11 |
| 35 | SW480 | colon | 5.29 |
| 36 | SW620 | colon | 32.42 |
| 37 | HUVEC | endothelial | 15.77 |
| 38 | NCI-N87 | gastric | 10.54 |
| 39 | CCRF-CEM | leukemia | 2.98 |
| 40 | HL-60 | leukemia | 511.42 |
| 41 | Jurkat | leukemia | 15.19 |
| 42 | K-562 | leukemia | 8.59 |
| 43 | A-427 | lung | 1.03 |
| 44 | A549 | lung | 8.46 |
| 45 | Calu-3 | lung | 202.67 |
| 46 | Calu-6 | lung | 8.06 |
| 47 | ChaGo-K-1 | lung | 802.57 |
| 48 | DMS 114 | lung | 11.68 |
| 49 | LX-1 | lung | 6.67 |
| 50 | SHP-77 | lung | 476.25 |
| 51 | Sk-LU-1 | lung | 1.00 |
| 52 | SK-MES-1 | lung | 3.46 |
| 53 | SW1271 | lung | 3.68 |
| 54 | SW1573 | lung | 4.02 |
| 55 | SW900 | lung | 63.84 |
| 56 | TOTAL RNA, FETAL LUNG | lung | 106.63 |
| 57 | A-375 | melanoma | 8.39 |
| 58 | C32 | melanoma | 3.68 |
| 59 | G-361 | melanoma | 6.61 |
| 60 | Hs 294T | melanoma | 3.36 |
| 61 | SK-MEL-1 | melanoma | 78.25 |
| 62 | SK-MEL-28 | melanoma | 44.81 |
| 63 | SK-MEL-3 | melanoma | 3.18 |
| 64 | SK-MEL-5 | melanoma | 3.55 |
| 65 | WM373 | melanoma | 33.54 |
| 66 | WM852 | melanoma | 4.72 |
| 67 | A2780/DDP-R | ovarian | 2.60 |
| 68 | A2780/DDP-S | ovarian | 4.17 |
| 69 | A2780/epo5 | ovarian | 6.29 |
| 70 | A2780/TAX-R | ovarian | 5.05 |
| 71 | A2780/TAX-S | ovarian | 1.72 |
| 72 | Caov-3 | ovarian | 3.21 |
| 73 | ES-2 | ovarian | 1.72 |
| 74 | HOC-76 | ovarian | 6.19 |
| 75 | OVCAR-3 | ovarian | 367.05 |
| 76 | PA-1 | ovarian | 89.65 |
| 77 | SW626 | ovarian | 2.80 |
| 78 | TOTAL RNA, OVARY | ovarian | 454.36 |
| 79 | 22Rv1 | prostate | 12.54 |
| 80 | CA-HPV-10 | prostate | 81.90 |
| 81 | DU 145 | prostate | 26.03 |
| 82 | LNCAP | prostate | 5.63 |
| 83 | LNCaP-FGC | prostate | 5.25 |
| 84 | PC-3 | prostate | 396.95 |
| 85 | PWR-1E | prostate | 51.81 |
| 86 | RWPE-1 | prostate | 41.08 |
| 87 | RWPE-2 | prostate | 8.90 |
| 88 | RPMI-2650 | SCC | 11.21 |
| 89 | SCC-15 | SCC | 14.55 |
| 90 | SCC-25 | SCC | 3.62 |
| 91 | SCC-4 | SCC | 10.09 |
| 92 | SCC-9 | SCC | 8.39 |
| 93 | HS804.SK | skin | 39.12 |
| 94 | A-431 | squamous | 17.30 |

Example 8

Method of Creating N- and C-Terminal Deletion Mutants Corresponding to the HGPRBMY18 Polypeptide As described elsewhere herein, the present invention encompasses the creation of N- and C-terminal deletion mutants, in addition to any combination of N- and C-terminal deletions thereof, corresponding to the HGPRBMY18 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutants of the present invention, exemplary methods are described below.

Briefly, using the isolated cDNA clone encoding the full-length HGPRBMY18 polypeptide sequence, appropriate primers of about 15–25 nucleotides derived from the desired 5' and 3' positions of SEQ ID NO:1 may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the T45 to G361 N-terminal deletion mutant, the following primers could be used to amplify a cDNA fragment corresponding to this deletion mutant:

```
5' Primer 5'-GCAGCA GCGGCCGC ACCGTGCTGGTGCTCATCTTTGCAG-3'  (SEQ ID NO:42)
                NotI 3' Primer 5'-GCAGCA GTCGAC GCCAGAAATAATCGACAAGTC-3'        (SEQ ID NO:43)
                SalI
```

For example, in the case of the M1 to N317 C-terminal deletion mutant, the following primers could be used to amplify a cDNA fragment corresponding to this deletion mutant:

```
5' Primer 5'-GCAGCA GCGGCCGC ATGTCCCCTGAATGCGCGCGGGCAG-3'  (SEQ ID NO:44)
               NotI 3' Primer 5'-GCAGCA GTCGAC GTTTAGGGCTGAATTAGCAAATGTG-3'   (SEQ ID NO:45)
              SalI
```

Representative PCR amplification conditions are provided below, although the skilled artisan would appreciate that other conditions may be required for efficient amplification. A 100 ul PCR reaction mixture may be prepared using 10 ng of the template DNA (cDNA clone of HGPRBMY18), 200 uM 4dNTPs, 1 uM primers, 0.25U Taq DNA polymerase (PE), and standard Taq DNA polymerase buffer. Typical PCR cycling condition are as follows:

| | |
|---|---|
| 20–25 cycles: | 45 sec, 93 degrees |
| | 2 min, 50 degrees |
| | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E. coli cells using methods provided herein and/or otherwise known in the art.

The 5' primer sequence for amplifying any additional N-terminal deletion mutants may be determined by reference to the following formula:

$(S+(X*3))$ to $((S+(X*3))+25)$, wherein 'S' is equal to the nucleotide position of the initiating start codon of the HGPRBMY18 gene (SEQ ID NO:1), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula:

$(S+(X*3))$ to $((S+(X*3))-25)$, wherein 'S' is equal to the nucleotide position of the initiating start codon of the HGPRBMY18 gene (SEQ ID NO:1), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

In preferred embodiments, the following N-terminal HGPRBMY18 deletion polypeptides are encompassed by the present invention: M1-G361, S2-G361, P3-G361, E4-G361, C5-G361, A6-G361, R7-G361, A8-G361, A9-G361, G10-G361, D11-G361, A12-G361, P13-G361, L14-G361, R15-G361, S16-G361, L17-G361, E18-G361, Q19-G361, A20-G361, N21-G361, R22-G361, T23-G361, R24-G361, F25-G361, P26-G361, F27-G361, F28-G361, S29-G361, D30-G361, V31-G361, K32-G361, G33-G361, D34-G361, H35-G361, R36-G361, L37-G361, V38-G361, L39-G361, A40-G361, A41-G361, V42-G361, E43-G361, T44-G361, T45-G361, V46-G361, L47-G361, V48-G361, L49-G361, I50-G361, F51-G361, A52-G361, V53-G361, S54-G361, L55-G361, L56-G361, G57-G361, N58-G361, V59-G361, C60-G361, A61-G361, L62-G361, V63-G361, L64-G361, V65-G361, A66-G361, R67-G361, R68-G361, R69-G361, R70-G361, R71-G361, G72-G361, A73-G361, T74-G361, A75-G361, C76-G361, L77-G361, V78-G361, L79-G361, N80-G361, L81-G361, F82-G361, C83-G361, A84-G361, D85-G361, L86-G361, L87-G361, F88-G361, I89-G361, S90-G361, A91-G361, I92-G361, P93-G361, L94-G361, V95-G361, L96-G361, A97-G361, V98-G361, R99-G361, W100-G361, T101-G361, E102-G361, A103-G361, W104-G361, L105-G361, L106-G361, G107-G361, P108-G361, V109-G361, A110-G361, C111-G361, H112-G361, L113-G361, L114-G361, F115-G361, Y116-G361, V117-G361, M118-G361, T119-G361, L120-G361, S121-G361, G122-G361, S123-G361, V124-G361, T125-G361, I126-G361, L127-G361, T128-G361, L129-G361, A130-G361, A131-G361, V132-G361, S133-G361, L134-G361, E135-G361, R136-G361, M137-G361, V138-G361, C139-G361, I140-G361, V141-G361, H142-G361, L143-G361, Q144-G361, R145-G361, G146-G361, V147-G361, R148-G361, G149-G361, P150-G361, G151-G361, R152-G361, R153-G361, A154-G361, R155-G361, A156-G361, V157-

G361, L158-G361, L159-G361, A160-G361, L161-G361, I162-G361, W163-G361, G164-G361, Y165-G361, S166-G361, A167-G361, V168-G361, A169-G361, A170-G361, L171-G361, P172-G361, L173-G361, C174-G361, V175-G361, F176-G361, F177-G361, R178-G361, V179-G361, V180-G361, P181-G361, Q182-G361, R183-G361, L184-G361, P185-G361, G186-G361, A187-G361, D188-G361, Q189-G361, E190-G361, I191-G361, S192-G361, I193-G361, C194-G361, T195-G361, L196-G361, I197-G361, W198-G361, P199-G361, T200-G361, I201-G361, P202-G361, G203-G361, E204-G361, I205-G361, S206-G361, W207-G361, D208-G361, V209-G361, S210-G361, F211-G361, V212-G361, T213-G361, L214-G361, N215-G361, F216-G361, L217-G361, V218-G361, P219-G361, G220-G361, L221-G361, V222-G361, I223-G361, V224-G361, I225-G361, S226-G361, Y227-G361, S228-G361, K229-G361, I230-G361, L231-G361, Q232-G361, I233-G361, T234-G361, K235-G361, A236-G361, S237-G361, R238-G361, K239-G361, R240-G361, L241-G361, T242-G361, V243-G361, S244-G361, L245-G361, A246-G361, Y247-G361, S248-G361, E249-G361, S250-G361, H251-G361, Q252-G361, I253-G361, R254-G361, V255-G361, S256-G361, Q257-G361, Q258-G361, D259-G361, F260-G361, R261-G361, L262-G361, F263-G361, R264-G361, T265-G361, L266-G361, F267-G361, L268-G361, L269-G361, M270-G361, V271-G361, S272-G361, F273-G361, F274-G361, I275-G361, M276-G361, W277G361, S278-G361, P279-G361, I280-G361, I281-G361, I282-G361, T283-G361, I284-G361, L285-G361, L286-G361, I287-G361, L288-G361, I289-G361, Q290-G361, N291-G361, F292-G361, K293-G361, Q294-G361, D295-G361, L296-G361, V297-G361, I298-G361, W299-G361, P300-G361, S301-G361, L302-G361, F303-G361, F304-G361, W305-G361, V306-G361, V307-G361, A308-G361, F309-G361, T310-G361, F311-G361, A312-G361, N313-G361, S314-G361, A315-G361, L316-G361, N317-G361, P318-G361, I319-G361, L320-G361, Y321-G361, N322-G361, M323-G361, T324-G361, L325-G361, C326-G361, R327-G361, N328-G361, E329-G361, W330-G361, K331-G361, K332-G361, I333-G361, F334-G361, C335-G361, C336-G361, F337-G361, W338-G361, F339-G361, P340-G361, E341-G361, K342-G36.1, G343-G361, A344-G361, I345-G361, L346-G361, T347-G361, D348-G361, T349-G361, S350-G361, V351-G361, K352-G361, R353-G361, N354-G361, and/or D355-G361 of SEQ ID NO:2. Polynucleotide sequences encoding these polypeptides are also provided. The present invention also encompasses the use of these N-terminal HGPRBMY18 deletion polypeptides as immunogenic and/or antigenic epitopes as described elsewhere herein.

In preferred embodiments, the following C-terminal HGPRBMY18 deletion polypeptides are encompassed by the present invention: M1-G361, M1-S360, M1-I359, M1-I358, M1-S357, M1-L356, M1-D355, M1-N354, M1-R353, M1-K352, M1-V351, M1-S350, M1-T349, M1-D348, M1-T347, M1-L346, M1-I345, M1-A344, M1-G343, M1-K342, M1-E341, M1-P340, M1-F339, M1-W338, M1-F337, M1-C336, M1-C335, M1-F334, M1-I333, M1-K332, M1-K331, M1-W330, M1-E329, M1-N328, M1-R327, M1-C326, M1-L325, M1-T324, M1-M323, M1-N322, M1-Y321, M1-L320, M1-I319, M1-P318, M1-N317, M1-L316, M1-A315, M1-S314, M1-N313, M1-A312, M1-F311, M1-T310, M1-F309, M1-A308, M1-V307, M1-V306, M1-W305, M1-F304, M1-F303, M1-L302, M1-S301, M1-P300, M1-W299, M1-I298, M1-V297, M1-L296, M1-D295, M1-Q294, M1-K293, M1-F292, M1-N291, M1-Q290, M1-I289, M1-L288, M1-I287, M1-L286, M1-L285, M1-I284, M1-T283, M1-I282, M1-I281, M1-I280, M1-P279, M1-S278, M1-W277, M1-M276, M1-I275, M1-F274, M1-F273, M1-S272, M1-V271, M1-M270, M1-L269, M1-L268, M1-F267, M1-L266, M1-T265, M1-R264, M1-F263, M1-L262, M1-R261, M1-F260, M1-D259, M1-Q258, M1-Q257, M1-S256, M1-V255, M1-R254, M1-I253, M1-Q252, M1-H251, M1-S250, M1-E249, M1-S248, M1-Y247, M1-A246, M1-L245, M1-S244, M1-V243, M1-T242, M1-L241, M1-R240, M1-K239, M1-R238, M1-S237, M1-A236, M1-K235, M1-T234, M1-I233, M1-Q232, M1-L231, M1-I230, M1-K229, M1-S228, M1-Y227, M1-S226, M1-I225, M1-V224, M1-I223, M1-V222, M1-L221, M1-G220, M1-P219, M1-V218, M1-L217, M1-F216, M1-N215, M1-L214, M1-T213, M1-V212, M1-F211, M1-S210, M1-V209, M1-D208, M1-W207, M1-S206, M1-I205, M1-E204, M1-G203, M1-P202, M1-I201, M1-T200, M1-P199, M1-W198, M1I-197, M1-L196, M1-T195, M1-C194, M1-I193, M1-S192, M1-I191, M1-E190, M1-Q189, M1-D188, M1-A187, M1-G186, M1-P185, M1-L184, M1-R183, M1-Q182, M1-P181, M1-V180, M1-V179, M1-R178, M1-F177, M1-F176, M1-V175, M1-C174, M1-L173, M1-P172, M1-L171, M1-A170, M1-A169, M1-V168, M1-A167, M1-S166, M1-Y165, M1-G164, M1-W163, M1-I162, M1-L161, M1-A160, M1-L159, M1-L158, M1-V157, M1-A156, M1-R155, M1-A154, M1-R153, M1-R152, M1-G151, M1-P150, M1-G149, M1-R148, M1-V147, M1-G146, M1-R145, M1-Q144, M1-L143, M1-H142, M1-V141, M1-I140, M1-C139, M1-V138, M1-M137, M1-R136, M1-E135, M1-L134, M1-S133, M1-V132, M1-A131, M1-A130, M1-L129, M1-T128, M1-L127, M1-I126, M1-T125, M1-V124, M1-S123, M1-G122, M1-S121, M1-L120, M1-T119, M1-M118, M1-V117, M1-Y116, M1-F115, M1-L114, M1-L113, M1-H112, M1-C111, M1-A111, M1-V109, M1-P108, M1-G107, M1-L106, M1-L105, M1-W104, M1-A103, M1-E102, M1-TO1, M1-W100, M1-R99, M1-V98, M1-A97, M1-L96, M1-V95, M1-L94, M1-P93, M1-I92, M1-A91, M1-S90, M1-I89, M1-F88, M1-L87, M1-L86, M1-D85, M1-A84, M1-C83, M1-F82, M1-L81, M1-N80, M1-L79, M1-V78, M1-L77, M1-C76, M1-A75, M1-T74, M1-A73, M1-G72, M1-R71, M1-R70, M1-R69, M1-R68, M1-R67, M1-A66, M1-V65, M1-L64, M1-V63, M1-L62, M1-A61, M1-C60, M1-V59, M1-N58, M1-G57, M1-L56, M1-L55, M1-S54, M1-V53, M1-A52, M1-F51, M1-I50, M1-L49, M1-V48, M1-L47, M1-V46, M1-T45, M1-T44, M1-E43, M1-V42, M1-A41, M1-A40, M1-L39, M1-V38, M1-L37, M1-R36, M1-H35, M1-D34, M1-G33, M1-K32, M1-V31, M1-D30, M1-S29, M1-F28, M1-F27, M1-P26, M1-F25, M1-R24, M1-T23, M1-R22, M1-N21, M1-A20, M1-Q19, M1-E18, M1-L17, M1-S16, M1-R15, M1-L14, M1-P13, M1-A12, M1-D11, M1-G10, M1-A9, M1-A8, and/or M1-R7 of SEQ ID NO:2. Polynucleotide sequences encoding these polypeptides are also provided. The present invention also encompasses the use of these C-terminal HGPRBMY18 deletion polypeptides as immunogenic and/or antigenic epitopes as described elsewhere herein.

Alternatively, preferred polypeptides of the present invention may comprise polypeptide sequences corresponding to, for example, internal regions of the HGPRBMY18 polypeptide (e.g., any combination of both N- and C-terminal HGPRBMY18 polypeptide deletions) of SEQ ID NO:2. For example, internal regions could be defined by the equation: amino acid NX to amino acid CX, wherein NX refers to any N-terminal deletion polypeptide amino acid of HGPRBMY18 (SEQ ID NO:2), and where CX refers to any C-terminal deletion polypeptide amino acid of HGPRBMY18 (SEQ ID NO:2). Polynucleotides encoding these polypeptides are also provided. The present invention also encompasses the use of these polypeptides as an immunogenic and/or antigenic epitope as described elsewhere herein.

Example 9

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, pharmaceutical, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered G-protein coupled receptor may be constitutively active upon binding of its cognate ligand. Alternatively, an engineered G-protein coupled receptor may be constitutively active in the absence of ligand binding. In yet another example, an engineered GPCR may be capable of being activated with less than all of the regulatory factors and/or conditions typically required for GPCR activation (e.g., ligand binding, phosphorylation, conformational changes, etc.). Such GPCRs would be useful in screens to identify GPCR modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145–152, (1986), and Hill, D E, et al, Methods Enzymol., 55:559–568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2–4 ug of the DNA substrate(s) would be digested with 0.0015 units of Dnase I (Sigma) per ul in 100 ul of 50 mM Tris-HCL, pH 7.4/1 mM MgCl2 for 10–20 min. at room temperature. The resulting fragments of 10–50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10–50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris•HCL, pH 9.0, and 0.1% Triton X-100, at a final fragment concentration of 10–30 ng/ul. No primers are added at this point. Taq DNA polymerase (Promega) would be used at 2.5 units per 100 ul of reaction mixture. A PCR program of 94 C for 60 s; 94 C for 30 s, 50–55 C for 30 s, and 72 C for 30 s using 30–45 cycles, followed by 72 C for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6): 1307–1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336–347, (1997), F. R., Cross, et al., Mol. Cell. Biol., 18:2923–2931, (1998), and A. Crameri., et al., Nat. Biotech., 15:436–438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436–438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 10

Signal Transduction Assays

The activity of GPCRs or homologues thereof, can be measured using any assay suitable for the measurement of the activity of a G protein-coupled receptor, as commonly known in the art. Signal transduction activity of a G protein-coupled receptor can be monitor by monitoring intracellular $Ca^{2+}$, cAMP, inosital 1,4,5-trisphophate ($IP_3$), or 1,2-diacylglycerol (DAG). Assays for the measurement of intracellular $Ca^{2+}$ are described in Sakurai et al. (EP 480 381). Intracellular $IP_3$ can be measured using a kit available from Amersham, Inc. (Arlington Heights, Ill.). A kit for measuring intracellular cAMP is available from Diagnostic Products, Inc. (Los Angeles, Calif.).

Activation of a G protein-coupled receptor triggers the release of $Ca^{2+}$ ions sequestered in the mitochondria, endoplasmic reticulum, and other cytoplasmic vesicles into the cytoplasm. Fluorescent dyes, e.g., fura-2, can be used to measure the concentration of free cytoplasmic $Ca^{2+}$. The ester of fura-2, which is lipophilic and can diffuse across the cell membrane, is added to the media of the host cells expressing GPCRs. Once inside the cell, the fura-2 ester is hydrolyzed by cytosolic esterases to its non-lipophilic form, and then the dye cannot diffuse back out of the cell. The non-lipophilic form of fura-2 will fluoresce when it binds to free $Ca^{2+}$. The fluorescence can be measured without lysing the cells at an excitation spectrum of 340 nm or 380 nm and at fluorescence spectrum of 500 nm (Sakurai et al., EP 480 381).

Upon activation of a G protein-coupled receptor, the rise of free cytosolic $Ca^{2+}$ concentrations is preceded by the hydrolysis of phosphatidylinositol 4,5-bisphosphate. Hydrolysis of this phospholipid by the phospholipase C yields 1,2-diacylglycerol (DAG), which remains in the membrane, and water-soluble inosital 1,4,5-trisphophate ($IP_3$). Binding of ligands or agonists will increase the concentration of DAG and $IP_3$. Thus, signal transduction activity can be measured by monitoring the concentration of these hydrolysis products.

To measure the $IP_3$ concentrations, radioactivity labeled $^3H$-inositol is added to the media of host cells expressing GPCRs. The $^3H$-inositol is taken up by the cells and incorporated into $IP_3$. The resulting inositol triphosphate is separated from the mono and di-phosphate forms and measured (Sakurai et al., EP 480 381). Alternatively, Amersham provides an inosital 1,4,5-triphosphate assay system. With this system Amersham provides tritylated inositol 1,4,5-triphosphate and a receptor capable of distinguishing the radioactive inositol from other inositol phosphates. With these reagents an effective and accurate competition assay can be performed to determine the inositol triphosphate levels.

Cyclic AMP levels can be measured according to the methods described in Gilman et al., Proc. Natl. Acad. Sci. 67:305–312 (1970). In addition, a kit for assaying levels of cAMP is available from Diagnostic Products Corp. (Los Angeles, Calif.).

Example 11

GPCR Activity

Another method for screening compounds which are antagonists, and thus inhibit activation of the receptor polypeptide of the present invention is provided. This involves determining inhibition of binding of labeled ligand, such as dATP, dAMP, or UTP, to cells which have the receptor on the surface thereof, or cell membranes containing the receptor. Such a method further involves transfecting a eukaryotic cell with DNA encoding the GPCR polypeptide such that the cell expresses the receptor on its surface. The cell is then contacted with a potential antagonist in the presence of a labeled form of a ligand, such as dATP, dAMP, or UTP. The ligand can be labeled, e.g., by radioactivity, fluorescence, or any detectable label commonly known in the art. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called a binding assay. Naturally, this same technique can be used to determine agonists.

In a further screening procedure, mammalian cells, for example, but not limited to, CHO, HEK 293, Xenopus Oocytes, RBL-2H3, etc., which are transfected, are used to express the receptor of interest. The cells are loaded with an indicator dye that produces a fluorescent signal when bound to calcium, and the cells are contacted with a test substance and a receptor agonist, such as DATP, DAMP, or UTP. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

In yet another screening procedure, mammalian cells are transfected to express the receptor of interest, and are also transfected with a reporter gene construct that is coupled to activation of the receptor (for example, but not limited to luciferase or beta-galactosidase behind an appropriate promoter). The cells are contacted with a test substance and the receptor agonist (ligand), such as dATP, dAMP, or UTP, and the signal produced by the reporter gene is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another screening technique for antagonists or agonists involves introducing RNA encoding the GPCR polypeptide into cells (or CHO, HEK 293, RBL-2H3, etc.) to transiently or stably express the receptor. The receptor cells are then contacted with the receptor ligand, such as dATP, dAMP, or UTP, and a compound to be screened. Inhibition or activation of the receptor is then determined by detection of a signal, such as, cAMP, calcium, proton, or other ions.

Example 12

Method of Screening, In Vitro, Compounds that Bind to the HGPRBMY18 Polypeptide

In vitro systems can be designed to identify compounds capable of binding the HGPRBMY18 polypeptide of the invention. Compounds identified can be useful, for example, in modulating the activity of wild type and/or mutant HGPRBMY18 polypeptide, preferably a mutant HGPRBMY18 polypeptide, can be useful in elaborating the biological function of the HGPRBMY18 polypeptide, can be utilized in screens for identifying compounds that disrupt normal HGPRBMY18 polypeptide interactions, or can in themselves disrupt such interactions.

The principle of the assays used to identify compounds that bind to the HGPRBMY18 polypeptide involves preparing a reaction mixture of the HGPRBMY18 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring HGPRBMY18 polypeptide or the test substance onto a solid phase and detecting HGPRBMY18 polypeptide/test compound complexes anchored on the solid phase at the end of the reaction. In one embodiment of such a method, the HGPRBMY18 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for HGPRBMY18 polypeptide or the test compound to anchor any complexes formed in solution, and a labeled antibody specific for the other component of the possible complex to detect anchored complexes.

Another example of a screening assay to identify compounds that bind to HGPRBMY18, relates to the application of a cell membrane-based scintillation proximity assay ("SPA"). Such an assay would require the idenification of a ligand for HGPRBMY18 polypeptide. Once identified, unlabeled ligand is added to assay-ready plates that would serve as a positive control. The SPA beads and membranes are added next, and then $^{125}$I-labeled ligand is added. After an equilibration period of 2–4 hours at room temperature, the plates can be counted in a scintillation counting machine, and the percent inhibition or stimulation calculated. Such an SPA assay may be based upon a manual, automated, or semi-automated platform, and encompass 96, 384, 1536-well plates or more. Any number of SPA beads may be used as applicable to each assay. Examples of SPA beads include, for example, Leadseeker WGA PS (Amersham cat # RPNQ 0260), and SPA Beads (PVT-PEI-WGA-TypeA; Amersham cat # RPNQ0003). The utilized membranes may also be derived from a number of cell line and tissue sources depending upon the expression profile of the respective polypeptide and the adaptability of such a cell line or tissue source to the development of a SPA-based assay. Examples of membrane preparations include, for example, cell lines transformed to express the receptor to be assayed in CHO cells or HEK cells, for example. SPA-based assays are well known in the art and are encompassed by the present invention. One such assay is described in U.S. Pat. No. 4,568,649, which is incorporated herein by reference. The skilled artisan would acknowledge that certain modifications of known SPA assays may be required to adapt such assays to each respective polypeptide.

One such screening procedure involves the use of melanophores which are transfected to express the HGPRBMY18 polypeptide of the present invention. Such a screening technique is described in PCT WO 92/01810, published Feb. 6, 1992. Such an assay may be employed to screen for a compound which inhibits activation of the receptor polypeptide of the present invention by contacting the melanophore cells which encode the receptor with both the receptor ligand, such as LPA, and a compound to be screened. Inhibition of the signal generated by the ligand indicates that a compound is a potential antagonist for the receptor, i.e., inhibits activation of the receptor.

The technique may also be employed for screening of compounds which activate the receptor by contacting such cells with compounds to be screened and determining whether such compound generates a signal, i.e., activates the receptor. Other screening techniques include the use of cells which express the HGPRBMY18 polypeptide (for example, transfected CHO cells) in a system which measures extracellular pH changes caused by receptor activation. In this technique, compounds may be contacted with cells expressing the receptor polypeptide of the present invention. A second messenger response, e.g., signal transduction or pH changes, is then measured to determine whether the potential compound activates or inhibits the receptor.

Another screening technique involves expressing the HGPRBMY18 polypeptide in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists or agonists by determining inhibition of binding of labeled ligand, such as LPA, to cells which have the receptor on the surface thereof, or cell membranes containing the receptor. Such a method involves transfecting a cell (such as eukaryotic cell) with DNA encoding the HGPRBMY18 polypeptide such that the cell expresses the receptor on its surface. The cell is then contacted with a potential antagonist or agonist in the presence of a labeled form of a ligand, such as LPA. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

Another screening procedure involves the use of mammalian cells (CHO, HEK 293, *Xenopus* Oocytes, RBL-2H3, etc) which are transfected to express the receptor of interest. The cells are loaded with an indicator dye that produces a fluorescent signal when bound to calcium, and the cells are contacted with a test substance and a receptor agonist, such as LPA. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

Another screening procedure involves use of mammalian cells (CHO, HEK293, *Xenopus* Oocytes, RBL-2H3, etc.) which are transfected to express the receptor of interest, and which are also transfected with a reporter gene construct that is coupled to activation of the receptor (for example, luciferase or beta-galactosidase behind an appropriate promoter). The cells are contacted with a test substance and the receptor agonist (ligand), such as LPA, and the signal produced by the reporter gene is measured after a defined period of time. The signal can be measured using a luminometer, spectrophotometer, fluorimeter, or other such instrument appropriate for the specific reporter construct used. Change of the signal generated by the ligand indicates that a compound is a potential antagonist or agonist for the receptor.

Another screening technique for antagonists or agonists involves introducing RNA encoding the HGPRBMY18 polypeptide into *Xenopus* oocytes (or CHO, HEK 293, RBL-2H3, etc.) to transiently or stably express the receptor. The receptor oocytes are then contacted with the receptor ligand, such as LPA, and a compound to be screened. Inhibition or activation of the receptor is then determined by detection of a signal, such as, cAMP, calcium, proton, or other ions.

Another method involves screening for HGPRBMY18 polypeptide inhibitors by determining inhibition or stimulation of HGPRBMY18 polypeptide-mediated cAMP and/or adenylate cyclase accumulation or diminution. Such a method involves transiently or stably transfecting a eukaryotic cell with HGPRBMY18 polypeptide receptor to express the receptor on the cell surface.

The cell is then exposed to potential antagonists or agonists in the presence of HGPRBMY18 polypeptide ligand, such as LPA. The changes in levels of cAMP is then measured over a defined period of time, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist or agonist binds the receptor, and thus inhibits HGPRBMY18 polypeptide-ligand binding, the levels of HGPRBMY18 polypeptide-mediated cAMP, or adenylate cyclase activity, will be reduced or increased.

One preferred screening method involves co-transfecting HEK-293 cells with a mammalian expression plasmid encoding a G-protein coupled receptor (GPCR), such as HGPRBMY18, along with a mixture comprised of mammalian expression plasmids cDNAs encoding GU15 (Wilkie T. M. et al Proc Natl Acad Sci USA 1991 88: 10049–10053), GU16 (Amatruda T. T. et al Proc Natl Acad Sci USA 1991 8: 5587–5591, and three chimeric G-proteins refered to as Gqi5, Gqs5, and Gqo5 (Conklin BR et al Nature 1993 363: 274–276, Conklin B. R. et al Mol Pharmacol 1996 50: 885–890). Following a 24 h incubation the trasfected HEK-293 cells are plated into poly-D-lysine coated 96 well black/clear plates (Becton Dickinson, Bedford, Mass.).

The cells are assayed on FLIPR (Fluorescent Imaging Plate Reader, Molecular Devices, Sunnyvale, Calif.) for a calcium mobilization response following addition of test ligands. Upon identification of a ligand which stimulates calcium mobilization in HEK-293 cells expressing a given GPCR and the G-protein mixtures, subsequent experiments are performed to determine which, if any, G-protein is required for the functional response. HEK-293 cells are then transfected with the test GPCR, or co-transfected with the test GPCR and G015, GD16, GqiS, Gqs5, or Gqo5. If the GPCR requires the presence of one of the G-proteins for functional expression in HEK-293 cells, all subsequent experiments are performed with HEK-293 cell cotransfected with the GPCR and the G-protein which gives the best response. Alternatively, the receptor can be expressed in a different cell line, for example RBL-2H3, without additional Gproteins.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATα. Each cell type secretes a small peptide hormone that binds to a G-protein coupled receptor on opposite mating type cells which triggers a MAP kinase cascade leading to G1 arrest as a prelude to cell fusion.

Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e.g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclindependent kinases leading to cell cycle arrest; and (iii) construction of reporter genes fused to the FUS 1 gene promoter (where FUS 1 encodes a membrane-anchored glycoprotein required for cell fusion). Downstream reporter genes can permit either a positive growth selection (e.g., histidine prototrophy using the FUS1-HIS3 reporter), or a colorimetric, fluorimetric or spectrophotometric readout, depending on the specific reporter construct used (e.g., b-galactosidase induction using a FUSl-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J., Nature 384: 14–16, 1996; Manfredi et al., Mol. Cell. Biol. 16: 4700–4709,1996). This provides a rapid direct growth selection (e.g., using the FUS 1-HIS3 reporter) for surrogate peptide agonists that activate characterized or orphan receptors. Alternatively, yeast cells that functionally express human (or mammalian) G-protein coupled receptors linked to a reporter gene readout (e.g., FUSI-LacZ) can be used as a platform for high-throughput screening of known ligands, fractions of biological extracts and libraries of chemical compounds for either natural or surrogate ligands.

Functional agonists of sufficient potency (whether natural or surrogate) can be used as screening tools in yeast cell-based assays for identifying G-protein coupled receptor antagonists. For example, agonists will promote growth of a cell with FUS-HIS3 reporter or give positive readout for a cell with FUSI-LacZ. However, a candidate compound which inhibits growth or negates the positive readout induced by an agonist is an antagonist. For this purpose, the yeast system offers advantages over mammalian expression systems due to its ease of utility and null receptor background (lack of endogenous G-protein coupled receptors) which often interferes with the ability to identify agonists or antagonists.

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

SEQUENCE LISTING

<160> NUMBER OF SEQ ID NOS: 50

<210> SEQ ID NO 1
<211> LENGTH: 1086
<212> TYPE: DNA
<213> ORGANISM: Homo sapiens

<400> SEQUENCE: 1

```
atgtcccctg aatgcgcgcg ggcagcgggc gacgcgccct tgcgcagcct ggagcaagcc      60
aaccgcaccc gctttcccct cttctccgac gtcaagggcg accaccggct ggtgctggcc     120
gcggtggaga caaccgtgct ggtgctcatc tttgcagtgt cgctgctggg caacgtgtgc     180
gccctggtgc tggtggcgcg ccgacgacgc cgcggcgcga ctgcctgcct ggtactcaac     240
ctcttctgcg cggacctgct cttcatcagc gctatccctc tggtgctggc cgtgcgctgg     300
actgaggcct ggctgctggg ccccgttgcc tgccacctgc tcttctacgt gatgaccctg     360
agcggcagcg tcaccatcct cacgctggcc gcggtcagcc tggagcgcat ggtgtgcatc     420
gtgcacctgc agcgcggcgt gcggggtcct gggcggcggg cgcgggcagt gctgctggcg     480
ctcatctggg gctattcggc ggtcgccgct ctgcctctct gcgtcttctt ccgagtcgtc     540
ccgcaacggc tccccggcgc cgaccaggaa atttcgattt gcacactgat ttggcccacc     600
attcctggag agatctcgtg ggatgtctct tttgttactt tgaacttctt ggtgccagga     660
ctggtcattg tgatcagtta ctccaaaatt ttacagatca caaaggcatc aaggaagagg     720
ctcacggtaa gcctggccta ctcggagagc caccagatcc gcgtgtccca gcaggacttc     780
cggctcttcc gcaccctctt cctcctcatg gtctccttct tcatcatgtg gagccccatc     840
```

```
atcatcacca tcctcctcat cctgatccag aacttcaagc aagacctggt catctggccg    900
tccctcttct tctgggtggt ggccttcaca tttgctaatt cagccctaaa ccccatcctc    960
tacaacatga cactgtgcag gaatgagtgg aagaaaattt tttgctgctt ctggttccca   1020
gaaaagggag ccatttttaac agacacatct gtcaaaagaa atgacttgtc gattatttct   1080
ggctaa                                                                1086

<210> SEQ ID NO 2
<211> LENGTH: 360
<212> TYPE: PRT
<213> ORGANISM: Homo sapiens

<400> SEQUENCE: 2

Met Ser Pro Glu Cys Ala Arg Ala Ala Gly Asp Ala Pro Leu Arg Ser
1               5                   10                  15

Leu Glu Gln Ala Asn Arg Thr Arg Phe Pro Phe Phe Ser Asp Val Lys
            20                  25                  30

Gly Asp His Arg Leu Val Leu Ala Ala Val Glu Thr Thr Val Leu Val
        35                  40                  45

Leu Ile Phe Ala Val Ser Leu Leu Gly Asn Val Cys Ala Leu Val Leu
    50                  55                  60

Val Ala Arg Arg Arg Arg Gly Ala Thr Ala Cys Leu Val Leu Asn
65                  70                  75                  80

Leu Phe Cys Ala Asp Leu Leu Phe Ile Ser Ala Ile Pro Leu Val Leu
                85                  90                  95

Ala Val Arg Trp Thr Glu Ala Trp Leu Leu Gly Pro Val Ala Cys His
            100                 105                 110

Leu Leu Phe Tyr Val Met Thr Leu Ser Gly Val Thr Ile Leu Thr Leu
        115                 120                 125

Ala Ala Val Ser Leu Glu Arg Met Val Cys Ile Val His Leu Gln Arg
    130                 135                 140

Gly Val Arg Gly Pro Gly Arg Arg Ala Arg Ala Val Leu Leu Ala Leu
145                 150                 155                 160

Ile Trp Gly Tyr Ser Ala Val Ala Ala Leu Pro Leu Cys Val Phe Phe
                165                 170                 175

Arg Val Val Pro Gln Arg Leu Pro Gly Ala Asp Gln Glu Ile Ser Ile
            180                 185                 190

Cys Thr Leu Ile Trp Pro Thr Ile Pro Gly Glu Ile Ser Trp Asp Val
        195                 200                 205

Ser Phe Val Thr Leu Asn Phe Leu Val Pro Gly Leu Val Ile Val Ile
    210                 215                 220

Ser Tyr Ser Lys Ile Leu Gln Ile Thr Lys Ala Ser Arg Lys Arg Leu
225                 230                 235                 240

Thr Val Ser Leu Ala Tyr Ser Glu Ser His Gln Ile Arg Val Ser Gln
                245                 250                 255

Gln Asp Phe Arg Leu Phe Arg Thr Leu Phe Leu Met Val Ser Phe
            260                 265                 270

Phe Ile Met Trp Ser Pro Ile Ile Ile Thr Ile Leu Leu Ile Leu Ile
        275                 280                 285

Gln Asn Phe Lys Gln Asp Leu Val Ile Trp Pro Ser Leu Phe Phe Trp
    290                 295                 300

Val Val Ala Phe Thr Phe Ala Asn Ser Ala Leu Asn Pro Ile Leu Tyr
305                 310                 315                 320

Asn Met Thr Leu Cys Arg Asn Glu Trp Lys Lys Ile Phe Cys Cys Phe
```

```
              325                 330                 335
        Trp Phe Pro Glu Lys Gly Ala Ile Leu Thr Asp Thr Ser Val Lys Arg
                340                 345                 350

Asn Asp Leu Ser Ile Ile Ser Gly
                355                 360

<210> SEQ ID NO 3
<211> LENGTH: 1438
<212> TYPE: DNA
<213> ORGANISM: Homo sapiens

<400> SEQUENCE: 3
ccacgcgtcc gcggacgcgt gggaagtagc tgggattaca ggtacctgcc accatgccca    60
gctaattttt gtattttag tagagacggg gtttcaccac gttggccatg ctggtctgg    120 agctcccgac ctcaagtgat ccaccgcct tggcctccca agtgctgag attacaagca    180 tgagccactg tgcccagtca gtgcttagat ttcttaagac ccaaccttaa gaaagacaat    240
tagaagacag agtgggcaac tgggagaggc ctggtaatat ggcagaggga agagggggtg    300
aaggtgtggg tggcaggagg gtggctggtt ggggaagtgg ccactggatc ttaggccaca    360
ggcatacttt tccatctcca gcttcctcat ttacagaaaa cgagactgca gtggtgtgat    420
ggaaatgtgt gggacgggga caggtgactg gctttcatta ctaaccagag gacagcttag    480
acaagtcact ctggctgggc tcagtttcc ttatctctaa cgggactgga ttgcccagtg    540
ctcctcaaac tgtggcacct ggggcacatt catagcttgt gtgtgaatct gccagccttg    600
aaatatctgt cttccttgga tgcaagttt attaaaaatt ttggaaggac tcactctttt    660
tataagaaag catttatgtc attgttcaga atgcaaaatg tatatgcatt ttagttacaa    720
taactaatat ttgataacat ttaacgagta attactgtgt gccaagtgtg caaaactcta    780
ggtgagcctc acaataaccct aatggggtat tattattccc atttataga ttaaaaatct    840 ggggtagagg gagtagataa tccacctaaa gacctgttat taagtagtga taaaagatct    900
ccactccctc tctcccccac aaaatatgga ctcattacaa gttgttttag gatctacctc    960
cagacccatg gagtttcttt agtaaagcct gaacgacaca ggccaaaata atctccaaag    1020
gccagctctg accctttaa atcaattta gctaaatccg ttcacaaaag gcttcgcaca    1080
tccagtgtcc ctgaaaaata aaggaggttg ggcaggccct gcggggctc gaggaattcg    1140 ctaagtgagt tttctggctt ctggatacac tttcaaaggg ccagagggca cgaggcttcc    1200
gccttggccg ccacctcccc ggccagctgc ggtgttcgcg ccagtgttg ccgggcactt    1260 cctggttccc gcgcgccccg ggtgcagctc cctgcaccca gtgctggcgc tcctcagaag    1320
ggagggggcc agaggcgaga tgtcgcaacc gcctccctcc ctctttcccc gccttggcac    1380
tcagtcgcct cccagatgag cactctctca gaccgctgcg ggccgccagg cgccggga    1438

<210> SEQ ID NO 4
<211> LENGTH: 632
<212> TYPE: DNA
<213> ORGANISM: Homo sapiens

<400> SEQUENCE: 4
ttttctttta tagccgagtt tctcacacct ggcgagctgt ggcatgcttt taaacagagt    60
tcatttccag taccctccat cagtgcaccc tgctttaaga aaatgaacct atgcaaatag    120
acatccacag cgtcggtaaa ttaaggggtg atcaccaagt tcataatat tttccctta    180 taaaaggatt tgttggccag gtgcagtggt tcatgcctgt aatcccagca gtttgggagg    240
```

```
ctgaggtggg tggatcacct gaggtcagga gttcgagacc aacctgacca acatggtgag    300
acccccgtct ctactaaaaa taaaaaaaaa aattagctgg gagtggtggt gggcacctgt    360
aatcctagct acttgggagg ctgaaccagg agaatctctt gaacctggga ggcagaggtt    420
gcagtgagcc gagatcgtgc cattgcactc caaccagggc aacaagagtg aaactccatc    480
ttaaaaaaaa aaaaaaaaag atttgttatg ggttcctttt aaatgtgaac tttttttagtg   540 tgtttgtaat atgatcaaat ttaataaata tttatttatg actgttaaaa aaaaaaaaa    600 aaaaaaaaaa aaaaaaaaaa aaaaaaaaaa aa                                 632

<210> SEQ ID NO 5
<211> LENGTH: 80
<212> TYPE: DNA
<213> ORGANISM: Homo sapiens

<400> SEQUENCE: 5
agcaggtggt cgcccttgac gtcggagaag aagggaaagc gggtgcggtt ggcttgctcc    60
aaggtgaaga agggcgcgta                                                80

<210> SEQ ID NO 6
<211> LENGTH: 21
<212> TYPE: DNA
<213> ORGANISM: Homo sapiens

<400> SEQUENCE: 6
gactgcctgc ctggtactca a                                              21

<210> SEQ ID NO 7
<211> LENGTH: 18
<212> TYPE: DNA
<213> ORGANISM: Homo sapiens

<400> SEQUENCE: 7
gccaagcgtg aggatggt                                                  18

<210> SEQ ID NO 8
<211> LENGTH: 363
<212> TYPE: PRT
<213> ORGANISM: Ovis aries

<400> SEQUENCE: 8

Met Ala Gly Arg Leu Trp Gly Pro Gly Thr Pro Lys Gly Asn Gly
1               5                   10                  15

Ser Ala Leu Leu Asn Val Ser Gln Ala Ala Pro Gly Ala Gly Asp Gly
                20                  25                  30

Val Arg Pro Arg Pro Ser Trp Leu Ala Ala Thr Leu Ala Ser Ile Leu
            35                  40                  45

Ile Phe Thr Ile Val Val Asp Ile Val Gly Asn Leu Leu Val Val Leu
        50                  55                  60

Ser Val Tyr Arg Asn Lys Lys Leu Arg Asn Ala Gly Asn Val Phe Val
65                  70                  75                  80

Val Ser Leu Ala Val Ala Asp Leu Leu Val Ala Val Tyr Pro Tyr Pro
                85                  90                  95

Leu Ala Leu Ala Ser Ile Val Asn Asn Gly Trp Ser Leu Ser Ser Leu
                100                 105                 110

His Cys Gln Leu Ser Gly Phe Leu Met Gly Leu Ser Val Ile Gly Val
            115                 120                 125
```

-continued

```
Phe Ser Ile Thr Gly Ile Ala Ile Asn Arg Tyr Cys Cys Ile Cys His
    130                 135                 140

Ser Leu Arg Tyr Gly Lys Leu Tyr Ser Gly Thr Asn Ser Leu Cys Tyr
145                 150                 155                 160

Val Phe Leu Ile Trp Thr Leu Thr Leu Val Ala Ile Val Pro Asn Leu
                165                 170                 175

Cys Val Gly Thr Leu Gln Tyr Asp Pro Arg Ile Tyr Ser Cys Thr Phe
                180                 185                 190

Thr Gln Ser Val Ser Ser Ala Tyr Thr Ile Ala Val Val Phe His
    195                 200                 205

Phe Ile Val Pro Met Leu Val Val Phe Cys Tyr Leu Arg Ile Trp
    210                 215                 220

Ala Leu Val Leu Gln Val Arg Trp Lys Val Lys Pro Asp Asn Lys Pro
225                 230                 235                 240

Lys Leu Lys Pro Gln Asp Phe Arg Asn Phe Val Thr Met Phe Val Val
                245                 250                 255

Phe Val Leu Phe Ala Ile Cys Trp Ala Pro Leu Asn Phe Ile Gly Leu
                260                 265                 270

Val Val Ala Ser Asp Pro Ala Ser Met Ala Pro Arg Ile Pro Glu Trp
                275                 280                 285

Leu Phe Val Ala Ser Tyr Tyr Met Ala Tyr Phe Asn Ser Cys Leu Asn
    290                 295                 300

Ala Ile Ile Tyr Gly Leu Leu Asn Gln Asn Phe Arg Gln Glu Tyr Arg
305                 310                 315                 320

Lys Ile Ile Val Ser Leu Cys Thr Thr Lys Met Phe Phe Val Asp Ser
                325                 330                 335

Ser Asn His Val Ala Asp Arg Ile Lys Arg Lys Pro Ser Pro Leu Ile
                340                 345                 350

Ala Asn His Asn Leu Ile Lys Val Asp Ser Val
    355                 360
```

<210> SEQ ID NO 9
<211> LENGTH: 363
<212> TYPE: PRT
<213> ORGANISM: Ovis aries

<400> SEQUENCE: 9

```
Met Ala Gly Arg Leu Trp Gly Pro Gly Gly Thr Pro Lys Gly Asn Gly
1               5                   10                  15

Ser Ala Leu Leu Asn Val Ser Gln Ala Ala Pro Gly Ala Gly Asp Gly
                20                  25                  30

Val Arg Pro Arg Pro Ser Trp Leu Ala Ala Thr Leu Ala Ser Ile Leu
            35                  40                  45

Ile Phe Thr Ile Val Val Asp Ile Val Gly Asn Leu Leu Val Val Leu
    50                  55                  60

Ser Val Tyr Arg Asn Lys Lys Leu Arg Asn Ala Gly Asn Val Phe Val
65                  70                  75                  80

Val Ser Leu Ala Val Ala Asp Leu Leu Val Ala Val Tyr Pro Tyr Pro
                85                  90                  95

Leu Ala Leu Ala Ser Ile Val Asn Asn Gly Trp Ser Leu Ser Ser Leu
                100                 105                 110

His Cys Gln Leu Ser Gly Phe Leu Met Gly Leu Ser Val Ile Gly Val
        115                 120                 125

Phe Ser Ile Thr Gly Ile Ala Ile Asn Arg Tyr Cys Cys Ile Cys His
    130                 135                 140
```

```
Ser Leu Arg Tyr Gly Lys Leu Tyr Ser Gly Thr Asn Ser Leu Cys Tyr
145                 150                 155                 160

Val Phe Leu Ile Trp Thr Leu Thr Leu Val Ala Ile Val Pro Asn Leu
                165                 170                 175

Cys Val Gly Thr Leu Gln Tyr Asp Pro Arg Ile Tyr Ser Cys Thr Phe
            180                 185                 190

Thr Gln Ser Val Ser Ser Ala Tyr Thr Ile Ala Val Val Phe His
        195                 200                 205

Phe Ile Val Pro Met Leu Val Val Phe Cys Tyr Leu Arg Ile Trp
    210                 215                 220

Ala Leu Val Leu Gln Val Arg Trp Lys Val Lys Pro Asp Asn Lys Pro
225                 230                 235                 240

Lys Leu Lys Pro Gln Asp Phe Arg Asn Phe Val Thr Met Phe Val Val
                245                 250                 255

Phe Val Leu Phe Ala Ile Cys Trp Ala Pro Leu Asn Phe Ile Gly Leu
            260                 265                 270

Val Val Ala Ser Asp Pro Asp Ser Met Ala Pro Arg Ile Pro Glu Trp
        275                 280                 285

Leu Phe Val Ala Ser Tyr Tyr Met Ala Tyr Phe Asn Ser Cys Leu Asn
    290                 295                 300

Ala Ile Ile Tyr Gly Leu Leu Asn Gln Asn Phe Arg Gln Glu Tyr Arg
305                 310                 315                 320

Lys Ile Ile Val Ser Leu Cys Thr Thr Lys Met Phe Phe Val Asp Ser
                325                 330                 335

Ser Asn His Val Ala Asp Arg Ile Lys Arg Lys Pro Ser Pro Leu Ile
            340                 345                 350

Ala Asn Arg Asn Leu Val Lys Val Asp Ser Val
            355                 360

<210> SEQ ID NO 10
<211> LENGTH: 347
<212> TYPE: PRT
<213> ORGANISM: Mus musculus

<400> SEQUENCE: 10

Met Glu Leu Ala Met Val Asn Leu Ser Glu Gly Asn Gly Asp Pro Glu
1               5                   10                  15

Pro Pro Ala Pro Glu Ser Arg Pro Leu Phe Gly Ile Gly Val Glu Asn
                20                  25                  30

Phe Ile Thr Leu Val Val Phe Gly Leu Ile Phe Ala Met Gly Val Leu
            35                  40                  45

Gly Asn Ser Leu Val Ile Thr Val Leu Ala Arg Ser Lys Pro Gly Lys
50                  55                  60

Pro Arg Ser Thr Thr Asn Leu Phe Ile Leu Asn Leu Ser Ile Ala Asp
65                  70                  75                  80

Leu Ala Tyr Leu Leu Phe Cys Ile Pro Phe Gln Ala Thr Val Tyr Ala
                85                  90                  95

Leu Pro Thr Trp Val Leu Gly Ala Phe Ile Cys Lys Phe Ile His Tyr
            100                 105                 110

Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
    130                 135                 140

Leu Arg Val Ser Arg Asn Ala Leu Leu Gly Val Gly Phe Ile Trp Ala
```

-continued

```
        145                 150                 155                 160
Leu Ser Ile Ala Met Ala Ser Pro Val Ala Tyr His Gln Arg Leu Phe
                165                 170                 175
His Arg Asp Ser Asn Gln Thr Phe Cys Trp Glu Gln Trp Pro Asn Lys
            180                 185                 190
Leu His Lys Lys Ala Tyr Val Val Cys Thr Phe Val Phe Gly Tyr Leu
            195                 200                 205
Leu Pro Leu Leu Ile Cys Phe Cys Tyr Ala Lys Val Leu Asn His
            210                 215                 220
Leu His Lys Lys Leu Lys Asn Met Ser Lys Ser Glu Ala Ser Lys
225                 230                 235                 240
Lys Lys Thr Ala Gln Thr Val Leu Val Val Val Val Phe Gly Ile
                245                 250                 255
Ser Trp Leu Pro His His Val Val His Leu Trp Ala Glu Phe Gly Ala
                260                 265                 270
Phe Pro Leu Thr Pro Ala Ser Phe Phe Arg Ile Thr Ala His Cys
                275                 280                 285
Leu Ala Tyr Ser Asn Ser Ser Val Asn Pro Ile Ile Tyr Ala Phe Leu
            290                 295                 300
Ser Glu Asn Phe Arg Lys Ala Tyr Lys Gln Val Phe Lys Cys His Val
305                 310                 315                 320
Cys Asp Glu Ser Pro Arg Ser Glu Thr Lys Glu Asn Lys Ser Arg Met
                325                 330                 335
Asp Thr Pro Pro Ser Thr Asn Cys Thr His Val
                340                 345

<210> SEQ ID NO 11
<211> LENGTH: 345
<212> TYPE: PRT
<213> ORGANISM: Rattus norvegicus

<400> SEQUENCE: 11

Met Glu Leu Ala Pro Val Asn Leu Ser Glu Gly Asn Gly Asp Pro Glu
1               5                   10                  15
Pro Pro Ala Glu Pro Arg Pro Leu Phe Gly Ile Gly Val Glu Asn Phe
            20                  25                  30
Ile Thr Leu Val Val Phe Gly Leu Ile Phe Ala Met Gly Val Leu Gly
        35                  40                  45
Asn Ser Leu Val Ile Thr Val Leu Ala Arg Ser Lys Pro Gly Lys Pro
50                  55                  60
Arg Ser Thr Thr Asn Leu Phe Ile Leu Asn Leu Ser Ile Ala Asp Leu
65                  70                  75                  80
Ala Tyr Leu Leu Phe Cys Ile Pro Phe Gln Ala Thr Val Tyr Ala Leu
                85                  90                  95
Pro Thr Trp Val Leu Gly Ala Phe Ile Cys Lys Phe Ile His Tyr Phe
            100                 105                 110
Phe Thr Val Ser Met Leu Val Ser Ile Phe Thr Leu Ala Ala Met Ser
            115                 120                 125
Val Asp Arg Tyr Val Ala Ile Val His Ser Arg Arg Ser Ser Ser Leu
        130                 135                 140
Arg Val Ser Arg Asn Ala Leu Leu Gly Val Gly Phe Ile Trp Ala Leu
145                 150                 155                 160
Ser Ile Ala Met Ala Ser Pro Val Ala Tyr Tyr Gln Arg Leu Phe His
                165                 170                 175
```

-continued

```
Arg Asp Ser Asn Gln Thr Phe Cys Trp Glu His Trp Pro Asn Gln Leu
            180                 185                 190

His Lys Lys Ala Tyr Val Val Cys Thr Phe Val Phe Gly Tyr Leu Leu
        195                 200                 205

Pro Leu Leu Leu Ile Cys Phe Cys Tyr Ala Lys Val Leu Asn His Leu
    210                 215                 220

His Lys Lys Leu Lys Asn Met Ser Lys Ser Glu Ala Ser Lys Lys
225                 230                 235                 240

Lys Thr Ala Gln Thr Val Leu Val Val Val Phe Gly Ile Ser
                245                 250                 255

Trp Leu Pro His His Val Ile His Leu Trp Ala Glu Phe Gly Ala Phe
            260                 265                 270

Pro Leu Thr Pro Ala Ser Phe Phe Arg Ile Thr Ala His Cys Leu
        275                 280                 285

Ala Tyr Ser Asn Ser Ser Val Asn Pro Ile Ile Tyr Ala Phe Leu Ser
    290                 295                 300

Glu Asn Phe Arg Lys Ala Tyr Lys Gln Val Phe Lys Cys Arg Val Cys
305                 310                 315                 320

Asn Glu Ser Pro His Gly Asp Ala Lys Glu Lys Asn Arg Ile Asp Thr
                325                 330                 335

Pro Pro Ser Thr Asn Cys Thr His Val
            340                 345
```

<210> SEQ ID NO 12
<211> LENGTH: 349
<212> TYPE: PRT
<213> ORGANISM: Homo sapiens

<400> SEQUENCE: 12

```
Met Glu Leu Ala Val Gly Asn Leu Ser Glu Gly Asn Ala Ser Cys Pro
1               5                   10                  15

Glu Pro Pro Ala Pro Glu Pro Gly Pro Leu Phe Gly Ile Gly Val Glu
            20                  25                  30

Asn Phe Val Thr Leu Val Val Phe Gly Leu Ile Phe Ala Leu Gly Val
        35                  40                  45

Leu Gly Asn Ser Leu Val Ile Thr Val Leu Ala Arg Ser Lys Pro Gly
    50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
        115                 120                 125

Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Cys Ile Trp
145                 150                 155                 160

Ala Leu Ser Ile Ala Met Ala Ser Pro Val Ala Tyr His Gln Gly Leu
                165                 170                 175

Phe His Pro Arg Ala Ser Asn Gln Thr Phe Cys Trp Glu Gln Trp Pro
            180                 185                 190

Asp Pro Arg His Lys Lys Ala Tyr Val Val Cys Thr Phe Val Phe Gly
        195                 200                 205
```

```
Tyr Leu Leu Pro Leu Leu Ile Cys Phe Cys Tyr Ala Lys Val Leu
    210                 215                 220

Asn His Leu His Lys Leu Lys Asn Met Ser Lys Lys Ser Glu Ala
225                 230                 235                 240

Ser Lys Lys Lys Thr Ala Gln Thr Val Leu Val Val Val Val Phe
                245                 250                 255

Gly Ile Ser Trp Leu Pro His Ile Ile His Leu Trp Ala Glu Phe
                260                 265                 270

Gly Val Phe Pro Leu Thr Pro Ala Ser Phe Leu Phe Arg Ile Thr Ala
                275                 280                 285

His Cys Leu Ala Tyr Ser Asn Ser Ser Val Asn Pro Ile Ile Tyr Ala
                290                 295                 300

Phe Leu Ser Glu Asn Phe Arg Lys Ala Tyr Lys Gln Val Phe Lys Cys
305                 310                 315                 320

His Ile Arg Lys Asp Ser His Leu Ser Asp Thr Lys Glu Asn Lys Ser
                325                 330                 335

Arg Ile Asp Thr Pro Pro Ser Thr Asn Cys Thr His Val
                340                 345

<210> SEQ ID NO 13
<211> LENGTH: 359
<212> TYPE: PRT
<213> ORGANISM: Mus musculus

<400> SEQUENCE: 13

Met Glu Pro Leu Ser Leu Ala Ser Thr Pro Ser Trp Asn Ala Ser Ala
1               5                   10                  15

Ala Ser Ser Gly His Asn Trp Ser Leu Val Asp Pro Val Ser Pro Met
                20                  25                  30

Gly Ala Arg Ala Val Leu Val Pro Val Leu Tyr Leu Leu Val Cys Thr
                35                  40                  45

Val Gly Leu Gly Gly Asn Thr Leu Val Ile Tyr Val Val Leu Arg Tyr
    50                  55                  60

Ala Lys Met Lys Thr Val Thr Asn Val Tyr Ile Leu Asn Leu Ala Val
65                  70                  75                  80

Ala Asp Val Leu Phe Met Leu Gly Leu Pro Phe Leu Ala Thr Gln Asn
                85                  90                  95

Ala Val Ser Tyr Trp Pro Phe Gly Phe Leu Cys Arg Leu Val Met Thr
                100                 105                 110

Leu Asp Gly Ile Asn Gln Phe Thr Ser Ile Phe Cys Leu Met Val Met
                115                 120                 125

Ser Val Asp Arg Tyr Leu Ala Val Val His Pro Leu Arg Ser Ala Arg
    130                 135                 140

Trp Arg Arg Pro Arg Val Ala Lys Leu Ala Ser Ala Ala Val Trp Val
145                 150                 155                 160

Phe Ser Leu Leu Met Ser Leu Pro Leu Leu Val Phe Ala Asp Val Gln
                165                 170                 175

Glu Gly Trp Gly Thr Cys Asn Leu Ser Trp Pro Glu Pro Val Gly Leu
                180                 185                 190

Trp Gly Ala Ala Phe Ile Thr Tyr Thr Ser Val Leu Gly Phe Phe Gly
                195                 200                 205

Pro Leu Leu Val Ile Cys Leu Cys Tyr Leu Leu Ile Val Val Lys Val
    210                 215                 220

Lys Ala Ala Gly Met Arg Val Gly Ser Arg Arg Arg Arg Ser Glu Arg
```

```
            225                 230                 235                 240
Lys Val Thr Arg Met Val Val Val Leu Val Phe Val Gly Cys
                245                 250                 255

Trp Leu Pro Phe Phe Ile Val Asn Ile Val Asn Leu Ala Phe Thr Leu
                260                 265                 270

Pro Glu Pro Thr Ser Ala Gly Leu Tyr Phe Val Val Leu
                275                 280                 285

Ser Tyr Ala Asn Ser Cys Ala Asn Pro Leu Leu Tyr Gly Phe Leu Ser
            290                 295                 300

Asp Asn Phe Arg Gln Ser Phe Arg Lys Ala Leu Cys Leu Arg Arg Gly
305                 310                 315                 320

Tyr Gly Val Glu Asp Ala Asp Ala Ile Glu Pro Arg Pro Asp Lys Ser
                325                 330                 335

Gly Arg Pro Gln Thr Thr Leu Pro Thr Arg Ser Cys Glu Ala Asn Gly
                340                 345                 350

Leu Met Gln Thr Ser Arg Leu
                355

<210> SEQ ID NO 14
<211> LENGTH: 360
<212> TYPE: PRT
<213> ORGANISM: Rattus norvegicus

<400> SEQUENCE: 14

Met Glu Pro Leu Ser Leu Ala Ser Thr Pro Ser Trp Asn Ala Ser Ala
1               5                   10                  15

Ala Ser Ser Gly Asn His Asn Trp Ser Leu Val Gly Ala Ser Pro Met
                20                  25                  30

Gly Ala Arg Ala Val Leu Val Pro Val Leu Tyr Leu Leu Val Cys Thr
            35                  40                  45

Val Gly Leu Ser Gly Asn Thr Leu Val Ile Tyr Val Val Leu Arg His
    50                  55                  60

Ala Lys Met Lys Thr Val Thr Asn Val Tyr Ile Leu Asn Leu Ala Val
65                  70                  75                  80

Ala Asp Val Leu Phe Met Leu Gly Leu Pro Phe Leu Ala Thr Gln Asn
                85                  90                  95

Ala Val Val Ser Tyr Trp Pro Phe Gly Phe Leu Cys Arg Leu Val Met
            100                 105                 110

Thr Leu Asp Gly Ile Asn Gln Phe Thr Ser Ile Phe Cys Leu Met Val
            115                 120                 125

Met Ser Val Asp Arg Tyr Leu Ala Val Val His Pro Leu Arg Ser Ala
130                 135                 140

Arg Trp Arg Arg Pro Arg Val Ala Lys Met Ala Ser Ala Ala Val Trp
145                 150                 155                 160

Val Phe Ser Leu Leu Met Ser Leu Pro Leu Leu Val Phe Ala Asp Val
                165                 170                 175

Gln Glu Gly Trp Gly Thr Cys Asn Leu Ser Trp Pro Glu Pro Val Gly
            180                 185                 190

Leu Trp Gly Ala Ala Phe Ile Thr Tyr Thr Ser Val Leu Gly Phe Phe
        195                 200                 205

Gly Pro Leu Leu Val Ile Cys Leu Cys Tyr Leu Leu Ile Val Val Lys
        210                 215                 220

Val Lys Ala Ala Gly Met Arg Val Gly Ser Arg Arg Arg Ser Glu
225                 230                 235                 240
```

-continued

```
Pro Lys Val Thr Arg Met Val Val Val Leu Val Phe Val Gly
            245                 250                 255

Cys Trp Leu Pro Phe Phe Ile Val Asn Ile Val Asn Leu Ala Phe Thr
                260                 265                 270

Leu Pro Glu Glu Pro Thr Ser Ala Gly Leu Tyr Phe Phe Val Val Val
            275                 280                 285

Leu Ser Tyr Ala Asn Ser Cys Ala Asn Pro Leu Leu Tyr Gly Phe Leu
            290                 295                 300

Ser Asp Asn Phe Arg Gln Ser Phe Arg Lys Val Leu Cys Leu Arg Arg
305                 310                 315                 320

Gly Tyr Gly Met Glu Asp Ala Asp Ala Ile Glu Pro Arg Pro Asp Lys
                325                 330                 335

Ser Gly Arg Pro Gln Ala Thr Leu Pro Thr Arg Ser Cys Glu Ala Asn
            340                 345                 350

Gly Leu Met Gln Thr Ser Arg Ile
            355                 360

<210> SEQ ID NO 15
<211> LENGTH: 426
<212> TYPE: PRT
<213> ORGANISM: Mus musculus

<400> SEQUENCE: 15

Met Ala Thr Val Thr Tyr Pro Ser Ser Glu Pro Met Thr Leu Asp Pro
1               5                   10                  15

Gly Asn Thr Ser Ser Thr Trp Pro Leu Asp Thr Thr Leu Gly Asn Thr
                20                  25                  30

Ser Ala Gly Ala Ser Leu Thr Gly Leu Ala Val Ser Gly Ile Leu Ile
            35                  40                  45

Ser Leu Val Tyr Leu Val Val Cys Val Val Gly Leu Leu Gly Asn Ser
        50                  55                  60

Leu Val Ile Tyr Val Val Leu Arg His Thr Ser Ser Pro Ser Val Thr
65                  70                  75                  80

Ser Val Tyr Ile Leu Asn Leu Ala Leu Ala Asp Glu Leu Phe Met Leu
                85                  90                  95

Gly Leu Pro Phe Leu Ala Ala Gln Asn Ala Leu Ser Tyr Trp Pro Phe
            100                 105                 110

Gly Leu Met Cys Arg Leu Val Met Ala Val Asp Gly Ile Asn Gln Phe
        115                 120                 125

Thr Ser Ile Phe Cys Leu Thr Val Met Ser Val Asp Arg Tyr Leu Ala
    130                 135                 140

Val Val His Pro Thr Arg Ser Ala Arg Trp Arg Thr Ala Pro Val Ala
145                 150                 155                 160

Arg Thr Val Ser Arg Ala Val Trp Val Ala Ser Ala Val Val Val Leu
                165                 170                 175

Pro Val Val Phe Ser Gly Val Pro Arg Gly Met Ser Thr Cys His
            180                 185                 190

Met Gln Trp Pro Glu Pro Ala Ala Trp Arg Thr Ala Phe Ile Ile
        195                 200                 205

Tyr Met Ala Ala Leu Gly Phe Phe Gly Pro Leu Leu Val Ile Cys Leu
    210                 215                 220

Cys Tyr Leu Leu Ile Val Val Lys Val Arg Ser Thr Thr Arg Arg Val
225                 230                 235                 240

Arg Ala Pro Ser Cys Gln Trp Val Gln Ala Pro Ala Cys Gln Arg Arg
                245                 250                 255
```

```
Arg Arg Ser Glu Arg Val Thr Arg Met Val Val Ala Val Ala
            260                 265                 270

Leu Phe Val Leu Cys Trp Met Pro Phe Tyr Leu Leu Asn Ile Val Asn
        275                 280                 285

Val Val Cys Pro Leu Pro Glu Glu Pro Ala Phe Phe Gly Leu Tyr Phe
        290                 295                 300

Leu Val Val Ala Leu Pro Tyr Ala Asn Ser Cys Ala Asn Pro Ile Leu
305                 310                 315                 320

Tyr Gly Phe Leu Ser Tyr Arg Phe Lys Gln Gly Phe Arg Arg Ile Leu
                325                 330                 335

Leu Arg Pro Ser Arg Arg Ile Arg Ser Gln Glu Pro Gly Gly Pro Pro
                340                 345                 350

Glu Lys Thr Glu Glu Glu Asp Glu Glu Glu Glu Arg Arg Glu
                355                 360                 365

Glu Glu Glu Arg Arg Met Gln Arg Gly Gln Glu Met Asn Gly Arg Leu
                370                 375                 380

Ser Gln Ile Ala Gln Ala Gly Thr Ser Gly Gln Gln Pro Arg Pro Cys
385                 390                 395                 400

Thr Gly Thr Ala Lys Glu Gln Gln Leu Leu Pro Gln Glu Ala Thr Ala
                405                 410                 415

Gly Asp Lys Ala Ser Thr Leu Ser His Leu
                420                 425

<210> SEQ ID NO 16
<211> LENGTH: 426
<212> TYPE: PRT
<213> ORGANISM: Rattus norvegicus

<400> SEQUENCE: 16

Met Ala Ala Val Thr Tyr Pro Ser Ser Val Pro Thr Thr Leu Asp Pro
1               5                   10                  15

Gly Asn Ala Ser Ser Ala Trp Pro Leu Asp Thr Ser Leu Gly Asn Ala
                20                  25                  30

Ser Ala Gly Thr Ser Leu Ala Gly Leu Ala Val Ser Gly Ile Leu Ile
            35                  40                  45

Ser Leu Val Tyr Leu Val Val Cys Val Val Gly Leu Leu Gly Asn Ser
        50                  55                  60

Leu Val Ile Tyr Val Val Leu Arg His Thr Ser Ser Pro Ser Val Thr
65                  70                  75                  80

Ser Val Tyr Ile Leu Asn Leu Ala Leu Ala Asp Glu Leu Phe Met Leu
                85                  90                  95

Gly Leu Pro Phe Leu Ala Ala Gln Asn Ala Leu Ser Tyr Trp Pro Phe
            100                 105                 110

Gly Leu Met Cys Arg Leu Val Met Ala Val Asp Gly Ile Asn Gln Phe
        115                 120                 125

Thr Ser Ile Phe Cys Leu Thr Val Met Ser Val Asp Arg Tyr Leu Ala
130                 135                 140

Val Val His Pro Thr Arg Ser Ala Arg Trp Arg Thr Ala Pro Val Ala
145                 150                 155                 160

Arg Met Val Ser Ala Ala Val Trp Val Ala Ser Ala Val Val Leu
                165                 170                 175

Pro Val Val Val Phe Ser Gly Val Pro Arg Gly Met Ser Thr Cys His
            180                 185                 190

Met Gln Trp Pro Glu Pro Ala Ala Ala Trp Arg Thr Ala Phe Ile Ile
```

```
                195                 200                 205
Tyr Thr Ala Ala Leu Gly Phe Phe Gly Pro Leu Leu Val Ile Cys Leu
    210                 215                 220

Cys Tyr Leu Leu Ile Val Val Lys Val Arg Ser Thr Thr Arg Arg Val
225                 230                 235                 240

Arg Ala Pro Ser Cys Gln Trp Val Gln Ala Pro Ala Cys Gln Arg Arg
                245                 250                 255

Arg Arg Ser Glu Arg Arg Val Thr Arg Met Val Val Ala Val Val Ala
            260                 265                 270

Leu Phe Val Leu Cys Trp Met Pro Phe Tyr Leu Leu Asn Ile Val Asn
        275                 280                 285

Val Val Cys Pro Leu Pro Glu Glu Pro Ala Phe Phe Gly Leu Tyr Phe
    290                 295                 300

Leu Val Val Ala Leu Pro Tyr Ala Asn Ser Cys Ala Asn Pro Ile Leu
305                 310                 315                 320

Tyr Gly Phe Leu Ser Tyr Arg Phe Lys Gln Gly Phe Arg Arg Ile Leu
                325                 330                 335

Leu Arg Pro Ser Arg Arg Val Arg Ser Gln Glu Pro Gly Gly Pro Pro
            340                 345                 350

Glu Lys Thr Glu Glu Glu Asp Glu Glu Glu Glu Glu Arg Arg Glu
        355                 360                 365

Glu Glu Glu Arg Arg Met Gln Arg Gln Glu Met Asn Gly Arg Leu
    370                 375                 380

Ser Gln Ile Ala Gln Pro Gly Pro Ser Gly Gln Gln Arg Pro Cys
385                 390                 395                 400

Thr Gly Thr Ala Lys Glu Gln Gln Leu Leu Pro Gln Glu Ala Thr Ala
                405                 410                 415

Gly Asp Lys Ala Ser Thr Leu Ser His Leu
            420                 425

<210> SEQ ID NO 17
<211> LENGTH: 418
<212> TYPE: PRT
<213> ORGANISM: Homo sapiens

<400> SEQUENCE: 17

Met Asp Met Leu His Pro Ser Ser Val Ser Thr Thr Ser Glu Pro Glu
1               5                   10                  15

Asn Ala Ser Ser Ala Trp Pro Pro Asp Ala Thr Leu Gly Asn Val Ser
                20                  25                  30

Ala Gly Pro Ser Pro Ala Gly Leu Ala Val Ser Gly Val Leu Ile Pro
            35                  40                  45

Leu Val Tyr Leu Val Val Cys Val Val Gly Leu Leu Gly Asn Ser Leu
    50                  55                  60

Val Ile Tyr Val Val Leu Arg His Thr Ala Ser Pro Ser Val Thr Asn
65                  70                  75                  80

Val Tyr Ile Leu Asn Leu Ala Leu Ala Asp Glu Leu Phe Met Leu Gly
                85                  90                  95

Leu Pro Phe Leu Ala Ala Gln Asn Ala Leu Ser Tyr Trp Pro Phe Gly
                100                 105                 110

Ser Leu Met Cys Arg Leu Val Met Ala Val Asp Gly Ile Asn Gln Phe
            115                 120                 125

Thr Ser Ile Phe Cys Leu Thr Val Met Ser Val Asp Arg Tyr Leu Ala
    130                 135                 140
```

```
Val Val His Pro Thr Arg Ser Ala Arg Trp Arg Thr Ala Pro Val Ala
145                 150                 155                 160

Arg Thr Val Ser Ala Ala Val Trp Val Ala Ser Ala Val Val Val Leu
            165                 170                 175

Pro Val Val Val Phe Ser Gly Val Pro Arg Gly Met Ser Thr Cys His
        180                 185                 190

Met Gln Trp Pro Glu Pro Ala Ala Trp Arg Ala Gly Phe Ile Ile
    195                 200                 205

Tyr Thr Ala Ala Leu Gly Phe Phe Gly Pro Leu Leu Val Ile Cys Leu
210                 215                 220

Cys Tyr Leu Leu Ile Val Val Lys Val Arg Ser Ala Gly Arg Arg Val
225                 230                 235                 240

Trp Ala Pro Ser Cys Gln Arg Arg Arg Ser Glu Arg Arg Val Thr
                245                 250                 255

Arg Met Val Val Ala Val Val Ala Leu Phe Val Leu Cys Trp Met Pro
            260                 265                 270

Phe Tyr Val Leu Asn Ile Val Asn Val Val Cys Pro Leu Pro Glu Glu
        275                 280                 285

Pro Ala Phe Phe Gly Leu Tyr Phe Leu Val Val Ala Leu Pro Tyr Ala
    290                 295                 300

Asn Ser Cys Ala Asn Pro Ile Leu Tyr Gly Phe Leu Ser Tyr Arg Phe
305                 310                 315                 320

Lys Gln Gly Phe Arg Arg Val Leu Leu Arg Pro Ser Arg Arg Val Arg
                325                 330                 335

Ser Gln Glu Pro Thr Val Gly Pro Pro Glu Lys Thr Glu Glu Asp
            340                 345                 350

Glu Glu Glu Glu Asp Gly Glu Glu Ser Arg Glu Gly Gly Lys Gly Lys
        355                 360                 365

Glu Met Asn Gly Arg Val Ser Gln Ile Thr Gln Pro Gly Thr Ser Gly
    370                 375                 380

Gln Glu Arg Pro Pro Ser Arg Val Ala Ser Lys Glu Gln Gln Leu Leu
385                 390                 395                 400

Pro Gln Glu Ala Ser Thr Gly Glu Lys Ser Ser Thr Met Arg Ile Ser
                405                 410                 415

Tyr Leu

<210> SEQ ID NO 18
<211> LENGTH: 385
<212> TYPE: PRT
<213> ORGANISM: Mus musculus

<400> SEQUENCE: 18

Met Val Leu Lys Met Gly Pro Val Gly Ala Glu Ala Asp Glu Asn Gln
1               5                   10                  15

Thr Val Glu Val Lys Val Glu Pro Tyr Gly Pro Gly His Thr Thr Pro
            20                  25                  30

Arg Gly Glu Leu Pro Pro Asp Pro Glu Pro Glu Leu Ile Asp Ser Thr
        35                  40                  45

Lys Leu Val Glu Val Gln Val Ile Leu Ile Leu Ala Tyr Cys Ser Ile
    50                  55                  60

Ile Leu Leu Gly Val Val Gly Asn Ser Leu Val Ile His Val Val Ile
65                  70                  75                  80

Lys Phe Lys Ser Met Arg Thr Val Thr Asn Phe Phe Ile Ala Asn Leu
                85                  90                  95
```

```
Ala Val Ala Asp Leu Leu Val Asn Thr Leu Cys Leu Pro Phe Thr Leu
            100                 105                 110

Thr Tyr Thr Leu Met Gly Glu Trp Lys Met Gly Pro Val Leu Cys His
        115                 120                 125

Leu Val Pro Tyr Ala Gln Gly Leu Ala Val Gln Val Ser Thr Ile Thr
    130                 135                 140

Leu Thr Val Ile Ala Leu Asp Arg His Arg Cys Ile Val Tyr His Leu
145                 150                 155                 160

Glu Ser Lys Ile Ser Lys Arg Ile Ser Phe Leu Ile Ile Gly Leu Ala
                165                 170                 175

Trp Gly Ile Ser Ala Leu Leu Ala Ser Pro Leu Ala Ile Phe Arg Glu
            180                 185                 190

Tyr Ser Leu Ile Glu Ile Ile Pro Asp Phe Glu Ile Val Ala Cys Thr
        195                 200                 205

Glu Lys Trp Pro Gly Glu Glu Lys Ser Val Tyr Gly Thr Val Tyr Ser
    210                 215                 220

Leu Ser Thr Leu Leu Ile Leu Tyr Val Leu Pro Leu Gly Ile Ile Ser
225                 230                 235                 240

Phe Ser Tyr Thr Arg Ile Trp Ser Lys Leu Arg Asn His Val Ser Pro
                245                 250                 255

Gly Ala Ala Ser Asp His Tyr His Gln Arg Arg His Lys Met Thr Lys
            260                 265                 270

Met Leu Val Cys Val Val Val Phe Ala Val Ser Trp Leu Pro Leu
        275                 280                 285

His Ala Phe Gln Leu Ala Val Asp Ile Asp Ser His Val Leu Asp Leu
    290                 295                 300

Lys Glu Tyr Lys Leu Ile Phe Thr Val Phe His Ile Ile Ala Met Cys
305                 310                 315                 320

Ser Thr Phe Ala Asn Pro Leu Leu Tyr Gly Trp Met Asn Ser Asn Tyr
                325                 330                 335

Arg Lys Ala Phe Leu Ser Ala Phe Arg Cys Glu Gln Arg Leu Asp Ala
            340                 345                 350

Ile His Ser Glu Val Ser Met Thr Phe Lys Ala Lys Lys Asn Leu Glu
        355                 360                 365

Val Lys Lys Asn Asn Gly Pro Thr Asp Ser Phe Ser Glu Ala Thr Asn
    370                 375                 380

Val
385

<210> SEQ ID NO 19
<211> LENGTH: 444
<212> TYPE: PRT
<213> ORGANISM: Homo sapiens

<400> SEQUENCE: 19

Met Ser Gly Thr Lys Leu Glu Asp Ser Pro Pro Cys Arg Asn Trp Ser
1               5                   10                  15

Ser Ala Ser Glu Leu Asn Glu Thr Gln Glu Pro Phe Leu Asn Pro Thr
            20                  25                  30

Asp Tyr Asp Asp Glu Glu Phe Leu Arg Tyr Leu Trp Arg Glu Tyr Leu
        35                  40                  45

His Pro Lys Glu Tyr Glu Trp Val Leu Ile Ala Gly Tyr Ile Ile Val
    50                  55                  60

Phe Val Val Ala Leu Ile Gly Asn Val Leu Val Cys Val Ala Val Trp
65                  70                  75                  80
```

-continued

```
Lys Asn His His Met Arg Thr Val Thr Asn Tyr Phe Ile Val Asn Leu
                85                  90                  95

Ser Leu Ala Asp Val Leu Val Thr Ile Thr Cys Leu Pro Ala Thr Leu
            100                 105                 110

Val Val Asp Ile Thr Glu Thr Trp Phe Phe Gly Gln Ser Leu Cys Lys
        115                 120                 125

Val Ile Pro Tyr Leu Gln Thr Val Ser Val Ser Val Leu Thr
    130                 135                 140

Leu Ser Cys Ile Ala Leu Asp Arg Trp Tyr Ala Ile Cys His Pro Leu
145                 150                 155                 160

Met Phe Lys Ser Thr Ala Lys Arg Ala Arg Asn Ser Ile Val Ile Ile
                165                 170                 175

Trp Ile Val Ser Cys Ile Ile Met Ile Pro Gln Ala Ile Val Met Glu
            180                 185                 190

Cys Ser Thr Val Phe Pro Gly Leu Ala Asn Lys Thr Thr Leu Phe Thr
        195                 200                 205

Val Cys Asp Glu Arg Trp Gly Gly Glu Ile Tyr Pro Lys Met Tyr His
    210                 215                 220

Ile Cys Phe Phe Leu Val Thr Tyr Met Ala Pro Leu Cys Leu Met Val
225                 230                 235                 240

Leu Ala Tyr Leu Gln Ile Phe Arg Lys Leu Trp Cys Arg Gln Ile Pro
                245                 250                 255

Gly Thr Ser Ser Val Val Gln Arg Lys Trp Lys Pro Leu Gln Pro Val
            260                 265                 270

Ser Gln Pro Arg Gly Pro Gly Gln Pro Thr Lys Ser Arg Met Ser Ala
        275                 280                 285

Val Ala Ala Glu Ile Lys Gln Ile Arg Ala Arg Arg Lys Thr Ala Arg
    290                 295                 300

Met Leu Met Val Val Leu Leu Val Phe Ala Ile Cys Tyr Leu Pro Ile
305                 310                 315                 320

Ser Ile Leu Asn Val Leu Lys Arg Val Phe Gly Met Phe Ala His Thr
                325                 330                 335

Glu Asp Arg Glu Thr Val Tyr Ala Trp Phe Thr Phe Ser His Trp Leu
            340                 345                 350

Val Tyr Ala Asn Ser Ala Ala Asn Pro Ile Ile Tyr Asn Phe Leu Ser
        355                 360                 365

Gly Lys Phe Arg Glu Glu Phe Lys Ala Ala Phe Ser Cys Cys Cys Leu
    370                 375                 380

Gly Val His His Arg Gln Glu Asp Arg Leu Thr Arg Gly Arg Thr Ser
385                 390                 395                 400

Thr Glu Ser Arg Lys Ser Leu Thr Thr Gln Ile Ser Asn Phe Asp Asn
                405                 410                 415

Ile Ser Lys Leu Ser Glu Gln Val Val Leu Thr Ser Ile Ser Thr Leu
            420                 425                 430

Pro Ala Ala Asn Gly Ala Gly Pro Leu Gln Asn Trp
        435                 440

<210> SEQ ID NO 20
<211> LENGTH: 44
<212> TYPE: PRT
<213> ORGANISM: Homo sapiens

<400> SEQUENCE: 20

Met Ser Pro Glu Cys Ala Arg Ala Ala Gly Asp Ala Pro Leu Arg Ser
```

```
                1               5                  10                 15
Leu Glu Gln Ala Asn Arg Thr Arg Phe Pro Phe Phe Ser Asp Val Lys
                        20                  25                  30

Gly Asp His Arg Leu Val Leu Ala Ala Val Glu Thr
            35                  40

<210> SEQ ID NO 21
<211> LENGTH: 7
<212> TYPE: PRT
<213> ORGANISM: Homo sapiens

<400> SEQUENCE: 21

Ala Arg Arg Arg Arg Arg Gly
1               5

<210> SEQ ID NO 22
<211> LENGTH: 14
<212> TYPE: PRT
<213> ORGANISM: Homo sapiens

<400> SEQUENCE: 22

Arg Trp Thr Glu Ala Trp Leu Leu Gly Pro Val Ala Cys His
1               5                   10

<210> SEQ ID NO 23
<211> LENGTH: 21
<212> TYPE: PRT
<213> ORGANISM: Homo sapiens

<400> SEQUENCE: 23

Glu Arg Met Val Cys Ile Val His Leu Gln Arg Gly Val Arg Gly Pro
1               5                   10                  15

Gly Arg Arg Ala Arg
            20

<210> SEQ ID NO 24
<211> LENGTH: 31
<212> TYPE: PRT
<213> ORGANISM: Homo sapiens

<400> SEQUENCE: 24

Arg Val Val Pro Gln Arg Leu Pro Gly Ala Asp Gln Glu Ile Ser Ile
1               5                   10                  15

Cys Thr Leu Ile Trp Pro Thr Ile Pro Gly Glu Ile Ser Trp Asp
                20                  25                  30

<210> SEQ ID NO 25
<211> LENGTH: 37
<212> TYPE: PRT
<213> ORGANISM: Homo sapiens

<400> SEQUENCE: 25

Lys Ile Leu Gln Ile Thr Lys Ala Ser Arg Lys Arg Leu Thr Val Ser
1               5                   10                  15

Leu Ala Tyr Ser Glu Ser His Gln Ile Arg Val Ser Gln Gln Asp Phe
                20                  25                  30

Arg Leu Phe Arg Thr
            35

<210> SEQ ID NO 26
<211> LENGTH: 6
<212> TYPE: PRT
```

```
<213> ORGANISM: Homo sapiens

<400> SEQUENCE: 26

Gln Asn Phe Lys Gln Asp
1               5

<210> SEQ ID NO 27
<211> LENGTH: 45
<212> TYPE: PRT
<213> ORGANISM: Homo sapiens

<400> SEQUENCE: 27

Asn Pro Ile Leu Tyr Asn Met Thr Leu Cys Arg Asn Glu Trp Lys Lys
1               5                   10                  15

Ile Phe Cys Cys Phe Trp Phe Pro Glu Lys Gly Ala Ile Leu Thr Asp
            20                  25                  30

Thr Ser Val Lys Arg Asn Asp Leu Ser Ile Ile Ser Gly
        35                  40                  45

<210> SEQ ID NO 28
<211> LENGTH: 13
<212> TYPE: PRT
<213> ORGANISM: Homo sapiens

<400> SEQUENCE: 28

Gln Ile Thr Lys Ala Ser Arg Lys Arg Leu Thr Val Ser
1               5                   10

<210> SEQ ID NO 29
<211> LENGTH: 13
<212> TYPE: PRT
<213> ORGANISM: Homo sapiens

<400> SEQUENCE: 29

Ile Leu Thr Asp Thr Ser Val Lys Arg Asn Asp Leu Ser
1               5                   10

<210> SEQ ID NO 30
<211> LENGTH: 14
<212> TYPE: PRT
<213> ORGANISM: Homo sapiens

<400> SEQUENCE: 30

His Gln Ile Arg Val Ser Gln Gln Asp Phe Arg Leu Phe Arg
1               5                   10

<210> SEQ ID NO 31
<211> LENGTH: 14
<212> TYPE: PRT
<213> ORGANISM: Homo sapiens

<400> SEQUENCE: 31

Thr Lys Ala Ser Arg Lys Arg Leu Thr Val Ser Leu Ala Tyr
1               5                   10

<210> SEQ ID NO 32
<211> LENGTH: 14
<212> TYPE: PRT
<213> ORGANISM: Homo sapiens

<400> SEQUENCE: 32

Ser Leu Glu Gln Ala Asn Arg Thr Arg Phe Pro Phe Phe Ser
1               5                   10
```

<210> SEQ ID NO 33
<211> LENGTH: 14
<212> TYPE: PRT
<213> ORGANISM: Homo sapiens

<400> SEQUENCE: 33

Asn Pro Ile Leu Tyr Asn Met Thr Leu Cys Arg Asn Glu Trp
1               5                   10

<210> SEQ ID NO 34
<211> LENGTH: 16
<212> TYPE: PRT
<213> ORGANISM: Homo sapiens

<400> SEQUENCE: 34

Ala Val Ser Leu Leu Gly Asn Val Cys Ala Leu Val Leu Val Ala Arg
1               5                   10                  15

<210> SEQ ID NO 35
<211> LENGTH: 16
<212> TYPE: PRT
<213> ORGANISM: Homo sapiens

<400> SEQUENCE: 35

Arg Arg Arg Arg Arg Gly Ala Thr Ala Cys Leu Val Leu Asn Leu Phe
1               5                   10                  15

<210> SEQ ID NO 36
<211> LENGTH: 16
<212> TYPE: PRT
<213> ORGANISM: Homo sapiens

<400> SEQUENCE: 36

Trp Phe Pro Glu Lys Gly Ala Ile Leu Thr Asp Thr Ser Val Lys Arg
1               5                   10                  15

<210> SEQ ID NO 37
<211> LENGTH: 19
<212> TYPE: DNA
<213> ORGANISM: Homo sapiens

<400> SEQUENCE: 37
tctgcctctc tgcgtcttc                                              19

<210> SEQ ID NO 38
<211> LENGTH: 20
<212> TYPE: DNA
<213> ORGANISM: Homo sapiens

<400> SEQUENCE: 38
agtcctggca ccaagaagtt                                             20

<210> SEQ ID NO 39
<211> LENGTH: 17
<212> TYPE: DNA
<213> ORGANISM: Homo sapiens

<400> SEQUENCE: 39
agccgagcca catcgct                                                17

<210> SEQ ID NO 40
<211> LENGTH: 19
<212> TYPE: DNA
<213> ORGANISM: Homo sapiens -continued

```
<400> SEQUENCE: 40
gtgaccaggc gcccaatac                                                     19

<210> SEQ ID NO 41
<211> LENGTH: 28
<212> TYPE: DNA
<213> ORGANISM: Homo sapiens

<400> SEQUENCE: 41
caaatccgtt gactccgacc ttcacctt                                           28

<210> SEQ ID NO 42
<211> LENGTH: 39
<212> TYPE: DNA
<213> ORGANISM: Homo sapiens

<400> SEQUENCE: 42
gcagcagcgg ccgcaccgtg ctggtgctca tctttgcag                               39

<210> SEQ ID NO 43
<211> LENGTH: 33
<212> TYPE: DNA
<213> ORGANISM: Homo sapiens

<400> SEQUENCE: 43
gcagcagtcg acgccagaaa taatcgacaa gtc                                     33

<210> SEQ ID NO 44
<211> LENGTH: 39
<212> TYPE: DNA
<213> ORGANISM: Homo sapiens

<400> SEQUENCE: 44
gcagcagcgg ccgcatgtcc cctgaatgcg cgcgggcag                               39

<210> SEQ ID NO 45
<211> LENGTH: 37
<212> TYPE: DNA
<213> ORGANISM: Homo sapiens

<400> SEQUENCE: 45
gcagcagtcg acgtttaggg ctgaattagc aaatgtg                                 37

<210> SEQ ID NO 46
<211> LENGTH: 22
<212> TYPE: DNA
<213> ORGANISM: Homo sapiens

<400> SEQUENCE: 46
tcacaaaggc atcaaggaag ag                                                 22

<210> SEQ ID NO 47
<211> LENGTH: 17
<212> TYPE: DNA
<213> ORGANISM: Homo sapiens

<400> SEQUENCE: 47
tgggacacgc ggatctg                                                       17

<210> SEQ ID NO 48
<211> LENGTH: 26
<212> TYPE: DNA
```

-continued

```
<213> ORGANISM: Homo sapiens

<400> SEQUENCE: 48
ctctccgagt aggccaggct taccgt                                    26

<210> SEQ ID NO 49
<211> LENGTH: 19
<212> TYPE: DNA
<213> ORGANISM: Homo sapiens

<400> SEQUENCE: 49
tctgcctctc tgcgtcttc                                            19

<210> SEQ ID NO 50
<211> LENGTH: 20
<212> TYPE: DNA
<213> ORGANISM: Homo sapiens

<400> SEQUENCE: 50
agtcctggca ccaagaagtt                                           20
```

What is claimed is:

1. A method of diagnosing renal tumors comprising:
   a) determining the expression level of RNA encoding a polypeptide comprising the sequence of amino acids 2 of 361 of SEQ ID NO:2 in a normal kidney sample by measuring RNA of said polypeptide; and
   b) comparing said expression level of said RNA from a kidney test sample;
   wherein an elevated expression level of said RNA in said test sample relative to the expression level of said RNA in said normal sample is indicative of renal tumors-or a predisposition to renal tumors.

2. The method according to claim 1, wherein said RNA measurement comprises hybridization between said RNA the complete complementary sequence of to a member of the group consisting of:

a.) an isolated nucleic acid comprising SEQ ID NO:1;
b.) an isolated nucleic acid comprising nucleotides 1 to 1083 of SEQ ID NO:1;
c.) an isolated nucleic acid comprising nucleotides 4 to 1083 of SEQ ID NO:1; and
d.) an isolated nucleic acid comprising the HGPRBMY18 cDNA clone contained in ATCC Deposit No. PTA-2766, and
wherein said hybridization is performed under conditions at least as stringent as hybridization in 50% formamide, 5× Denhardt's solution, 5×SSPE (or SSC), 0.2% SDS at 42° C., followed by washing in 0.2×SSPE (or SSC) and 0.2% SDS at a temperature of about 45° C.

* * * * *

UNITED STATES PATENT AND TRADEMARK OFFICE
CERTIFICATE OF CORRECTION

| | | |
|---|---|---|
| PATENT NO. | : 7,115,375 B2 | Page 1 of 54 |
| APPLICATION NO. | : 10/768878 | |
| DATED | : October 3, 2006 | |
| INVENTOR(S) | : John N. Feder, Gabriel A. Mintier and Chandra S. Ramanathan | |

It is certified that error appears in the above-identified patent and that said Letters Patent is hereby corrected as shown below:

(73) Assignee - should read --Bristol-Myers Squibb Company--

Column 73

Please replace Sequence Listing from column 73 through column 114 with the below:

```
                        SEQUENCE LISTING

<110>   Bristol-Myers Squibb Company

<120>   METHODS OF DIAGNOSING RENAL TUMORS USING THE HUMAN G-PROTEIN
        COUPLED RECEPTOR, HGPRBMY18

<130>   D0048B CIP2

<140>   US 10/768,878
<141>   2004-01-30

<150>   U.S. 09/992,331
<151>   2001-11-14

<150>   U.S. 60/248,483
<151>   2000-11-14

<150>   U.S. 10/262,313
<151>   2002-09-30

<150>   U.S. 60/261,782
<151>   2001-01-16

<150>   U.S. 60/308,540
<151>   2001-07-27
```

UNITED STATES PATENT AND TRADEMARK OFFICE
CERTIFICATE OF CORRECTION

PATENT NO.         : 7,115,375 B2
APPLICATION NO.    : 10/768878
DATED              : October 3, 2006
INVENTOR(S)        : John N. Feder, Gabriel A. Mintier and Chandra S. Ramanathan It is certified that error appears in the above-identified patent and that said Letters Patent is hereby corrected as shown below:

```
<160>  50

<170>  PatentIn version 3.2

<210>  1
<211>  1086
<212>  DNA
<213>  Homo sapiens

<400>  1
atgtcccctg aatgcgcgcg ggcagcgggc gacgcgccct tgcgcagcct ggagcaagcc    60
aaccgcaccc gctttcccct cttctccgac gtcaagggcg accaccggct ggtgctggcc   120
gcggtggaga caaccgtgct ggtgctcatc tttgcagtgt cgctgctggg caacgtgtgc   180
gccctggtgc tggtggcgcg ccgacgacgc cgcggcgcga ctgcctgcct ggtactcaac   240
ctcttctgcg cggacctgct cttcatcagc gctatccctc tggtgctggc cgtgcgctgg   300
actgaggcct ggctgctggg ccccgttgcc tgccacctgc tcttctacgt gatgaccctg   360
agcggcagcg tcaccatcct cacgctggcc gcggtcagcc tggagcgcat ggtgtgcatc   420
gtgcacctgc agcgcggcgt gcggggtcct gggcggcggg cgcgggcagt gctgctggcg   480
ctcatctggg gctattcggc ggtcgccgct ctgcctctct gcgtcttctt ccgagtcgtc   540
ccgcaacggc tccccggcgc cgaccaggaa atttcgattt gcacactgat ttggcccacc   600
attcctggag agatctcgtg ggatgtctct tttgttactt tgaacttctt ggtgccagga   660
ctggtcattg tgatcagtta ctccaaaatt ttacagatca caaaggcatc aaggaagagg   720
ctcacggtaa gcctggccta ctcggagagc caccagatcc gcgtgtccca gcaggacttc   780
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
cggctcttcc gcaccctctt cctcctcatg gtctccttct tcatcatgtg gagccccatc   840
atcatcacca tcctcctcat cctgatccag aacttcaagc aagacctggt catctggccg   900
tccctcttct tctgggtggt ggccttcaca tttgctaatt cagccctaaa ccccatcctc   960
tacaacatga cactgtgcag gaatgagtgg aagaaaattt tttgctgctt ctggttccca   1020
gaaaagggag ccattttaac agacacatct gtcaaaagaa atgacttgtc gattatttct   1080
ggctaa                                                              1086
```

<210> 2
<211> 361
<212> PRT
<213> Homo sapiens

<400> 2

Met Ser Pro Glu Cys Ala Arg Ala Ala Gly Asp Ala Pro Leu Arg Ser
1               5                   10                  15

Leu Glu Gln Ala Asn Arg Thr Arg Phe Pro Phe Phe Ser Asp Val Lys
            20                  25                  30

Gly Asp His Arg Leu Val Leu Ala Ala Val Glu Thr Thr Val Leu Val
        35                  40                  45

Leu Ile Phe Ala Val Ser Leu Leu Gly Asn Val Cys Ala Leu Val Leu
    50                  55                  60

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Val Ala Arg Arg Arg Arg Arg Gly Ala Thr Ala Cys Leu Val Leu Asn
 65              70              75                       80

Leu Phe Cys Ala Asp Leu Leu Phe Ile Ser Ala Ile Pro Leu Val Leu
             85              90                       95

Ala Val Arg Trp Thr Glu Ala Trp Leu Leu Gly Pro Val Ala Cys His
            100             105                 110

Leu Leu Phe Tyr Val Met Thr Leu Ser Gly Ser Val Thr Ile Leu Thr
            115             120                 125

Leu Ala Ala Val Ser Leu Glu Arg Met Val Cys Ile Val His Leu Gln
 130             135                 140

Arg Gly Val Arg Gly Pro Gly Arg Arg Ala Arg Ala Val Leu Leu Ala
 145             150             155                      160

Leu Ile Trp Gly Tyr Ser Ala Val Ala Ala Leu Pro Leu Cys Val Phe
             165             170                 175

Phe Arg Val Val Pro Gln Arg Leu Pro Gly Ala Asp Gln Glu Ile Ser
             180             185                 190

Ile Cys Thr Leu Ile Trp Pro Thr Ile Pro Gly Glu Ile Ser Trp Asp
             195             200                 205
```

UNITED STATES PATENT AND TRADEMARK OFFICE
CERTIFICATE OF CORRECTION

PATENT NO.        : 7,115,375 B2                                        Page 5 of 54
APPLICATION NO. : 10/768878
DATED             : October 3, 2006
INVENTOR(S)      : John N. Feder, Gabriel A. Mintier and Chandra S. Ramanathan It is certified that error appears in the above-identified patent and that said Letters Patent is hereby corrected as shown below:

```
Val Ser Phe Val Thr Leu Asn Phe Leu Val Pro Gly Leu Val Ile Val
    210             215             220

Ile Ser Tyr Ser Lys Ile Leu Gln Ile Thr Lys Ala Ser Arg Lys Arg
225             230             235                         240

Leu Thr Val Ser Leu Ala Tyr Ser Glu Ser His Gln Ile Arg Val Ser
            245             250                 255

Gln Gln Asp Phe Arg Leu Phe Arg Thr Leu Phe Leu Leu Met Val Ser
            260             265             270

Phe Phe Ile Met Trp Ser Pro Ile Ile Ile Thr Ile Leu Leu Ile Leu
        275             280             285

Ile Gln Asn Phe Lys Gln Asp Leu Val Ile Trp Pro Ser Leu Phe Phe
    290             295             300

Trp Val Val Ala Phe Thr Phe Ala Asn Ser Ala Leu Asn Pro Ile Leu
305             310             315                         320

Tyr Asn Met Thr Leu Cys Arg Asn Glu Trp Lys Lys Ile Phe Cys Cys
                325             330                     335

Phe Trp Phe Pro Glu Lys Gly Ala Ile Leu Thr Asp Thr Ser Val Lys
            340             345             350
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Arg Asn Asp Leu Ser Ile Ile Ser Gly
        355                 360

<210>  3
<211>  1438
<212>  DNA
<213>  Homo sapiens

<400>  3
ccacgcgtcc gcggacgcgt gggaagtagc tgggattaca ggtacctgcc accatgccca      60
gctaattttt gtattttag  tagagacggg gtttcaccac gttggccatg gctggtctgg     120
agctcccgac ctcaagtgat ccacccgcct tggcctccca aagtgctgag attacaagca    180
tgagccactg tgcccagtca gtgcttagat ttcttaagac ccaaccttaa gaaagacaat    240
tagaagacag agtgggcaac tgggagaggc ctggtaatat ggcagaggga agaggggtg     300 aaggtgtggg tggcaggagg gtggctggtt ggggaagtgg ccactggatc ttaggccaca    360
ggcatacttt tccatctcca gcttcctcat ttacagaaaa cgagactgca gtggtgtgat    420
ggaaatgtgt gggacgggga caggtgactg gctttcatta ctaaccagag gacagcttag    480
acaagtcact ctggctgggc ctcagtttcc ttatctctaa cgggactgga ttgcccagtg    540
ctcctcaaac tgtggcacct ggggcacatt catagcttgt gtgtgaatct gccagccttg    600
aaatatctgt cttccttgga tggcaagttt attaaaaatt ttggaaggac tcactctttt    660
tataagaaag catttatgtc attgttcaga atgcaaaatg tatatgcatt ttagttacaa    720
taactaatat ttgataacat ttaacgagta attactgtgt gccaagtgtg caaaactcta    780
```

UNITED STATES PATENT AND TRADEMARK OFFICE
CERTIFICATE OF CORRECTION

| | | |
|---|---|---|
| PATENT NO. | : 7,115,375 B2 | |
| APPLICATION NO. | : 10/768878 | |
| DATED | : October 3, 2006 | |
| INVENTOR(S) | : John N. Feder, Gabriel A. Mintier and Chandra S. Ramanathan | |

It is certified that error appears in the above-identified patent and that said Letters Patent is hereby corrected as shown below:

```
ggtgagcctc acaataacct aatggggtat tattattccc attttataga ttaaaaatct    840
ggggtagagg gagtagataa tccacctaaa gacctgttat taagtagtga taaaagatct    900
ccactccctc tctcccccac aaaatatgga ctcattacaa gttgttttag gatctacctc    960
cagacccatg gagtttcttt agtaaagcct gaacgacaca ggccaaaata atctccaaag   1020
gccagctctg acccttttaa atcaatttta gctaaatccg ttcacaaaag gcttcgcaca   1080
tccagtgtcc ctgaaaaata aaggaggttg ggcaggccct gcggggctc gaggaattcg    1140 ctaagtgagt tttctggctt ctggatacac tttcaaaggg ccagagggca cgaggcttcc   1200
gccttggccg ccacctcccc ggccagctgc ggtgttcgcg gccagtgttg ccgggcactt   1260
cctggttccc gcgcgcccg ggtgcagctc cctgcaccca gtgctggcgc tcctcagaag   1320 ggaggggggcc agaggcgaga tgtcgcaacc gcctccctcc ctctttcccc gccttggcac   1380
tcagtcgcct cccagatgag cactctctca gaccgctgcg ggccgccagg cgccggga    1438

<210>  4
<211>  632
<212>  DNA
<213>  Homo sapiens

<400>  4
tttttctttta tagccgagtt tctcacacct ggcgagctgt ggcatgcttt taaacagagt     60
tcatttccag taccctccat cagtgcaccc tgctttaaga aaatgaacct atgcaaatag    120
acatccacag cgtcggtaaa ttaaggggtg atcaccaagt ttcataatat tttcccttta    180
```

UNITED STATES PATENT AND TRADEMARK OFFICE
CERTIFICATE OF CORRECTION

| | | |
|---|---|---|
| PATENT NO. | : 7,115,375 B2 | |
| APPLICATION NO. | : 10/768878 | |
| DATED | : October 3, 2006 | |
| INVENTOR(S) | : John N. Feder, Gabriel A. Mintier and Chandra S. Ramanathan | |

It is certified that error appears in the above-identified patent and that said Letters Patent is hereby corrected as shown below:

```
taaaaggatt tgttggccag gtgcagtggt tcatgcctgt aatcccagca gtttgggagg    240
ctgaggtggg tggatcacct gaggtcagga gttcgagacc aacctgacca acatggtgag    300
acccccgtct ctactaaaaa taaaaaaaaa aattagctgg gagtggtggt gggcacctgt    360
aatcctagct acttgggagg ctgaaccagg agaatctctt gaacctggga ggcagaggtt    420
gcagtgagcc gagatcgtgc cattgcactc caaccagggc aacaagagtg aaactccatc    480
ttaaaaaaaa aaaaaaaaag atttgttatg ggttcctttt aaatgtgaac ttttttagtg    540
tgtttgtaat atgatcaaat ttaataaata tttatttatg actgttaaaa aaaaaaaaaa    600
aaaaaaaaaa aaaaaaaaaa aaaaaaaaaa aa                                  632

<210>  5
<211>  80
<212>  DNA
<213>  Homo sapiens

<400>  5
agcaggtggt cgcccttgac gtcggagaag aagggaaagc gggtgcggtt ggcttgctcc     60
aaggtgaaga agggcgcgta                                                 80

<210>  6
<211>  21
<212>  DNA
<213>  Homo sapiens

<400>  6
gactgcctgc ctggtactca a                                               21
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
<210>  7
<211>  18
<212>  DNA
<213>  Homo sapiens

<400>  7
gccaagcgtg aggatggt                                                          18

<210>  8
<211>  363
<212>  PRT
<213>  Ovis aries

<400>  8

Met Ala Gly Arg Leu Trp Gly Pro Gly Gly Thr Pro Lys Gly Asn Gly
1               5                   10                  15

Ser Ala Leu Leu Asn Val Ser Gln Ala Ala Pro Gly Ala Gly Asp Gly
                20                  25                  30

Val Arg Pro Arg Pro Ser Trp Leu Ala Ala Thr Leu Ala Ser Ile Leu
                35                  40                  45

Ile Phe Thr Ile Val Val Asp Ile Val Gly Asn Leu Leu Val Val Leu
                50                  55                  60

Ser Val Tyr Arg Asn Lys Lys Leu Arg Asn Ala Gly Asn Val Phe Val
65                  70                  75                  80
```

UNITED STATES PATENT AND TRADEMARK OFFICE
CERTIFICATE OF CORRECTION

PATENT NO.         : 7,115,375 B2
APPLICATION NO. : 10/768878
DATED                  : October 3, 2006
INVENTOR(S)       : John N. Feder, Gabriel A. Mintier and Chandra S. Ramanathan It is certified that error appears in the above-identified patent and that said Letters Patent is hereby corrected as shown below:

```
Val Ser Leu Ala Val Ala Asp Leu Leu Val Ala Val Tyr Pro Tyr Pro
                85                  90                  95

Leu Ala Leu Ala Ser Ile Val Asn Asn Gly Trp Ser Leu Ser Ser Leu
                100                 105                 110

His Cys Gln Leu Ser Gly Phe Leu Met Gly Leu Ser Val Ile Gly Val
                115                 120                 125

Phe Ser Ile Thr Gly Ile Ala Ile Asn Arg Tyr Cys Cys Ile Cys His
    130                 135                 140

Ser Leu Arg Tyr Gly Lys Leu Tyr Ser Gly Thr Asn Ser Leu Cys Tyr
145                 150                 155                 160

Val Phe Leu Ile Trp Thr Leu Thr Leu Val Ala Ile Val Pro Asn Leu
                165                 170                 175

Cys Val Gly Thr Leu Gln Tyr Asp Pro Arg Ile Tyr Ser Cys Thr Phe
                180                 185                 190

Thr Gln Ser Val Ser Ser Ala Tyr Thr Ile Ala Val Val Val Phe His
            195                 200                 205

Phe Ile Val Pro Met Leu Val Val Phe Cys Tyr Leu Arg Ile Trp
        210                 215                 220
```

UNITED STATES PATENT AND TRADEMARK OFFICE
CERTIFICATE OF CORRECTION

| | | |
|---|---|---|
| PATENT NO. | : 7,115,375 B2 | Page 11 of 54 |
| APPLICATION NO. | : 10/768878 | |
| DATED | : October 3, 2006 | |
| INVENTOR(S) | : John N. Feder, Gabriel A. Mintier and Chandra S. Ramanathan | |

It is certified that error appears in the above-identified patent and that said Letters Patent is hereby corrected as shown below:

```
Ala Leu Val Leu Gln Val Arg Trp Lys Val Lys Pro Asp Asn Lys Pro
225             230             235             240

Lys Leu Lys Pro Gln Asp Phe Arg Asn Phe Val Thr Met Phe Val Val
            245             250             255

Phe Val Leu Phe Ala Ile Cys Trp Ala Pro Leu Asn Phe Ile Gly Leu
            260             265             270

Val Val Ala Ser Asp Pro Ala Ser Met Ala Pro Arg Ile Pro Glu Trp
            275             280             285

Leu Phe Val Ala Ser Tyr Tyr Met Ala Tyr Phe Asn Ser Cys Leu Asn
    290             295             300

Ala Ile Ile Tyr Gly Leu Leu Asn Gln Asn Phe Arg Gln Glu Tyr Arg
305             310             315             320

Lys Ile Ile Val Ser Leu Cys Thr Thr Lys Met Phe Phe Val Asp Ser
            325             330             335

Ser Asn His Val Ala Asp Arg Ile Lys Arg Lys Pro Ser Pro Leu Ile
            340             345             350

Ala Asn His Asn Leu Ile Lys Val Asp Ser Val
        355             360
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
<210>  9
<211>  363
<212>  PRT
<213>  Ovis aries

<400>  9

Met Ala Gly Arg Leu Trp Gly Pro Gly Gly Thr Pro Lys Gly Asn Gly
1             5                   10                  15

Ser Ala Leu Leu Asn Val Ser Gln Ala Ala Pro Gly Ala Gly Asp Gly
                20                  25                  30

Val Arg Pro Arg Pro Ser Trp Leu Ala Ala Thr Leu Ala Ser Ile Leu
            35                  40                  45

Ile Phe Thr Ile Val Val Asp Ile Val Gly Asn Leu Leu Val Val Leu
        50                  55                  60

Ser Val Tyr Arg Asn Lys Lys Leu Arg Asn Ala Gly Asn Val Phe Val
65                  70                  75                  80

Val Ser Leu Ala Val Ala Asp Leu Leu Val Ala Val Tyr Pro Tyr Pro
                85                  90                  95

Leu Ala Leu Ala Ser Ile Val Asn Asn Gly Trp Ser Leu Ser Ser Leu
                100                 105                 110
```

UNITED STATES PATENT AND TRADEMARK OFFICE
CERTIFICATE OF CORRECTION

| | | |
|---|---|---|
| PATENT NO. | : 7,115,375 B2 | Page 13 of 54 |
| APPLICATION NO. | : 10/768878 | |
| DATED | : October 3, 2006 | |
| INVENTOR(S) | : John N. Feder, Gabriel A. Mintier and Chandra S. Ramanathan | |

It is certified that error appears in the above-identified patent and that said Letters Patent is hereby corrected as shown below:

```
His Cys Gln Leu Ser Gly Phe Leu Met Gly Leu Ser Val Ile Gly Val
        115             120             125

Phe Ser Ile Thr Gly Ile Ala Ile Asn Arg Tyr Cys Cys Ile Cys His
    130             135             140

Ser Leu Arg Tyr Gly Lys Leu Tyr Ser Gly Thr Asn Ser Leu Cys Tyr
145             150             155                         160

Val Phe Leu Ile Trp Thr Leu Thr Leu Val Ala Ile Val Pro Asn Leu
                165             170             175

Cys Val Gly Thr Leu Gln Tyr Asp Pro Arg Ile Tyr Ser Cys Thr Phe
            180             185             190

Thr Gln Ser Val Ser Ser Ala Tyr Thr Ile Ala Val Val Val Phe His
        195             200             205

Phe Ile Val Pro Met Leu Val Val Phe Cys Tyr Leu Arg Ile Trp
    210             215             220

Ala Leu Val Leu Gln Val Arg Trp Lys Val Lys Pro Asp Asn Lys Pro
225             230             235                         240

Lys Leu Lys Pro Gln Asp Phe Arg Asn Phe Val Thr Met Phe Val Val
            245             250             255
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Phe Val Leu Phe Ala Ile Cys Trp Ala Pro Leu Asn Phe Ile Gly Leu
            260                 265                 270

Val Val Ala Ser Asp Pro Asp Ser Met Ala Pro Arg Ile Pro Glu Trp
            275                 280                 285

Leu Phe Val Ala Ser Tyr Tyr Met Ala Tyr Phe Asn Ser Cys Leu Asn
        290                 295                 300

Ala Ile Ile Tyr Gly Leu Leu Asn Gln Asn Phe Arg Gln Glu Tyr Arg
305                 310                 315                 320

Lys Ile Ile Val Ser Leu Cys Thr Thr Lys Met Phe Phe Val Asp Ser
                325                 330                 335

Ser Asn His Val Ala Asp Arg Ile Lys Arg Lys Pro Ser Pro Leu Ile
            340                 345                 350

Ala Asn Arg Asn Leu Val Lys Val Asp Ser Val
        355                 360

<210>   10
<211>   347
<212>   PRT
<213>   Mus musculus

<400>   10
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Met Glu Leu Ala Met Val Asn Leu Ser Glu Gly Asn Gly Asp Pro Glu
 1               5                  10                  15

Pro Pro Ala Pro Glu Ser Arg Pro Leu Phe Gly Ile Gly Val Glu Asn
            20                  25                  30

Phe Ile Thr Leu Val Val Phe Gly Leu Ile Phe Ala Met Gly Val Leu
        35                  40                  45

Gly Asn Ser Leu Val Ile Thr Val Leu Ala Arg Ser Lys Pro Gly Lys
    50                  55                  60

Pro Arg Ser Thr Thr Asn Leu Phe Ile Leu Asn Leu Ser Ile Ala Asp
65                  70                  75                  80

Leu Ala Tyr Leu Leu Phe Cys Ile Pro Phe Gln Ala Thr Val Tyr Ala
            85                  90                  95

Leu Pro Thr Trp Val Leu Gly Ala Phe Ile Cys Lys Phe Ile His Tyr
            100                 105                 110

Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
        130                 135                 140
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Leu Arg Val Ser Arg Asn Ala Leu Leu Gly Val Gly Phe Ile Trp Ala
145                 150                 155                 160

Leu Ser Ile Ala Met Ala Ser Pro Val Ala Tyr His Gln Arg Leu Phe
                165             170                 175

His Arg Asp Ser Asn Gln Thr Phe Cys Trp Glu Gln Trp Pro Asn Lys
                180              185                 190

Leu His Lys Lys Ala Tyr Val Val Cys Thr Phe Val Phe Gly Tyr Leu
            195             200                 205

Leu Pro Leu Leu Leu Ile Cys Phe Cys Tyr Ala Lys Val Leu Asn His
    210                 215             220

Leu His Lys Lys Leu Lys Asn Met Ser Lys Lys Ser Glu Ala Ser Lys
225                 230             235                 240

Lys Lys Thr Ala Gln Thr Val Leu Val Val Val Val Phe Gly Ile
                245             250                 255

Ser Trp Leu Pro His His Val Val His Leu Trp Ala Glu Phe Gly Ala
                260             265                 270

Phe Pro Leu Thr Pro Ala Ser Phe Phe Arg Ile Thr Ala His Cys
            275             280                 285
```

UNITED STATES PATENT AND TRADEMARK OFFICE
CERTIFICATE OF CORRECTION

PATENT NO.         : 7,115,375 B2
APPLICATION NO. : 10/768878
DATED                  : October 3, 2006
INVENTOR(S)        : John N. Feder, Gabriel A. Mintier and Chandra S. Ramanathan It is certified that error appears in the above-identified patent and that said Letters Patent is hereby corrected as shown below:

```
Leu Ala Tyr Ser Asn Ser Ser Val Asn Pro Ile Ile Tyr Ala Phe Leu
    290             295             300

Ser Glu Asn Phe Arg Lys Ala Tyr Lys Gln Val Phe Lys Cys His Val
305             310             315                         320

Cys Asp Glu Ser Pro Arg Ser Glu Thr Lys Glu Asn Lys Ser Arg Met
                325             330             335

Asp Thr Pro Pro Ser Thr Asn Cys Thr His Val
            340             345

<210> 11
<211> 345
<212> PRT
<213> Rattus norvegicus

<400> 11

Met Glu Leu Ala Pro Val Asn Leu Ser Glu Gly Asn Gly Asp Pro Glu
1               5               10              15

Pro Pro Ala Glu Pro Arg Pro Leu Phe Gly Ile Gly Val Glu Asn Phe
            20              25              30

Ile Thr Leu Val Val Phe Gly Leu Ile Phe Ala Met Gly Val Leu Gly
        35              40              45
```

UNITED STATES PATENT AND TRADEMARK OFFICE
CERTIFICATE OF CORRECTION

| | |
|---|---|
| PATENT NO. | : 7,115,375 B2 |
| APPLICATION NO. | : 10/768878 |
| DATED | : October 3, 2006 |
| INVENTOR(S) | : John N. Feder, Gabriel A. Mintier and Chandra S. Ramanathan |

It is certified that error appears in the above-identified patent and that said Letters Patent is hereby corrected as shown below:

```
Asn Ser Leu Val Ile Thr Val Leu Ala Arg Ser Lys Pro Gly Lys Pro
    50              55                  60

Arg Ser Thr Thr Asn Leu Phe Ile Leu Asn Leu Ser Ile Ala Asp Leu
65              70                  75                      80

Ala Tyr Leu Leu Phe Cys Ile Pro Phe Gln Ala Thr Val Tyr Ala Leu
                85              90                  95

Pro Thr Trp Val Leu Gly Ala Phe Ile Cys Lys Phe Ile His Tyr Phe
            100             105                 110

Phe Thr Val Ser Met Leu Val Ser Ile Phe Thr Leu Ala Ala Met Ser
            115             120                 125

Val Asp Arg Tyr Val Ala Ile Val His Ser Arg Arg Ser Ser Ser Leu
    130             135                 140

Arg Val Ser Arg Asn Ala Leu Leu Gly Val Gly Phe Ile Trp Ala Leu
145             150              155                     160

Ser Ile Ala Met Ala Ser Pro Val Ala Tyr Tyr Gln Arg Leu Phe His
                165             170                 175

Arg Asp Ser Asn Gln Thr Phe Cys Trp Glu His Trp Pro Asn Gln Leu
            180             185                 190
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
His Lys Lys Ala Tyr Val Val Cys Thr Phe Val Phe Gly Tyr Leu Leu
    195                 200                 205

Pro Leu Leu Leu Ile Cys Phe Cys Tyr Ala Lys Val Leu Asn His Leu
    210                 215                 220

His Lys Lys Leu Lys Asn Met Ser Lys Lys Ser Glu Ala Ser Lys Lys
225                 230                 235                 240

Lys Thr Ala Gln Thr Val Leu Val Val Val Val Phe Gly Ile Ser
            245                 250                 255

Trp Leu Pro His His Val Ile His Leu Trp Ala Glu Phe Gly Ala Phe
            260                 265                 270

Pro Leu Thr Pro Ala Ser Phe Phe Phe Arg Ile Thr Ala His Cys Leu
            275                 280                 285

Ala Tyr Ser Asn Ser Ser Val Asn Pro Ile Ile Tyr Ala Phe Leu Ser
    290                 295                 300

Glu Asn Phe Arg Lys Ala Tyr Lys Gln Val Phe Lys Cys Arg Val Cys
305                 310                 315                 320

Asn Glu Ser Pro His Gly Asp Ala Lys Glu Lys Asn Arg Ile Asp Thr
            325                 330                 335
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Pro Pro Ser Thr Asn Cys Thr His Val
            340             345

<210>  12
<211>  349
<212>  PRT
<213>  Homo sapiens

<400>  12

Met Glu Leu Ala Val Gly Asn Leu Ser Glu Gly Asn Ala Ser Cys Pro
1             5                   10                  15

Glu Pro Pro Ala Pro Glu Pro Gly Pro Leu Phe Gly Ile Gly Val Glu
            20                  25                  30

Asn Phe Val Thr Leu Val Val Phe Gly Leu Ile Phe Ala Leu Gly Val
            35                  40                  45

Leu Gly Asn Ser Leu Val Ile Thr Val Leu Ala Arg Ser Lys Pro Gly
    50                  55                  60

Lys Pro Arg Ser Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
            115                 120                 125

Met Ser Val Asp Arg Tyr Val Ala Ile Val His Ser Arg Arg Ser Ser
    130                     135                 140

Ser Leu Arg Val Ser Arg Asn Ala Leu Leu Gly Val Gly Cys Ile Trp
145                 150                     155                 160

Ala Leu Ser Ile Ala Met Ala Ser Pro Val Ala Tyr His Gln Gly Leu
                165                     170                 175

Phe His Pro Arg Ala Ser Asn Gln Thr Phe Cys Trp Glu Gln Trp Pro
            180                     185                 190

Asp Pro Arg His Lys Lys Ala Tyr Val Val Cys Thr Phe Val Phe Gly
            195                     200                 205

Tyr Leu Leu Pro Leu Leu Leu Ile Cys Phe Cys Tyr Ala Lys Val Leu
        210                 215                 220

Asn His Leu His Lys Lys Leu Lys Asn Met Ser Lys Lys Ser Glu Ala
225                     230                 235                 240
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Ser Lys Lys Lys Thr Ala Gln Thr Val Leu Val Val Val Val Phe
            245             250             255

Gly Ile Ser Trp Leu Pro His His Ile Ile His Leu Trp Ala Glu Phe
            260             265             270

Gly Val Phe Pro Leu Thr Pro Ala Ser Phe Leu Phe Arg Ile Thr Ala
            275             280             285

His Cys Leu Ala Tyr Ser Asn Ser Ser Val Asn Pro Ile Ile Tyr Ala
    290             295             300

Phe Leu Ser Glu Asn Phe Arg Lys Ala Tyr Lys Gln Val Phe Lys Cys
305             310             315             320

His Ile Arg Lys Asp Ser His Leu Ser Asp Thr Lys Glu Asn Lys Ser
            325             330             335

Arg Ile Asp Thr Pro Pro Ser Thr Asn Cys Thr His Val
            340             345

<210> 13
<211> 359
<212> PRT
<213> Mus musculus

<400> 13
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

Met Glu Pro Leu Ser Leu Ala Ser Thr Pro Ser Trp Asn Ala Ser Ala
1               5                   10                  15

Ala Ser Ser Gly His Asn Trp Ser Leu Val Asp Pro Val Ser Pro Met
            20                  25                  30

Gly Ala Arg Ala Val Leu Val Pro Val Leu Tyr Leu Leu Val Cys Thr
            35                  40                  45

Val Gly Leu Gly Gly Asn Thr Leu Val Ile Tyr Val Val Leu Arg Tyr
        50                  55                  60

Ala Lys Met Lys Thr Val Thr Asn Val Tyr Ile Leu Asn Leu Ala Val
65                  70                  75                  80

Ala Asp Val Leu Phe Met Leu Gly Leu Pro Phe Leu Ala Thr Gln Asn
                85                  90                  95

Ala Val Ser Tyr Trp Pro Phe Gly Phe Leu Cys Arg Leu Val Met Thr
                100                 105                 110

Leu Asp Gly Ile Asn Gln Phe Thr Ser Ile Phe Cys Leu Met Val Met
            115                 120                 125

Ser Val Asp Arg Tyr Leu Ala Val Val His Pro Leu Arg Ser Ala Arg
    130                 135                 140

UNITED STATES PATENT AND TRADEMARK OFFICE
CERTIFICATE OF CORRECTION

| | |
|---|---|
| PATENT NO. | : 7,115,375 B2 |
| APPLICATION NO. | : 10/768878 |
| DATED | : October 3, 2006 |
| INVENTOR(S) | : John N. Feder, Gabriel A. Mintier and Chandra S. Ramanathan |

It is certified that error appears in the above-identified patent and that said Letters Patent is hereby corrected as shown below:

```
Trp Arg Arg Pro Arg Val Ala Lys Leu Ala Ser Ala Ala Val Trp Val
145             150             155                 160

Phe Ser Leu Leu Met Ser Leu Pro Leu Leu Val Phe Ala Asp Val Gln
                165             170                 175

Glu Gly Trp Gly Thr Cys Asn Leu Ser Trp Pro Glu Pro Val Gly Leu
            180             185                 190

Trp Gly Ala Ala Phe Ile Thr Tyr Thr Ser Val Leu Gly Phe Phe Gly
        195             200                 205

Pro Leu Leu Val Ile Cys Leu Cys Tyr Leu Leu Ile Val Val Lys Val
    210             215                 220

Lys Ala Ala Gly Met Arg Val Gly Ser Arg Arg Arg Arg Ser Glu Arg
225             230             235                 240

Lys Val Thr Arg Met Val Val Val Val Leu Val Phe Val Gly Cys
                245             250                 255

Trp Leu Pro Phe Phe Ile Val Asn Ile Val Asn Leu Ala Phe Thr Leu
            260             265                 270

Pro Glu Glu Pro Thr Ser Ala Gly Leu Tyr Phe Phe Val Val Val Leu
            275             280                 285
```

UNITED STATES PATENT AND TRADEMARK OFFICE
CERTIFICATE OF CORRECTION

PATENT NO.         : 7,115,375 B2
APPLICATION NO.    : 10/768878
DATED              : October 3, 2006
INVENTOR(S)        : John N. Feder, Gabriel A. Mintier and Chandra S. Ramanathan It is certified that error appears in the above-identified patent and that said Letters Patent is hereby corrected as shown below:

```
Ser Tyr Ala Asn Ser Cys Ala Asn Pro Leu Leu Tyr Gly Phe Leu Ser
    290             295             300

Asp Asn Phe Arg Gln Ser Phe Arg Lys Ala Leu Cys Leu Arg Arg Gly
305             310             315             320

Tyr Gly Val Glu Asp Ala Asp Ala Ile Glu Pro Arg Pro Asp Lys Ser
            325             330             335

Gly Arg Pro Gln Thr Thr Leu Pro Thr Arg Ser Cys Glu Ala Asn Gly
        340             345             350

Leu Met Gln Thr Ser Arg Leu
        355

<210>  14
<211>  360
<212>  PRT
<213>  Rattus norvegicus

<400>  14

Met Glu Pro Leu Ser Leu Ala Ser Thr Pro Ser Trp Asn Ala Ser Ala
1               5               10              15

Ala Ser Ser Gly Asn His Asn Trp Ser Leu Val Gly Ala Ser Pro Met
            20              25              30
```

UNITED STATES PATENT AND TRADEMARK OFFICE
CERTIFICATE OF CORRECTION

PATENT NO.        : 7,115,375 B2
APPLICATION NO. : 10/768878
DATED              : October 3, 2006
INVENTOR(S)     : John N. Feder, Gabriel A. Mintier and Chandra S. Ramanathan It is certified that error appears in the above-identified patent and that said Letters Patent is hereby corrected as shown below:

```
Gly Ala Arg Ala Val Leu Val Pro Val Leu Tyr Leu Leu Val Cys Thr
        35              40              45

Val Gly Leu Ser Gly Asn Thr Leu Val Ile Tyr Val Val Leu Arg His
    50              55              60

Ala Lys Met Lys Thr Val Thr Asn Val Tyr Ile Leu Asn Leu Ala Val
65              70              75              80

Ala Asp Val Leu Phe Met Leu Gly Leu Pro Phe Leu Ala Thr Gln Asn
            85              90              95

Ala Val Val Ser Tyr Trp Pro Phe Gly Phe Leu Cys Arg Leu Val Met
            100             105             110

Thr Leu Asp Gly Ile Asn Gln Phe Thr Ser Ile Phe Cys Leu Met Val
        115             120             125

Met Ser Val Asp Arg Tyr Leu Ala Val Val His Pro Leu Arg Ser Ala
    130             135             140

Arg Trp Arg Arg Pro Arg Val Ala Lys Met Ala Ser Ala Ala Val Trp
145             150             155             160

Val Phe Ser Leu Leu Met Ser Leu Pro Leu Leu Val Phe Ala Asp Val
            165             170             175
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Gln Glu Gly Trp Gly Thr Cys Asn Leu Ser Trp Pro Glu Pro Val Gly
            180                 185                 190

Leu Trp Gly Ala Ala Phe Ile Thr Tyr Thr Ser Val Leu Gly Phe Phe
            195                 200                 205

Gly Pro Leu Leu Val Ile Cys Leu Cys Tyr Leu Leu Ile Val Val Lys
            210                 215                 220

Val Lys Ala Ala Gly Met Arg Val Gly Ser Arg Arg Arg Arg Ser Glu
225             230                 235                 240

Pro Lys Val Thr Arg Met Val Val Val Val Leu Val Phe Val Gly
                245                 250                 255

Cys Trp Leu Pro Phe Phe Ile Val Asn Ile Val Asn Leu Ala Phe Thr
            260                 265                 270

Leu Pro Glu Glu Pro Thr Ser Ala Gly Leu Tyr Phe Phe Val Val Val
            275                 280                 285

Leu Ser Tyr Ala Asn Ser Cys Ala Asn Pro Leu Leu Tyr Gly Phe Leu
    290                 295                 300

Ser Asp Asn Phe Arg Gln Ser Phe Arg Lys Val Leu Cys Leu Arg Arg
305                 310                 315                 320
```

UNITED STATES PATENT AND TRADEMARK OFFICE
CERTIFICATE OF CORRECTION

| | |
|---|---|
| PATENT NO. | : 7,115,375 B2 |
| APPLICATION NO. | : 10/768878 |
| DATED | : October 3, 2006 |
| INVENTOR(S) | : John N. Feder, Gabriel A. Mintier and Chandra S. Ramanathan |

It is certified that error appears in the above-identified patent and that said Letters Patent is hereby corrected as shown below:

```
Gly Tyr Gly Met Glu Asp Ala Asp Ala Ile Glu Pro Arg Pro Asp Lys
            325                     330                 335

Ser Gly Arg Pro Gln Ala Thr Leu Pro Thr Arg Ser Cys Glu Ala Asn
            340                     345                 350

Gly Leu Met Gln Thr Ser Arg Ile
            355             360

<210>  15
<211>  426
<212>  PRT
<213>  Mus musculus

<400>  15

Met Ala Thr Val Thr Tyr Pro Ser Ser Glu Pro Met Thr Leu Asp Pro
1               5                   10                  15

Gly Asn Thr Ser Ser Thr Trp Pro Leu Asp Thr Thr Leu Gly Asn Thr
                20                  25                  30

Ser Ala Gly Ala Ser Leu Thr Gly Leu Ala Val Ser Gly Ile Leu Ile
                35                  40                  45

Ser Leu Val Tyr Leu Val Val Cys Val Val Gly Leu Leu Gly Asn Ser
    50                  55                  60
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Leu Val Ile Tyr Val Val Leu Arg His Thr Ser Ser Pro Ser Val Thr
65              70                  75                  80

Ser Val Tyr Ile Leu Asn Leu Ala Leu Ala Asp Glu Leu Phe Met Leu
            85                  90                  95

Gly Leu Pro Phe Leu Ala Ala Gln Asn Ala Leu Ser Tyr Trp Pro Phe
            100                 105                 110

Gly Leu Met Cys Arg Leu Val Met Ala Val Asp Gly Ile Asn Gln Phe 115                 120                 125

Thr Ser Ile Phe Cys Leu Thr Val Met Ser Val Asp Arg Tyr Leu Ala
    130                 135                 140

Val Val His Pro Thr Arg Ser Ala Arg Trp Arg Thr Ala Pro Val Ala
145                 150                 155                 160

Arg Thr Val Ser Arg Ala Val Trp Val Ala Ser Ala Val Val Val Leu
            165                 170                 175

Pro Val Val Val Phe Ser Gly Val Pro Arg Gly Met Ser Thr Cys His
            180                 185                 190

Met Gln Trp Pro Glu Pro Ala Ala Ala Trp Arg Thr Ala Phe Ile Ile
            195                 200                 205
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Tyr Met Ala Ala Leu Gly Phe Phe Gly Pro Leu Leu Val Ile Cys Leu
    210                 215                 220

Cys Tyr Leu Leu Ile Val Val Lys Val Arg Ser Thr Thr Arg Arg Val
225             230                 235                     240

Arg Ala Pro Ser Cys Gln Trp Val Gln Ala Pro Ala Cys Gln Arg Arg
                245                 250                 255

Arg Arg Ser Glu Arg Arg Val Thr Arg Met Val Val Ala Val Val Ala
            260                 265                 270

Leu Phe Val Leu Cys Trp Met Pro Phe Tyr Leu Leu Asn Ile Val Asn
        275                 280                 285

Val Val Cys Pro Leu Pro Glu Glu Pro Ala Phe Phe Gly Leu Tyr Phe
        290                 295                 300

Leu Val Val Ala Leu Pro Tyr Ala Asn Ser Cys Ala Asn Pro Ile Leu
305                 310                 315                 320

Tyr Gly Phe Leu Ser Tyr Arg Phe Lys Gln Gly Phe Arg Arg Ile Leu
                325                 330                 335

Leu Arg Pro Ser Arg Arg Ile Arg Ser Gln Glu Pro Gly Gly Pro Pro
                340                 345                 350
```

UNITED STATES PATENT AND TRADEMARK OFFICE
CERTIFICATE OF CORRECTION

PATENT NO.         : 7,115,375 B2
APPLICATION NO.    : 10/768878
DATED              : October 3, 2006
INVENTOR(S)        : John N. Feder, Gabriel A. Mintier and Chandra S. Ramanathan It is certified that error appears in the above-identified patent and that said Letters Patent is hereby corrected as shown below:

```
Glu Lys Thr Glu Glu Glu Glu Asp Glu Glu Glu Glu Glu Arg Arg Glu
        355             360             365

Glu Glu Glu Arg Arg Met Gln Arg Gly Gln Glu Met Asn Gly Arg Leu
    370             375             380

Ser Gln Ile Ala Gln Ala Gly Thr Ser Gly Gln Gln Pro Arg Pro Cys
385             390             395             400

Thr Gly Thr Ala Lys Glu Gln Gln Leu Leu Pro Gln Glu Ala Thr Ala
            405             410             415

Gly Asp Lys Ala Ser Thr Leu Ser His Leu 420             425
```

<210>  16
<211>  426
<212>  PRT
<213>  Rattus norvegicus

<400>  16

```
Met Ala Ala Val Thr Tyr Pro Ser Ser Val Pro Thr Thr Leu Asp Pro
1               5               10              15

Gly Asn Ala Ser Ser Ala Trp Pro Leu Asp Thr Ser Leu Gly Asn Ala
            20              25              30

Ser Ala Gly Thr Ser Leu Ala Gly Leu Ala Val Ser Gly Ile Leu Ile
            35              40              45
```

UNITED STATES PATENT AND TRADEMARK OFFICE
CERTIFICATE OF CORRECTION

PATENT NO.       : 7,115,375 B2
APPLICATION NO.  : 10/768878
DATED            : October 3, 2006
INVENTOR(S)      : John N. Feder, Gabriel A. Mintier and Chandra S. Ramanathan It is certified that error appears in the above-identified patent and that said Letters Patent is hereby corrected as shown below:

```
Ser Leu Val Tyr Leu Val Val Cys Val Val Gly Leu Leu Gly Asn Ser
    50              55                  60

Leu Val Ile Tyr Val Val Leu Arg His Thr Ser Ser Pro Ser Val Thr
65              70                  75                      80

Ser Val Tyr Ile Leu Asn Leu Ala Leu Ala Asp Glu Leu Phe Met Leu
                85                  90                  95

Gly Leu Pro Phe Leu Ala Ala Gln Asn Ala Leu Ser Tyr Trp Pro Phe
                100             105                 110

Gly Leu Met Cys Arg Leu Val Met Ala Val Asp Gly Ile Asn Gln Phe
                115             120                 125

Thr Ser Ile Phe Cys Leu Thr Val Met Ser Val Asp Arg Tyr Leu Ala
    130             135                 140

Val Val His Pro Thr Arg Ser Ala Arg Trp Arg Thr Ala Pro Val Ala
145             150                 155                     160

Arg Met Val Ser Ala Ala Val Trp Val Ala Ser Ala Val Val Val Leu
                165                 170                 175

Pro Val Val Val Phe Ser Gly Val Pro Arg Gly Met Ser Thr Cys His
            180                 185                 190
```

UNITED STATES PATENT AND TRADEMARK OFFICE
CERTIFICATE OF CORRECTION

PATENT NO.          : 7,115,375 B2
APPLICATION NO. : 10/768878
DATED                   : October 3, 2006
INVENTOR(S)        : John N. Feder, Gabriel A. Mintier and Chandra S. Ramanathan It is certified that error appears in the above-identified patent and that said Letters Patent is hereby corrected as shown below:

```
Met Gln Trp Pro Glu Pro Ala Ala Ala Trp Arg Thr Ala Phe Ile Ile
        195             200             205

Tyr Thr Ala Ala Leu Gly Phe Phe Gly Pro Leu Leu Val Ile Cys Leu
    210             215             220

Cys Tyr Leu Leu Ile Val Val Lys Val Arg Ser Thr Thr Arg Arg Val
225             230             235                     240

Arg Ala Pro Ser Cys Gln Trp Val Gln Ala Pro Ala Cys Gln Arg Arg
            245             250             255

Arg Arg Ser Glu Arg Arg Val Thr Arg Met Val Val Ala Val Val Ala
            260             265             270

Leu Phe Val Leu Cys Trp Met Pro Phe Tyr Leu Leu Asn Ile Val Asn
            275             280             285

Val Val Cys Pro Leu Pro Glu Glu Pro Ala Phe Phe Gly Leu Tyr Phe
    290             295             300

Leu Val Val Ala Leu Pro Tyr Ala Asn Ser Cys Ala Asn Pro Ile Leu
305             310             315                     320

Tyr Gly Phe Leu Ser Tyr Arg Phe Lys Gln Gly Phe Arg Arg Ile Leu
            325             330             335
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Leu Arg Pro Ser Arg Arg Val Arg Ser Gln Glu Pro Gly Gly Pro Pro
            340                 345                 350

Glu Lys Thr Glu Glu Glu Glu Asp Glu Glu Glu Glu Arg Arg Glu
        355                 360                 365

Glu Glu Glu Arg Arg Met Gln Arg Gly Gln Glu Met Asn Gly Arg Leu
    370                 375                 380

Ser Gln Ile Ala Gln Pro Gly Pro Ser Gly Gln Gln Gln Arg Pro Cys
385                 390                 395                 400

Thr Gly Thr Ala Lys Glu Gln Gln Leu Leu Pro Gln Glu Ala Thr Ala
                405                 410                 415

Gly Asp Lys Ala Ser Thr Leu Ser His Leu
                420                 425

<210>  17
<211>  418
<212>  PRT
<213>  Homo sapiens

<400>  17

Met Asp Met Leu His Pro Ser Ser Val Ser Thr Thr Ser Glu Pro Glu
1               5                   10                  15
```

UNITED STATES PATENT AND TRADEMARK OFFICE
CERTIFICATE OF CORRECTION

PATENT NO.       : 7,115,375 B2
APPLICATION NO.  : 10/768878
DATED            : October 3, 2006
INVENTOR(S)      : John N. Feder, Gabriel A. Mintier and Chandra S. Ramanathan It is certified that error appears in the above-identified patent and that said Letters Patent is hereby corrected as shown below:

```
Asn Ala Ser Ser Ala Trp Pro Pro Asp Ala Thr Leu Gly Asn Val Ser
            20                  25                  30

Ala Gly Pro Ser Pro Ala Gly Leu Ala Val Ser Gly Val Leu Ile Pro
            35                  40                  45

Leu Val Tyr Leu Val Val Cys Val Val Gly Leu Leu Gly Asn Ser Leu
        50                  55                  60

Val Ile Tyr Val Val Leu Arg His Thr Ala Ser Pro Ser Val Thr Asn
65                  70                  75                  80

Val Tyr Ile Leu Asn Leu Ala Leu Ala Asp Glu Leu Phe Met Leu Gly
                85                  90                  95

Leu Pro Phe Leu Ala Ala Gln Asn Ala Leu Ser Tyr Trp Pro Phe Gly
            100                 105                 110

Ser Leu Met Cys Arg Leu Val Met Ala Val Asp Gly Ile Asn Gln Phe
        115                 120                 125

Thr Ser Ile Phe Cys Leu Thr Val Met Ser Val Asp Arg Tyr Leu Ala
        130                 135                 140

Val Val His Pro Thr Arg Ser Ala Arg Trp Arg Thr Ala Pro Val Ala
145                 150                 155                 160
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Arg Thr Val Ser Ala Ala Val Trp Val Ala Ser Ala Val Val Val Leu
            165             170             175

Pro Val Val Val Phe Ser Gly Val Pro Arg Gly Met Ser Thr Cys His
            180             185             190

Met Gln Trp Pro Glu Pro Ala Ala Ala Trp Arg Ala Gly Phe Ile Ile
        195             200             205

Tyr Thr Ala Ala Leu Gly Phe Phe Gly Pro Leu Leu Val Ile Cys Leu
    210             215             220

Cys Tyr Leu Leu Ile Val Val Lys Val Arg Ser Ala Gly Arg Arg Val
225             230             235                     240

Trp Ala Pro Ser Cys Gln Arg Arg Arg Ser Glu Arg Arg Val Thr
            245             250             255

Arg Met Val Val Ala Val Val Ala Leu Phe Val Leu Cys Trp Met Pro
            260             265             270

Phe Tyr Val Leu Asn Ile Val Asn Val Val Cys Pro Leu Pro Glu Glu
        275             280             285

Pro Ala Phe Phe Gly Leu Tyr Phe Leu Val Val Ala Leu Pro Tyr Ala
        290             295             300
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Asn Ser Cys Ala Asn Pro Ile Leu Tyr Gly Phe Leu Ser Tyr Arg Phe
305                 310                 315                 320

Lys Gln Gly Phe Arg Arg Val Leu Leu Arg Pro Ser Arg Arg Val Arg
                325                 330                 335

Ser Gln Glu Pro Thr Val Gly Pro Pro Glu Lys Thr Glu Glu Glu Asp
                340                 345                 350

Glu Glu Glu Glu Asp Gly Glu Glu Ser Arg Glu Gly Gly Lys Gly Lys
            355                 360                 365

Glu Met Asn Gly Arg Val Ser Gln Ile Thr Gln Pro Gly Thr Ser Gly
        370                 375                 380

Gln Glu Arg Pro Pro Ser Arg Val Ala Ser Lys Glu Gln Gln Leu Leu
385                 390                 395                 400

Pro Gln Glu Ala Ser Thr Gly Glu Lys Ser Ser Thr Met Arg Ile Ser
                405                 410                 415

Tyr Leu

<210>  18
<211>  385
<212>  PRT
<213>  Mus musculus
```

UNITED STATES PATENT AND TRADEMARK OFFICE
CERTIFICATE OF CORRECTION

PATENT NO.       : 7,115,375 B2
APPLICATION NO.  : 10/768878
DATED            : October 3, 2006
INVENTOR(S)      : John N. Feder, Gabriel A. Mintier and Chandra S. Ramanathan It is certified that error appears in the above-identified patent and that said Letters Patent is hereby corrected as shown below:

```
<400> 18

Met Val Leu Lys Met Gly Pro Val Gly Ala Glu Ala Asp Glu Asn Gln
1               5                   10                  15

Thr Val Glu Val Lys Val Glu Pro Tyr Gly Pro Gly His Thr Thr Pro
            20                  25                  30

Arg Gly Glu Leu Pro Pro Asp Pro Glu Pro Glu Leu Ile Asp Ser Thr
            35                  40                  45

Lys Leu Val Glu Val Gln Val Ile Leu Ile Leu Ala Tyr Cys Ser Ile
            50                  55                  60

Ile Leu Leu Gly Val Val Gly Asn Ser Leu Val Ile His Val Val Ile
65                  70                  75                  80

Lys Phe Lys Ser Met Arg Thr Val Thr Asn Phe Phe Ile Ala Asn Leu
                85                  90                  95

Ala Val Ala Asp Leu Leu Val Asn Thr Leu Cys Leu Pro Phe Thr Leu
                100                 105                 110

Thr Tyr Thr Leu Met Gly Glu Trp Lys Met Gly Pro Val Leu Cys His
            115                 120                 125
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Leu Val Pro Tyr Ala Gln Gly Leu Ala Val Gln Val Ser Thr Ile Thr
    130             135             140

Leu Thr Val Ile Ala Leu Asp Arg His Arg Cys Ile Val Tyr His Leu
145             150             155             160

Glu Ser Lys Ile Ser Lys Arg Ile Ser Phe Leu Ile Ile Gly Leu Ala
                165             170             175

Trp Gly Ile Ser Ala Leu Leu Ala Ser Pro Leu Ala Ile Phe Arg Glu
            180             185             190

Tyr Ser Leu Ile Glu Ile Ile Pro Asp Phe Glu Ile Val Ala Cys Thr
        195             200             205

Glu Lys Trp Pro Gly Glu Glu Lys Ser Val Tyr Gly Thr Val Tyr Ser
    210             215             220

Leu Ser Thr Leu Leu Ile Leu Tyr Val Leu Pro Leu Gly Ile Ile Ser
225             230             235             240

Phe Ser Tyr Thr Arg Ile Trp Ser Lys Leu Arg Asn His Val Ser Pro
                245             250             255

Gly Ala Ala Ser Asp His Tyr His Gln Arg Arg His Lys Met Thr Lys
            260             265             270
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Met Leu Val Cys Val Val Val Phe Ala Val Ser Trp Leu Pro Leu
        275             280             285

His Ala Phe Gln Leu Ala Val Asp Ile Asp Ser His Val Leu Asp Leu
        290             295             300

Lys Glu Tyr Lys Leu Ile Phe Thr Val Phe His Ile Ile Ala Met Cys
305             310             315             320

Ser Thr Phe Ala Asn Pro Leu Leu Tyr Gly Trp Met Asn Ser Asn Tyr
                325             330             335

Arg Lys Ala Phe Leu Ser Ala Phe Arg Cys Glu Gln Arg Leu Asp Ala
            340             345             350

Ile His Ser Glu Val Ser Met Thr Phe Lys Ala Lys Lys Asn Leu Glu
            355             360             365

Val Lys Lys Asn Asn Gly Pro Thr Asp Ser Phe Ser Glu Ala Thr Asn
    370             375             380

Val
385

<210> 19
<211> 444
<212> PRT
<213> Homo sapiens
```

UNITED STATES PATENT AND TRADEMARK OFFICE
CERTIFICATE OF CORRECTION

PATENT NO.        : 7,115,375 B2
APPLICATION NO. : 10/768878
DATED             : October 3, 2006
INVENTOR(S)       : John N. Feder, Gabriel A. Mintier and Chandra S. Ramanathan It is certified that error appears in the above-identified patent and that said Letters Patent is hereby corrected as shown below:

<400> 19

Met Ser Gly Thr Lys Leu Glu Asp Ser Pro Pro Cys Arg Asn Trp Ser
1               5                   10                  15

Ser Ala Ser Glu Leu Asn Glu Thr Gln Glu Pro Phe Leu Asn Pro Thr
            20                  25                  30

Asp Tyr Asp Asp Glu Glu Phe Leu Arg Tyr Leu Trp Arg Glu Tyr Leu
            35                  40                  45

His Pro Lys Glu Tyr Glu Trp Val Leu Ile Ala Gly Tyr Ile Ile Val
    50                  55                  60

Phe Val Val Ala Leu Ile Gly Asn Val Leu Val Cys Val Ala Val Trp
65                  70                  75                  80

Lys Asn His His Met Arg Thr Val Thr Asn Tyr Phe Ile Val Asn Leu
                85                  90                  95

Ser Leu Ala Asp Val Leu Val Thr Ile Thr Cys Leu Pro Ala Thr Leu
            100                 105                 110

Val Val Asp Ile Thr Glu Thr Trp Phe Phe Gly Gln Ser Leu Cys Lys
            115                 120                 125

Val Ile Pro Tyr Leu Gln Thr Val Ser Val Ser Val Ser Val Leu Thr
            130                 135                 140

UNITED STATES PATENT AND TRADEMARK OFFICE
CERTIFICATE OF CORRECTION

PATENT NO.         : 7,115,375 B2
APPLICATION NO.    : 10/768878
DATED              : October 3, 2006
INVENTOR(S)        : John N. Feder, Gabriel A. Mintier and Chandra S. Ramanathan It is certified that error appears in the above-identified patent and that said Letters Patent is hereby corrected as shown below:

```
Leu Ser Cys Ile Ala Leu Asp Arg Trp Tyr Ala Ile Cys His Pro Leu
145             150                 155                 160

Met Phe Lys Ser Thr Ala Lys Arg Ala Arg Asn Ser Ile Val Ile Ile
            165                 170                 175

Trp Ile Val Ser Cys Ile Ile Met Ile Pro Gln Ala Ile Val Met Glu
            180             185                 190

Cys Ser Thr Val Phe Pro Gly Leu Ala Asn Lys Thr Thr Leu Phe Thr
            195             200                 205

Val Cys Asp Glu Arg Trp Gly Gly Glu Ile Tyr Pro Lys Met Tyr His
    210             215                 220

Ile Cys Phe Phe Leu Val Thr Tyr Met Ala Pro Leu Cys Leu Met Val
225             230                 235                 240

Leu Ala Tyr Leu Gln Ile Phe Arg Lys Leu Trp Cys Arg Gln Ile Pro
                245                 250                 255

Gly Thr Ser Ser Val Val Gln Arg Lys Trp Lys Pro Leu Gln Pro Val
            260                 265                 270

Ser Gln Pro Arg Gly Pro Gly Gln Pro Thr Lys Ser Arg Met Ser Ala
            275                 280                 285
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Val Ala Ala Glu Ile Lys Gln Ile Arg Ala Arg Arg Lys Thr Ala Arg
    290             295             300

Met Leu Met Val Val Leu Leu Val Phe Ala Ile Cys Tyr Leu Pro Ile
305             310             315                     320

Ser Ile Leu Asn Val Leu Lys Arg Val Phe Gly Met Phe Ala His Thr
            325             330                 335

Glu Asp Arg Glu Thr Val Tyr Ala Trp Phe Thr Phe Ser His Trp Leu
            340             345                 350

Val Tyr Ala Asn Ser Ala Ala Asn Pro Ile Ile Tyr Asn Phe Leu Ser
            355             360             365

Gly Lys Phe Arg Glu Glu Phe Lys Ala Ala Phe Ser Cys Cys Cys Leu
370             375                 380

Gly Val His His Arg Gln Glu Asp Arg Leu Thr Arg Gly Arg Thr Ser
385             390             395                     400

Thr Glu Ser Arg Lys Ser Leu Thr Thr Gln Ile Ser Asn Phe Asp Asn
            405             410                 415

Ile Ser Lys Leu Ser Glu Gln Val Val Leu Thr Ser Ile Ser Thr Leu
            420             425                 430
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
    Pro Ala Ala Asn Gly Ala Gly Pro Leu Gln Asn Trp
            435                 440

<210>  20
    <211>  44
    <212>  PRT
    <213>  Homo sapiens

<400>  20

Met Ser Pro Glu Cys Ala Arg Ala Ala Gly Asp Ala Pro Leu Arg Ser
    1               5                   10                  15

Leu Glu Gln Ala Asn Arg Thr Arg Phe Pro Phe Phe Ser Asp Val Lys
                    20                  25                  30

Gly Asp His Arg Leu Val Leu Ala Ala Val Glu Thr
                    35                  40

<210>  21
    <211>  7
    <212>  PRT
    <213>  Homo sapiens

<400>  21

Ala Arg Arg Arg Arg Arg Gly
    1               5
```

UNITED STATES PATENT AND TRADEMARK OFFICE
CERTIFICATE OF CORRECTION

PATENT NO.         : 7,115,375 B2
APPLICATION NO.    : 10/768878
DATED              : October 3, 2006
INVENTOR(S)        : John N. Feder, Gabriel A. Mintier and Chandra S. Ramanathan It is certified that error appears in the above-identified patent and that said Letters Patent is hereby corrected as shown below:

```
<210>  22
<211>  14
<212>  PRT
<213>  Homo sapiens

<400>  22

Arg Trp Thr Glu Ala Trp Leu Leu Gly Pro Val Ala Cys His
1               5                   10

<210>  23
<211>  21
<212>  PRT
<213>  Homo sapiens

<400>  23

Glu Arg Met Val Cys Ile Val His Leu Gln Arg Gly Val Arg Gly Pro
1               5                   10                  15

Gly Arg Arg Ala Arg
             20

<210>  24
<211>  31
<212>  PRT
<213>  Homo sapiens

<400>  24

Arg Val Val Pro Gln Arg Leu Pro Gly Ala Asp Gln Glu Ile Ser Ile
1               5                   10                  15
```

UNITED STATES PATENT AND TRADEMARK OFFICE
CERTIFICATE OF CORRECTION

PATENT NO.       : 7,115,375 B2
APPLICATION NO.  : 10/768878
DATED            : October 3, 2006
INVENTOR(S)      : John N. Feder, Gabriel A. Mintier and Chandra S. Ramanathan It is certified that error appears in the above-identified patent and that said Letters Patent is hereby corrected as shown below:

```
        Cys Thr Leu Ile Trp Pro Thr Ile Pro Gly Glu Ile Ser Trp Asp
                        20                  25                  30

<210>   25
<211>   37
<212>   PRT
<213>   Homo sapiens

<400>   25

Lys Ile Leu Gln Ile Thr Lys Ala Ser Arg Lys Arg Leu Thr Val Ser
        1               5                   10                  15

Leu Ala Tyr Ser Glu Ser His Gln Ile Arg Val Ser Gln Gln Asp Phe
                        20                  25                  30

Arg Leu Phe Arg Thr
                        35

<210>   26
<211>   6
<212>   PRT
<213>   Homo sapiens

<400>   26

Gln Asn Phe Lys Gln Asp
        1               5
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
<210>  27
<211>  45
<212>  PRT
<213>  Homo sapiens

<400>  27

Asn Pro Ile Leu Tyr Asn Met Thr Leu Cys Arg Asn Glu Trp Lys Lys
1               5                   10                  15

Ile Phe Cys Cys Phe Trp Phe Pro Glu Lys Gly Ala Ile Leu Thr Asp
                20                  25                  30

Thr Ser Val Lys Arg Asn Asp Leu Ser Ile Ile Ser Gly
                35                  40                  45

<210>  28
<211>  13
<212>  PRT
<213>  Homo sapiens

<400>  28

Gln Ile Thr Lys Ala Ser Arg Lys Arg Leu Thr Val Ser
1               5                   10

<210>  29
<211>  13
<212>  PRT
<213>  Homo sapiens

<400>  29
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
Ile Leu Thr Asp Thr Ser Val Lys Arg Asn Asp Leu Ser
1               5                   10

<210> 30
<211> 14
<212> PRT
<213> Homo sapiens

<400> 30

His Gln Ile Arg Val Ser Gln Gln Asp Phe Arg Leu Phe Arg
1               5                   10

<210> 31
<211> 14
<212> PRT
<213> Homo sapiens

<400> 31

Thr Lys Ala Ser Arg Lys Arg Leu Thr Val Ser Leu Ala Tyr
1               5                   10

<210> 32
<211> 14
<212> PRT
<213> Homo sapiens

<400> 32

Ser Leu Glu Gln Ala Asn Arg Thr Arg Phe Pro Phe Phe Ser
1               5                   10
```

UNITED STATES PATENT AND TRADEMARK OFFICE
CERTIFICATE OF CORRECTION

| | | |
|---|---|---|
| PATENT NO. | : 7,115,375 B2 | |
| APPLICATION NO. | : 10/768878 | |
| DATED | : October 3, 2006 | |
| INVENTOR(S) | : John N. Feder, Gabriel A. Mintier and Chandra S. Ramanathan | |

It is certified that error appears in the above-identified patent and that said Letters Patent is hereby corrected as shown below:

<210> 33
<211> 14
<212> PRT
<213> Homo sapiens

<400> 33

Asn Pro Ile Leu Tyr Asn Met Thr Leu Cys Arg Asn Glu Trp
1               5                   10

<210> 34
<211> 16
<212> PRT
<213> Homo sapiens

<400> 34

Ala Val Ser Leu Leu Gly Asn Val Cys Ala Leu Val Leu Val Ala Arg
1               5                   10                  15

<210> 35
<211> 16
<212> PRT
<213> Homo sapiens

<400> 35

Arg Arg Arg Arg Arg Gly Ala Thr Ala Cys Leu Val Leu Asn Leu Phe
1               5                   10                  15

<210> 36
<211> 16
<212> PRT
<213> Homo sapiens

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

<400> 36

| Trp | Phe | Pro | Glu | Lys | Gly | Ala | Ile | Leu | Thr | Asp | Thr | Ser | Val | Lys | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

<210> 37
<211> 19
<212> DNA
<213> Homo sapiens

<400> 37
tctgcctctc tgcgtcttc      19

<210> 38
<211> 20
<212> DNA
<213> Homo sapiens

<400> 38
agtcctggca ccaagaagtt      20

<210> 39
<211> 17
<212> DNA
<213> Homo sapiens

<400> 39
agccgagcca catcgct      17

<210> 40
<211> 19
<212> DNA
<213> Homo sapiens

UNITED STATES PATENT AND TRADEMARK OFFICE
CERTIFICATE OF CORRECTION

PATENT NO.       : 7,115,375 B2
APPLICATION NO.  : 10/768878
DATED            : October 3, 2006
INVENTOR(S)      : John N. Feder, Gabriel A. Mintier and Chandra S. Ramanathan It is certified that error appears in the above-identified patent and that said Letters Patent is hereby corrected as shown below:

```
<400> 40
gtgaccaggc gcccaatac                                                    19

<210> 41
<211> 28
<212> DNA
<213> Homo sapiens

<400> 41
caaatccgtt gactccgacc ttcacctt                                          28

<210> 42
<211> 39
<212> DNA
<213> Homo sapiens

<400> 42
gcagcagcgg ccgcaccgtg ctggtgctca tctttgcag                              39

<210> 43
<211> 33
<212> DNA
<213> Homo sapiens

<400> 43
gcagcagtcg acgccagaaa taatcgacaa gtc                                    33

<210> 44
<211> 39
<212> DNA
<213> Homo sapiens
```

UNITED STATES PATENT AND TRADEMARK OFFICE
CERTIFICATE OF CORRECTION

PATENT NO. : 7,115,375 B2
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
<400> 44
gcagcagcgg ccgcatgtcc cctgaatgcg cgcgggcag                     39

<210> 45
<211> 37
<212> DNA
<213> Homo sapiens

<400> 45
gcagcagtcg acgtttaggg ctgaattagc aaatgtg                       37

<210> 46
<211> 22
<212> DNA
<213> Homo sapiens

<400> 46
tcacaaaggc atcaaggaag ag                                       22

<210> 47
<211> 17
<212> DNA
<213> Homo sapiens

<400> 47
tgggacacgc ggatctg                                             17

<210> 48
<211> 26
<212> DNA
<213> Homo sapiens
```

UNITED STATES PATENT AND TRADEMARK OFFICE
CERTIFICATE OF CORRECTION

PATENT NO. : 7,115,375 B2  Page 53 of 54
APPLICATION NO. : 10/768878
DATED : October 3, 2006
INVENTOR(S) : John N. Feder, Gabriel A. Mintier and Chandra S. Ramanathan It is certified that error appears in the above-identified patent and that said Letters Patent is hereby corrected as shown below:

```
<400>  48
ctctccgagt aggccaggct taccgt                                26

<210>  49
<211>  19
<212>  DNA
<213>  Homo sapiens

<400>  49
tctgcctctc tgcgtcttc                                        19

<210>  50
<211>  20
<212>  DNA
<213>  Homo sapiens

<400>  50
agtcctggca ccaagaagtt                                       20
```

UNITED STATES PATENT AND TRADEMARK OFFICE
CERTIFICATE OF CORRECTION

PATENT NO.       : 7,115,375 B2
APPLICATION NO.  : 10/768878
DATED            : October 3, 2006
INVENTOR(S)      : John N. Feder, Gabriel A. Mintier and Chandra S. Ramanathan It is certified that error appears in the above-identified patent and that said Letters Patent is hereby corrected as shown below:

Column 113 - What is claimed is:

Claim 2, line 39 - insert the word --to-- at the end of line

Claim 2, line 40 - after the word "of", delete the word "to"

Claim 2, line 39 and 40 should now read "measurement comprises hybridization between said RNA to the complete complementary sequence of a member of the"

Signed and Sealed this

Ninth Day of January, 2007

JON W. DUDAS
*Director of the United States Patent and Trademark Office*